United States Patent
Araujo et al.

(10) Patent No.: US 11,166,959 B2
(45) Date of Patent: Nov. 9, 2021

(54) ISOFURANONE COMPOUNDS USEFUL AS HPK1 INHIBITORS

(71) Applicant: BRISTOL-MYERS SQUIBB COMPANY, Princeton, NJ (US)

(72) Inventors: Erika M. V. Araujo, Woodbridge, CT (US); Yan Chen, Yardley, PA (US); Bireshwar Dasgupta, Doylestown, PA (US); Andrew P. Degnan, Jamison, PA (US); Matthew D. Hill, Windham, NH (US); Godwin Kwame Kumi, Morrisville, PA (US); Harold A. Mastalerz, Guilford, CT (US); Mark D. Wittman, Hopkinton, MA (US); Bradley C. Pearce, East Hampton, CT (US); Guifen Zhang, Hopkinton, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/761,449

(22) PCT Filed: Nov. 5, 2018

(86) PCT No.: PCT/US2018/059137
§ 371 (c)(1),
(2) Date: May 4, 2020

(87) PCT Pub. No.: WO2019/090198
PCT Pub. Date: May 9, 2019

(65) Prior Publication Data
US 2020/0390776 A1 Dec. 17, 2020

Related U.S. Application Data

(60) Provisional application No. 62/581,847, filed on Nov. 6, 2017.

(51) Int. Cl.

| | |
|---|---|
| *A61K 31/5377* | (2006.01) |
| *A61K 31/506* | (2006.01) |
| *A61P 35/00* | (2006.01) |
| *A61K 45/06* | (2006.01) |
| *C07D 405/12* | (2006.01) |
| *C07D 405/14* | (2006.01) |
| *C07D 413/14* | (2006.01) |
| *C07D 453/02* | (2006.01) |
| *C07D 491/048* | (2006.01) |
| *C07D 498/10* | (2006.01) |
| *C07D 519/00* | (2006.01) |

(52) U.S. Cl.
CPC ........ *A61K 31/5377* (2013.01); *A61K 31/506* (2013.01); *A61K 45/06* (2013.01); *A61P 35/00* (2018.01); *C07D 405/12* (2013.01); *C07D 405/14* (2013.01); *C07D 413/14* (2013.01); *C07D 453/02* (2013.01); *C07D 491/048* (2013.01); *C07D 498/10* (2013.01); *C07D 519/00* (2013.01)

(58) Field of Classification Search
None
See application file for complete search history.

(56) References Cited

U.S. PATENT DOCUMENTS 7,589,200 B2    9/2009  Singh et al.

FOREIGN PATENT DOCUMENTS

| WO | 2008003766 A2 | 1/2008 |
|---|---|---|
| WO | 2009145856 A1 | 12/2009 |
| WO | 2011090760 A1 | 7/2011 |
| WO | 2012015972 A1 | 2/2012 |
| WO | 2012053606 A1 | 4/2012 |
| WO | 2013017461 A1 | 2/2013 |
| WO | 2015025197 A1 | 2/2015 |
| WO | 2016090300 A1 | 6/2016 |
| WO | 2016205942 A1 | 12/2016 |
| WO | 018049152 A1 | 3/2018 |
| WO | 2018049191 A1 | 3/2018 |
| WO | 2018049200 A1 | 3/2018 |

(Continued)

OTHER PUBLICATIONS

Alzabin et al., "Hematopoietic Progenitor Kinase 1 Is a Negative Regulator of Dendritic Cell Activation", The Journal of Immunology 182(10), 6187-6194 (2009).

(Continued)

*Primary Examiner* — Samantha L Shterengarts
(74) *Attorney, Agent, or Firm* — Gary Greenblatt

(57) ABSTRACT

Disclosed are compounds of Formula (I) or a salt thereof, wherein: X is CH or N; Y is CR5 or N; and R1, R2, R3, R4, and R5 are defined herein. Also disclosed are methods of using such compounds to modulate or inhibit the enzymatic activity of hematopoietic progenitor kinase 1 (HPK1), and pharmaceutical compositions comprising such compounds. These compounds are useful in the treatment of viral infections and proliferative disorders, such as cancer.

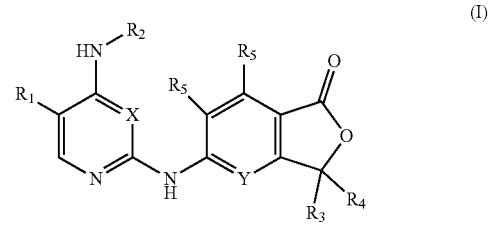

(I)

15 Claims, 1 Drawing Sheet
Specification includes a Sequence Listing.

(56) References Cited

FOREIGN PATENT DOCUMENTS

| WO | 2018049214 | A1 | 3/2018 |
| WO | 2018102366 | A1 | 6/2018 |
| WO | 018183956 | A1 | 10/2018 |
| WO | 2018183964 | A1 | 10/2018 |

OTHER PUBLICATIONS

Gross et al., "Targeting cancer with kinases inhibitors", The Journal of Clinical Investigation, 125(5), 1780-1789 (2015).
International Preliminary Report on Patentability No. PCT/US2018/059137, dated May 12, 2020.
International Search Report for PCT/US2018/059137, filed Nov. 5, 2018.
Sawasdikosol et al., "HPK1 as a novel target for cancer immunotherapy", Immunol Res 54(1-3), 262-5 (2012); published online Apr. 4, 2012.

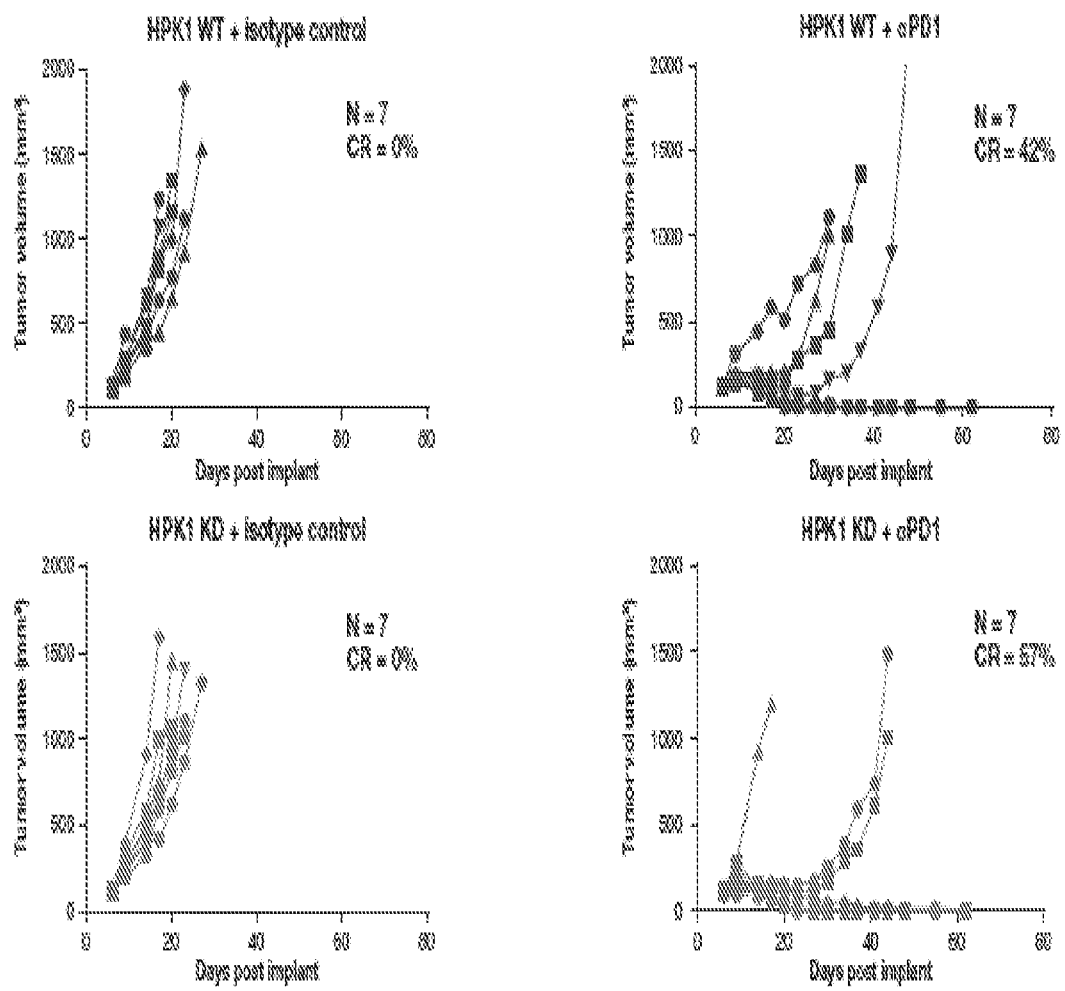

ISOFURANONE COMPOUNDS USEFUL AS HPK1 INHIBITORS

CROSS REFERENCE

This application is a 371 application of International Application No. PCT/US2018/059137 filed on Nov. 5, 2018, which claims the benefit of U.S. Provisional Application Ser. No. 62/581,847, filed Nov. 6, 2017, the content of each is hereby fully incorporated by reference in its entirety for all purposes.

The present invention generally relates to isofuranone compounds that modulate or inhibit the enzymatic activity of hematopoietic progenitor kinase 1 (HPK1). Provided herein are isofuranone compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. However, although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively subvert anti-tumor immunity. These mechanisms include dysfunctional T-cell signaling (Mizoguchi et al., (1992) Science 258:1795-98), suppressive regulatory cells (Facciabene et al., (2012) Cancer Res. 72:2162-71), and the co-opting of endogenous "immune checkpoints," which serve to down-modulate the intensity of adaptive immune responses and protect normal tissues from collateral damage, by tumors to evade immune destruction (Topalian et al., (2012a) Curr. Opin. Immunol. 24:1-6; Mellman et al. (2011) Nature 480:480-489).

HPK1 is a STE20-related serine threonine kinase that acts as a down-regulator of T and B cell functions through the AP-1, NFkB, NFAT, Erk2, and Fos pathways. HPK1 has been shown to inducibly associate with the adapter protein SLP-76 and phosphorylate SLP-76 specifically on serine 376. Mutation of serine 376 to alanine resulted in IL-2 gene transcription relative to the wild type (Di Bartolo et al., JExp. Med. (2007) 204:681-691). HPK1 deficiency results in enhanced TCR-induced phosphorylation of SLP-76 and Erk, increased Ca flux, and increased production of cytokines and antigen-specific antibodies indicating that HPK1 negatively regulates TCR signaling and T cell-mediated immune responses (Shui et al., Nature Immunology (2007) Vol 8: 84-91). In addition HPK1 (−/−) T cells are resistant to the suppressive and apoptotic effects of prostaglandin PGE2 (Sawasdikosol et al., Cancer Immunol. Immunother. (2010) 59:419-429). Bone marrow derived DC's from HPK1 deficient mice (HPK1−/−) are superior to DC's derived from wild type mice in stimulating T cell proliferation in vivo and in vitro. These BMDC's are significantly resistant to LPS-induced apoptosis and eliminate s.c. Lewis Lung carcinoma more efficiently than wild type mice in vivo (Alzabin et al., Journal of Immunology (2009), 182: 6187-6194).

Thus, HPK1 is now viewed as a novel target for cancer immunotherapy (Sawasdikosol et al., Immunol Res. (2012) 54: 262-5). Given that HPK1 is not expressed in any major organs outside of the hematopoietic system, it is less likely that an inhibitor of HPK1 kinase activity would cause any serious side effects. Since the result of HPK1 target inhibition in T cells should result in T cell stimulation, sufficient kinase selectivity over kinase targets that result in T cell suppression is necessary to achieving sufficient T cell activation.

There still remains a need for compounds useful as inhibitors of HPK1. Further, there still remains a need for compounds useful as inhibitors of HPK1 with selectivity over kinase targets such as IRAK-4 that result in T cell suppression.

Accordingly, an agent which is safe and effective in inhibiting the function of HPK1, resulting in functional T cell activation would be an important addition for the treatment of patients with diseases or conditions affected by the activity of the enzyme.

Applicants have found compounds that have activity as HPK1 inhibitors. Applicants have found compounds that have activity as HPK1 inhibitors and have selectivity over IRAK-4. These compounds are provided to be useful as pharmaceuticals with desirable stability, bioavailability, therapeutic index, and toxicity values that are important to their drugability.

SUMMARY OF THE INVENTION

The present invention provides isofuranone compounds of Formula (I), which are useful as modulators of HPK1 activity, including salts thereof.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder associated with the activity of HPK1, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment of HPK1 related conditions.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

BRIEF DESCRIPTION OF THE DRAWING

The invention is illustrated by reference to the accompanying drawings described below.

FIG. 1 shows the antitumor efficacy with anti-PD-1 therapy in a murine colon adenomacarcinoma model.

DETAILED DESCRIPTION

The first aspect of the present invention provides at least one compound of Formula (I):

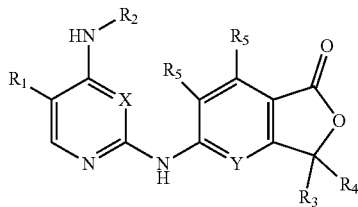

or a salt thereof, wherein:
X is CH or N;
Y is $CR_5$ or N;
$R_1$ is —C(O)OH, —C(O)O($C_{1-3}$ alkyl), —C(O)$NHR_{1a}$, —NHC(O)$R_{1a}$, —C(O)$NHNH_2$, —C(O)NHNHC(O)$R_{1b}$, —C(O)NHNHC(=NCH$_2$CH$_3$(NH(CH$_2$)$_{2-4}$N(CH$_3$)$_2$), 1,8-dioxa-3-azaspiro[4.5]dec-2-enyl, or a cyclic group selected from oxadiazolyl, thiazolyl, oxazolyl, pyridinyl, pyrimidinyl, thiadiazolyl, pyrazinyl, imidazolyl, triazolyl, isoxazolyl, and dihydrooxazolyl, each substituted with zero to 2 $R_{1c}$.
$R_{1a}$ is $C_{1-4}$ alkyl, $C_{1-3}$ fluoroalkyl, $C_{1-2}$ cyanoalkyl, —CH$_2$CH$_2$OCH$_3$, —CH$_2$C≡CH, —(CH$_2$)$_{2-3}$N(CH$_3$)$_2$, —CH(CH$_3$)(phenyl), or —(CH$_2$)$_m R_a$;
$R_a$ is $C_{3-7}$ cycloalkyl, $C_{5-8}$ bicycloalkyl, 4- to 7-membered heterocyclyl, 5- to 8-membered bicyclic nitrogen containing heterocyclyl, phenyl, or 5- to 6-membered heteroaryl, each substituted with zero to 4 $R_x$;
each $R_x$ is independently selected from F, Cl, —CN, —OH, $C_{1-3}$ alkyl, —CD$_3$, —CF$_3$, —OCH$_3$, —CH$_2$(morpholinyl), phenyl, and benzyl;
m is zero, 1, 2, 3, 4, or 5;
$R_{1b}$ is —C(CH$_3$)$_2$OH, —C(CF$_3$)(CH$_3$)OH, cyclopropyl, pyridinyl, or pyrazinyl;
each $R_{1c}$ is independently F, $C_{1-4}$ alkyl, $C_{2-6}$ hydroxyalkyl, $C_{1-4}$ fluoroalkyl, $C_{2-4}$ hydroxy-fluoroalkyl, —(CH$_2$)$_n R_c$, =O, —S($C_{1-2}$ alkyl), azetidinyl, morpholinyl, piperidinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, (methoxycarbonyl)aminobicyclo[1.1.1]pentanyl, or $C_{3-6}$ cycloalkyl substituted with zero to 2 substituents independently selected from F, —CN, —CF$_3$, —CH$_2$OH, and —OC(O)(difluorazetidinyl);
$R_c$ is 4- to 7-membered heterocyclyl or 5- to 8-membered bicyclic nitrogen containing heterocyclyl, each substituted with zero to 4 $R_x$;
n is zero, 1, 2, 3, 4, or 5;

$R_2$ is:
(i) $C_{1-6}$ alkyl substituted with zero to 6 substituents independently selected from F, Cl, —CN, —OH, $C_{1-3}$ alkoxy, $C_{1-3}$ fluoroalkoxy, $C_{3-6}$ cycloalkyl, and —NR$_y$R$_y$;
(ii) —CHR$_{2a}$R$_{2b}$, —(CH$_2$)$_{1-3}$NR$_y$(CH$_2$)$_{1-3}$NR$_y$R$_y$, —(CR$_y$R$_y$)$_{1-2}$NR$_y$C(O)OCH$_2$(phenyl), —CHR$_{2b}$CH$_2$R$_{2a}$, or —CH$_2$CH$_2$C(O)R$_{2a}$; or
(iii) a cyclic group selected from cyclopropyl, indazolyl, phenyl, piperidinyl, pyrazolyl, oxetanyl, and tetrahydropyrido[3,4-d]pyrimidinyl, each substituted with zero to 1 substituent selected from —CN, —CH$_3$, —SCH$_3$, pyrimidinyl, and phenyl;
$R_{2a}$ is $C_{3-6}$ cycloalkyl, oxadiazolyl, oxazolyl, oxetanyl, phenyl, pyrazolyl, pyrazolo[1,5-a]pyridinyl, pyridazinyl, pyridinyl, pyrimidinyl, pyrrolidinyl, tetrahydropyrido[3,4-d]pyrimidinyl, or thiazolyl, each substituted with zero to 2 $R_{2c}$;
$R_{2b}$ is H, —OH, $C_{1-3}$ alkyl, $C_{1-2}$ fluoroalkyl, $C_{1-3}$ hydroxyalkyl, —CH$_2$OCH$_3$, —CH$_2$OCF$_3$, —CH$_2$NR$_y$R$_y$, —CH$_2$S($C_{1-2}$ alkyl), or —CH$_2$N$_3$;
each $R_{2c}$ is independently F, Cl, —CN, —OH, $C_{1-2}$ alkyl, $C_{1-3}$ hydroxyalkyl, $C_{1-2}$ aminoalkyl, $C_{1-2}$ alkoxy, $C_{1-2}$ fluoroalkoxy, —CH$_2$O($C_{1-2}$ alkyl), —NR$_y$C(O)($C_{1-2}$ alkyl), —S($C_{1-2}$ alkyl), —S(O)$_2$($C_{1-4}$ alkyl), phenyl, methyloxiranyl, or pyrimidinyl;
each $R_y$ is independently H or —CH$_3$;
$R_3$ is H or —CH$_3$;
$R_4$ is H or —CH$_3$;
or $R_3$ and $R_4$ together with the carbon atom to which they are attached form a $C_{4-6}$ cycloalkyl ring; and
each $R_5$ is H or halo.

In one embodiment, a compound of Formula (I) or a salt thereof is provided wherein X is N; Y is $CR_5$ or N; and $R_1$, $R_2$, $R_3$, $R_4$, and $R_5$ are defined in the first aspect. Compounds of this embodiment have the structure of Formula (II):

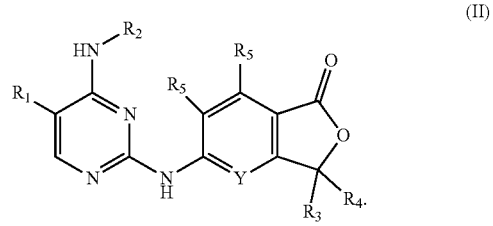

In one embodiment, a compound of Formula (I) or a salt thereof is provided wherein X is N; Y is $CR_5$; and $R_1$, $R_2$, $R_3$, $R_4$, and $R_5$ are defined in the first aspect. Compounds of this embodiment have the structure of Formula (IIa):

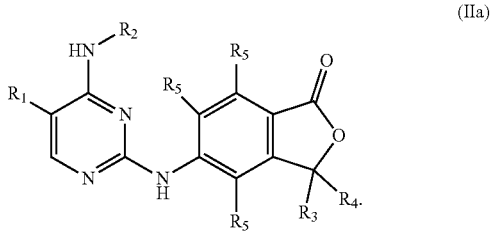

In one embodiment, a compound of Formula (I) or a salt thereof is provided wherein X is N; Y is N; and $R_1$, $R_2$, $R_3$, $R_4$, and $R_5$ are defined in the first aspect. Compounds of this embodiment have the structure of Formula (IIb):

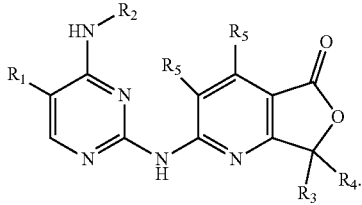

(IIb)

In one embodiment, a compound of Formula (I) or a salt thereof is provided wherein X is CH; Y is $CR_5$ or N; and $R_1$, $R_2$, $R_3$, $R_4$, and $R_5$ are defined in the first aspect. Compounds of this embodiment have the structure of Formula (III):

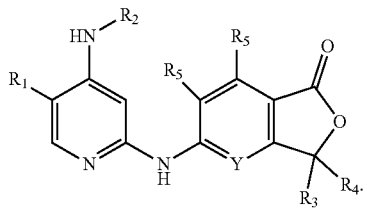

(III)

In one embodiment, a compound of Formula (I) or a salt thereof is provided wherein X is CH; Y is $CR_5$; and $R_1$, $R_2$, $R_3$, $R_4$, and $R_5$ are defined in the first aspect. Compounds of this embodiment have the structure of Formula (IIIa):

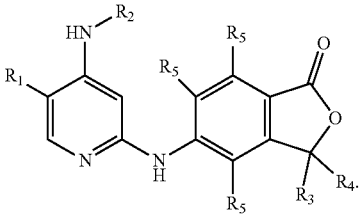

(IIIa)

In one embodiment, a compound of Formula (I) or a salt thereof is provided wherein X is CH; Y is N; and $R_1$, $R_2$, $R_3$, $R_4$, and $R_5$ are defined in the first aspect. Compounds of this embodiment have the structure of Formula (IIIb):

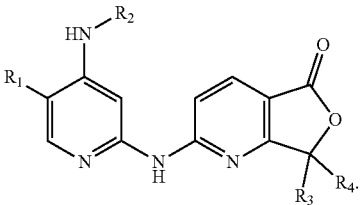

(IIIb)

One embodiment provides a compound of Formula (I) or a salt thereof, wherein $R_1$ is —C(O)OH, —C(O)O($C_{1-3}$ alkyl), —C(O)$NHR_{1a}$, —NHC(O)$R_{1a}$, —C(O)NHNH$_2$, —C(O)NHNHC(O)$R_{1b}$, or —C(O)NHNHC(=NCH$_2$CH$_3$ (NH(CH$_2$)$_{2-4}$N(CH$_3$)$_2$); and X, Y, $R_2$, $R_3$, $R_4$, $R_5$, $R_{1a}$, and $R_{1b}$ are defined in the first aspect. Included in this embodiment are compounds in which $R_{1a}$ is $C_{2-4}$ alkyl, —CH$_2$CH$_2$OCH$_3$, —CH$_2$C≡CH, —(CH$_2$)$_{2-3}$N(CH$_3$)$_2$, pyrrolidinyl substituted with —CH$_2$(phenyl), —CH(CH$_3$)(phenyl), —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —CH$_2$CH$_2$CH$_2$(imidazolyl), —NHC(O)(cyclopropyl), —NHC(O)(pyrazinyl), —NHC(O)(pyridinyl), or cyclopropyl substituted with phenyl. Also included in this embodiment are compounds in which $R_{1a}$ is cyclopropyl substituted with phenyl, pyrrolidinyl substituted with —CH$_2$(phenyl), —CH(CH$_3$)(phenyl), —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —NHC(O)(cyclopropyl), —NHC(O)(pyrazinyl), or —NHC(O)(pyridinyl).

One embodiment provides a compound of Formula (I) or a salt thereof, wherein $R_1$ is —C(O)$NHR_{1a}$ or —NHC(O)$R_{1a}$; and X, Y, $R_2$, $R_3$, $R_4$, $R_5$, and $R_{1a}$ are defined in the first aspect. Included in this embodiment are compounds in which $R_{1a}$ is $C_{2-4}$ alkyl, —CH$_2$CH$_2$OCH$_3$, —CH$_2$C° CH, —(CH$_2$)$_{2-3}$N(CH$_3$)$_2$, pyrrolidinyl substituted with —CH$_2$(phenyl), —CH(CH$_3$)(phenyl), —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —CH$_2$CH$_2$CH$_2$(imidazolyl), —NHC(O)(cyclopropyl), —NHC(O)(pyrazinyl), —NHC(O)(pyridinyl), or cyclopropyl substituted with phenyl. Also included in this embodiment are compounds in which $R_2$ is —CH(phenyl)CH$_2$OH.

One embodiment provides a compound of Formula (I) or a salt thereof, wherein $R_1$ is —C(O)NHNHC(O)$R_{1b}$; and X, Y, $R_2$, $R_3$, $R_4$, $R_5$, and $R_{1b}$ are defined in the first aspect. Included in this embodiment are compounds in which $R_{1b}$ is —C(CH$_3$)$_2$OH, —C(CF$_3$)(CH$_3$)OH, cyclopropyl, pyridinyl, or pyrazinyl. Also included in this embodiment are compounds in which $R_2$ is —CH(phenyl)CH$_2$OH.

One embodiment provides a compound of Formula (I) or a salt thereof, wherein $R_1$ is 1,8-dioxa-3-azaspiro[4.5]dec-2-enyl; and X, Y, $R_2$, $R_3$, $R_4$, and $R_5$ are defined in the first aspect.

One embodiment provides a compound of Formula (I) or a salt thereof, wherein $R_1$ is a cyclic group selected from oxadiazolyl, thiazolyl, oxazolyl, pyridinyl, pyrimidinyl, thiadiazolyl, pyrazinyl, imidazolyl, triazolyl, isoxazolyl, and dihydrooxazolyl, each substituted with zero to 2 $R_{1c}$; and X, Y, $R_2$, $R_3$, $R_4$, $R_5$, and $R_{1c}$ are defined in the first aspect. Included in this embodiment are compounds in which each $R_{1c}$ is independently $C_{1-4}$ alkyl, —C(CH$_3$)$_2$OH, —C(CH$_3$)$_2$CH$_2$CH$_2$OH, —C(CF$_3$)(CH$_3$)OH, =O, —CH$_2$(morpholinyl), difluorocyclobutyl, azetidinyl, morpholinyl, piperidinyl, tetrahydropyranyl, dioxotetrahydrothiopyranyl, fluorophenyl, pyridinyl, pyridazinyl, azabicyclo[2.2.2]octanyl, aminobicyclo[1.1.1]pentanyl, dimethylaminobicyclo[1.1.1]pentanyl, acetamidobicyclo[1.1.1]pentanyl, (methoxycarbonyl)aminobicyclo[1.1.1]pentanyl, cyclopropyl, trifluoromethylcyclopropyl, hydroxymethylcyclopropyl, or cyclopropyl substituted with —OC(O)(difluorazetidinyl).

Also included in this embodiment are compounds in which each $R_{1c}$ is independently $C_{1-4}$ alkyl, —C(CH$_3$)$_2$OH, —C(CH$_3$)$_2$CH$_2$CH$_2$CH$_2$OH, —C(CF$_3$)(CH$_3$)OH, =O, —CH$_2$(morpholinyl), cyclopropyl, trifluoromethylcyclopropyl, cyanocyclopropyl, hydroxymethylcyclopropyl, cyclopropyl substituted with —OC(O)(difluorazetidinyl), difluorocyclobutyl, morpholinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, or (methoxycarbonyl)aminobicyclo[1.1.1]pentanyl; and X, Y, $R_1$, $R_2$, $R_3$, $R_4$, and $R_5$ are defined in the first aspect.

One embodiment provides a compound of Formula (I) or a salt thereof, wherein $R_1$ is oxadiazolyl substituted with zero to 2 $R_{1c}$; and X, Y, $R_2$, $R_3$, $R_4$, $R_5$, and $R_{1c}$ are defined in the first aspect. Included in this embodiment are compounds in which each $R_{1c}$ is independently $C_{1-4}$ alkyl, —C(CH$_3$)$_2$OH, —C(CH$_3$)$_2$CH$_2$CH$_2$CH$_2$OH, —C(CF$_3$)(CH$_3$)OH, =O, —CH$_2$(morpholinyl), cyclopropyl, trifluoromethylcyclopropyl, cyanocyclopropyl, hydroxymethylcyclopropyl, cyclopropyl substituted with —OC(O)(difluorazetidinyl), difluorocyclobutyl, azetidinyl, morpholinyl, piperidinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, or (methoxycarbonyl)aminobicyclo[1.1.1]pentanyl. Also included in this embodiment are compounds in which each $R_{1c}$ is independently $C_{1-4}$ alkyl, —C(CH$_3$)$_2$OH, —C(CH$_3$)$_2$CH$_2$CH$_2$CH$_2$OH, —C(CF$_3$)(CH$_3$)OH, =O, —CH$_2$(morpholinyl), difluorocyclobutyl, morpholinyl, tetrahydropyranyl, dioxotetrahydrothiopyranyl, fluorophenyl, pyridinyl, pyridazinyl, azabicyclo[2.2.2]octanyl, aminobicyclo[1.1.1]pentanyl, dimethylaminobicyclo[1.1.1]pentanyl, acetamidobicyclo[1.1.1]pentanyl, (methoxycarbonyl)aminobicyclo[1.1.1]pentanyl, cyclopropyl, trifluoromethylcyclopropyl, hydroxymethylcyclopropyl, or cyclopropyl substituted with —OC(O)(difluorazetidinyl).

One embodiment provides a compound of Formula (I) or a salt thereof, wherein $R_2$ is $C_{1-6}$ alkyl substituted with zero to 6 substituents independently selected from F, Cl, —CN, —OH, $C_{1-3}$ alkoxy, $C_{1-3}$ fluoroalkoxy, $C_{3-6}$ cycloalkyl, and —NR$_y$R$_y$; and X, Y, $R_1$, $R_3$, $R_4$, $R_5$, and $R_y$ are defined in the first aspect. Included in this embodiment are compounds in which $R_2$ is $C_{1-5}$ alkyl substituted with zero to 1 substituent selected from —OH and —NR$_y$R$_y$. Also included in this embodiment are compounds in which $R_2$ is —CH$_2$CH$_2$C(CH$_3$)$_2$NH$_2$ or —CH$_2$C(CH$_3$)$_2$CH$_2$NH$_2$.

One embodiment provides a compound of Formula (I) or a salt thereof, wherein $R_2$ is —CHR$_{2a}$R$_{2b}$, —(CH$_2$)$_{1-3}$NR$_y$(CH$_2$)$_{1-3}$NR$_y$R$_y$, —(CR$_y$R$_y$)$_{1-2}$NR$_y$C(O)OCH$_2$(phenyl), —CHR$_{2b}$CH$_2$R$_{2a}$, or —CH$_2$CH$_2$C(O)R$_{2a}$; and X, Y, $R_1$, $R_{2a}$, $R_{2b}$, $R_3$, $R_4$, $R_5$, and $R_y$ are defined in the first aspect. Included in this embodiment are compounds in which $R_2$ is —CHR$_{2a}$R$_{2b}$. Also included in this embodiment are compounds in which $R_2$ is —CH$_2$(thiazolyl), —CH$_2$(pyridinyl), —CH(cyclopropyl)CH$_2$OH, —CH(phenyl)CH$_2$OH, —CH(fluorophenyl)CH$_2$OH, or —CH$_2$(hydroxypropylphenyl).

One embodiment provides a compound of Formula (I) or a salt thereof, wherein $R_2$ is a cyclic group selected from cyclopropyl, indazolyl, phenyl, piperidinyl, pyrazolyl, oxetanyl, and tetrahydropyrido[3,4-d]pyrimidinyl, each substituted with zero to 1 substituent selected from —CN, —CH$_3$, —SCH$_3$, pyrimidinyl, and phenyl; and X, Y, $R_1$, $R_3$, $R_4$, $R_5$, and $R_y$ are defined in the first aspect. Included in this embodiment are compounds in which $R_2$ is indazolyl.

One embodiment provides a compound of Formula (I) or a salt thereof, wherein $R_2$ is $C_{3-6}$ cycloalkyl; and X, Y, $R_1$, $R_3$, $R_4$, and $R_5$ are defined in the first aspect. Included in this embodiment are compounds in which $R_2$ is $C_{3-4}$ cycloalkyl. Also included in this embodiment are compounds in which $R_2$ is cyclopropyl.

One embodiment provides a compound of Formula (I) or a salt thereof, wherein $R_2$ is a cyclic group selected from piperidinyl, pyrazolyl, pyridinyl and indazolyl, each substituted with zero or one —CH$_3$; and X, Y, $R_1$, $R_3$, $R_4$, and $R_5$ are defined in the first aspect.

One embodiment provides a compound of Formula (I) or a salt thereof, wherein $R_2$ is —CHR$_{2a}$R$_{2b}$; and X, Y, $R_1$, $R_3$, $R_4$, $R_5$, $R_{2a}$, and $R_{2b}$ are defined in the first aspect. Included in this embodiment are compounds in which $R_{2b}$ is H, —CH$_3$, —CH$_2$OH, —CH(CH$_3$)OH, —CH$_2$OCH$_3$, or —CH$_2$OCF$_3$; and $R_{2a}$ is $C_{3-4}$ cycloalkyl, oxetanyl substituted with —CH$_2$NH$_2$, pyrazolyl, thiazolyl, pyridinyl, or phenyl substituted with zero to 2 substituents independently selected from F, —CN, —OH, —OCH$_3$, —OCHF$_2$, —C(CH$_3$)$_2$OH, and —NHC(O)CH$_3$. Also included in this embodiment are compounds in which $R_2$ is —CH(cyclopropyl)CH$_2$OH, —CH(phenyl)CH$_2$OH, —CH$_2$(thiazolyl), —CH(fluorophenyl)CH$_2$OH, or —CH$_2$(pyridinyl).

One embodiment provides a compound of Formula (I) or a salt thereof, wherein each $R_5$ is H, F, or $C_1$; and X, Y, $R_1$, $R_2$, $R_3$, and $R_4$ are defined in the first aspect. Included in this embodiment are compounds in which each $R_5$ is H or F; and compounds in which each $R_5$ is H. Also include in this embodiment are compounds in which Y is CF and the other $R_5$ groups are H.

One embodiment provides a compound of Formula (I) or a salt thereof, wherein X is N; Y is CR$_5$; $R_1$ is —C(O)OH, —C(O)O(C$_{1-3}$ alkyl), —C(O)NHR$_{1a}$, —NHC(O)R$_{1a}$, —C(O)NHNH$_2$, —C(O)NHNHC(O)R$_{1b}$, —C(O)NHNHC(=NCH$_2$CH$_3$(NH(CH$_2$)$_{2-4}$N(CH$_3$)$_2$), 1,8-dioxa-3-azaspiro[4.5]dec-2-enyl, a cyclic group selected from oxadiazolyl and pyrimidinyl, each substituted with zero to 2 $R_{1c}$; $R_{1a}$ is $C_{2-4}$ alkyl, —CH$_2$CH$_2$OCH$_3$, —CH$_2$C° CH, —(CH$_2$)$_{2-3}$N(CH$_3$)$_2$, pyrrolidinyl substituted with —CH$_2$(phenyl), —CH(CH$_3$)(phenyl), —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —CH$_2$CH$_2$CH$_2$(imidazolyl), —NHC(O)(cyclopropyl), —NHC(O)(pyrazinyl), —NHC(O)(pyridinyl), or cyclopropyl substituted with phenyl; $R_{1b}$ is —C(CH$_3$)$_2$OH, —C(CF$_3$)(CH$_3$)OH, cyclopropyl, pyridinyl, or pyrazinyl; $R_{1c}$ is $C_{1-4}$ alkyl, —C(CH$_3$)$_2$OH, —C(CH$_3$)$_2$CH$_2$CH$_2$CH$_2$OH, —C(CF$_3$)(CH$_3$)OH, =O, —CH$_2$(morpholinyl), difluorocyclobutyl, morpholinyl, tetrahydropyranyl, dioxotetrahydrothiopyranyl, fluorophenyl, pyridinyl, pyridazinyl, azabicyclo[2.2.2]octanyl, aminobicyclo[1.1.1]pentanyl, dimethylaminobicyclo[1.1.1]pentanyl, acetamidobicyclo[1.1.1]pentanyl, (methoxycarbonyl)aminobicyclo[1.1.1]pentanyl, cyclopropyl, trifluoromethylcyclopropyl, hydroxymethylcyclopropyl, or cyclopropyl substituted with —OC(O)(difluorazetidinyl); $R_2$ is —CH$_2$CH$_2$C(CH$_3$)$_2$NH$_2$, —CH$_2$C(CH$_3$)$_2$CH$_2$NH$_2$, —CH(phenyl)CH$_2$OH, —CH$_2$(hydroxypropylphenyl), or indazolyl; $R_3$ is —CH$_3$; $R_4$ is —CH$_3$; and each R$_5$ is independently H or F. Included in this embodiment are compounds in which each R$_5$ is H.

One embodiment provides a compound of Formula (I) or a salt thereof, wherein X is CH; Y is CR$_5$ or N; R$_1$ is oxadiazolyl substituted with R$_{1c}$; R$_{1c}$ is cyclopropyl, cyanocyclopropyl, azabicyclo[2.2.2]octanyl, or fluoroazabicyclo[2.2.2]octanyl; R$_2$ is —CH(cyclopropyl)CH$_2$OH, —CH(phenyl)CH$_2$OH, —CH(fluorophenyl)CH$_2$OH, —CH$_2$(thiazolyl), or —CH$_2$(pyridinyl); R$_3$ is —CH$_3$; R$_4$ is —CH$_3$; or R$_3$ and R$_4$ together with the carbon atom to which they are attached form a cyclopentyl ring; and each R$_5$ is independently H or F. Included in this embodiment are compounds in which R$_5$ is H.

One embodiment provides a compound of Formula (I) or a salt thereof, wherein R$_1$ is —C(O)OH, —C(O)O(C$_{1-3}$ alkyl), —C(O)NHR$_{1a}$, —C(O)NHNH$_2$, —C(O)NHNHC(O)R$_{1b}$, —C(O)NHNHC(=NCH$_2$CH$_3$(NH(CH$_2$)$_{2-4}$N(CH$_3$)$_2$), pyrimidinyl, 1,8-dioxa-3-azaspiro[4.5]dec-2-enyl, or a cyclic group selected from oxadiazolyl substituted with zero to 2 R$_{1c}$; R$_{1a}$ is C$_{2-4}$ alkyl, —CH$_2$CH$_2$OCH$_3$, —CH$_2$C≡CH, —(CH$_2$)$_{2-3}$N(CH$_3$)$_2$, =O, pyrrolidinyl substituted with —CH$_2$(phenyl), —CH(CH$_3$)(phenyl), —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —CH$_2$CH$_2$CH$_2$(imidazolyl), —NHC(O)(cyclopropyl), —NHC(O)(pyrazinyl), —NHC(O)(pyridinyl), or cyclopropyl substituted with phenyl; R$_{1b}$ is —C(CH$_3$)$_2$OH, —C(CF$_3$)(CH$_3$)OH, cyclopropyl, pyridinyl, or pyrazinyl; R$_{1c}$ is C$_{1-4}$ alkyl, —C(CH$_3$)$_2$H, —C(CH$_3$)$_2$CH$_2$CH$_2$OH, —C(CF$_3$)(CH$_3$)OH, =O, —CH$_2$(morpholinyl), cyclopropyl, trifluoromethylcyclopropyl, cyanocyclopropyl, hydroxymethylcyclopropyl, cyclopropyl substituted with —OC(O)(difluorazetidinyl), difluorocyclobutyl, morpholinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, or (methoxycarbonyl)aminobicyclo[1.1.1]pentanyl; R$_2$ is —CH$_2$C(CH$_3$)$_2$CH$_2$NH$_2$, —CH$_2$CH$_2$C(CH$_3$)$_2$NH$_2$, —CH$_2$(thiazolyl), —CH$_2$(pyridinyl), —CH(cyclopropyl)CH$_2$OH, —CH(phenyl)CH$_2$OH, —CH(fluorophenyl)CH$_2$OH, —CH$_2$(hydroxypropylphenyl), or indazolyl; and R$_3$, R$_4$, R$_5$, X, and Y defined in the first aspect. Included in this embodiment are compounds in which X is N and Y is CH or CF. Also included in this embodiment are compounds in which R$_2$ is —CH(phenyl)CH$_2$OH.

One embodiment provides a compound of Formula (I) or a salt thereof, wherein said compound is: 5-[(4'-{[(1S)-2-hydroxy-1-phenylethyl]amino}-[2,5'-bipyrimidine]-2'-yl)amino]-1,3-dihydro-2-benzofuran-1-one (1); ethyl 2-[(3,3-dimethyl-1-oxo-1,3-dihydro-2-benzofuran-5-yl)amino]-4-{[(1S)-2-hydroxy-1-phenylethyl]amino} pyrimidine-5-carboxylate (2); 2-[(3,3-dimethyl-1-oxo-1,3-dihydro-2-benzofuran-5-yl) amino]-4-{[(1S)-2-hydroxy-1-phenylethyl]amino}pyrimidine-5-carboxylic acid (3); N-[(3,3-difluorocyclobutyl) methyl]-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide (4); 2-[(3,3-dimethyl-1-oxo-1,3-dihydro-2-benzofuran-5-yl)amino]-N-[3-(dimethylamino) propyl]-4-{[(1S)-2-hydroxy-1-phenylethyl]amino}pyrimidine-5-carboxamide (5); 2-[(3,3-dimethyl-1-oxo-1,3-dihydro-2-benzofuran-5-yl)amino]-4-{[(1S)-2-hydroxy-1-phenylethyl]amino}-N-[(pyridin-2-yl)methyl]pyrimidine-5-carboxamide (6); 2-[(3,3-dimethyl-1-oxo-1,3-dihydro-2-benzofuran-5-yl)amino]-4-{[(1S)-2-hydroxy-1-phenylethyl]amino}-N-[3-(morpholin-4-yl)propyl]pyrimidine-5-carboxamide (7); 2-[(3,3-dimethyl-1-oxo-1,3-dihydro-2-benzofuran-5-yl)amino]-4-{[(1S)-2-hydroxy-1-phenylethyl]amino}-N-(2-methoxyethyl)pyrimidine-5-carboxamide (8); 2-[(3,3-dimethyl-1-oxo-1,3-dihydro-2-benzofuran-5-yl)amino]-N-[2-(dimethylamino)ethyl]-4-{[(1S)-2-hydroxy-1-phenylethyl]amino}pyrimidine-5-carboxamide (9); N-benzyl-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (10); N-tert-butyl-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide (11); 2-[(3,3-dimethyl-1-oxo-1,3-dihydro-2-benzofuran-5-yl)amino]-4-{[(1S)-2-hydroxy-1-phenylethyl]amino}-N-(2-methylpropyl) pyrimidine-5-carboxamide (12); 2-[(3,3-dimethyl-1-oxo-1,3-dihydro-2-benzofuran-5-yl)amino]-4-{[(1S)-2-hydroxy-1-phenylethyl]amino}-N-(propan-2-yl)pyrimidine-5-carboxamide (13); 2-[(3,3-dimethyl-1-oxo-1,3-dihydro-2-benzofuran-5-yl)amino]-4-{[(1S)-2-hydroxy-1-phenylethyl]amino}-N-propylpyrimidine-5-carboxamide (14); 2-[(3,3-dimethyl-1-oxo-1,3-dihydro-2-benzofuran-5-yl)amino]-4-{[(1S)-2-hydroxy-1-phenylethyl]amino}-N-(1-phenylethyl) pyrimidine-5-carboxamide (15); 2-[(3,3-dimethyl-1-oxo-1,3-dihydro-2-benzofuran-5-yl) amino]-4-{[(1S)-2-hydroxy-1-phenylethyl]amino}-N-[(2-methylphenyl)methyl] pyrimidine-5-carboxamide (16); 2-[(3,3-dimethyl-1-oxo-1,3-dihydro-2-benzofuran-5-yl) amino]-4-{[(1S)-2-hydroxy-1-phenylethyl]amino}-N-[(1S,2R)-2-phenylcyclopropyl] pyrimidine-5-carboxamide (17); 2-[(3,3-dimethyl-1-oxo-1,3-dihydro-2-benzofuran-5-yl) amino]-N-ethyl-4-{[(1S)-2-hydroxy-1-phenylethyl] amino}pyrimidine-5-carboxamide (18); 2-[(3,3-dimethyl-1-oxo-1,3-dihydro-2-benzofuran-5-yl)amino]-4-{[(1S)-2-hydroxy-1-phenylethyl]amino}-N-[3-(1H-imidazol-1-yl)propyl]pyrimidine-5-carboxamide (19); 2-[(3,3-dimethyl-1-oxo-1,3-dihydro-2-benzofuran-5-yl)amino]-4-{[(1S)-2-hydroxy-1-phenylethyl]amino}-N-[(5-methylpyrazin-2-yl)methyl]pyrimidine-5-carboxamide (20); 2-[(3,3-dimethyl-1-oxo-1,3-dihydro-2-benzofuran-5-yl)amino]-4-{[(1S)-2-hydroxy-1-phenylethyl]amino}-N-(prop-2-yn-1-yl) pyrimidine-5-carboxamide (21); N-(1-benzylpyrrolidin-3-yl)-2-[(3,3-dimethyl-1-oxo-1,3-dihydro-2-benzofuran-5-yl) amino]-4-{[(1S)-2-hydroxy-1-phenylethyl] amino}pyrimidine-5-carboxamide (22); 2-[(3,3-dimethyl-1-oxo-1,3-dihydro-2-benzofuran-5-yl)amino]-4-{[(1S)-2-hydroxy-1-phenylethyl]amino}-N-[(3-methyloxetan-3-yl) methyl]pyrimidine-5-carboxamide (23); 2-[(3,3-dimethyl-1-oxo-1,3-dihydro-2-benzofuran-5-yl)amino]-N-{[(3R)-3-hydroxy-1-azabicyclo[2.2.2]octan-3-yl]methyl}-4-{[(1S)-2-hydroxy-1-phenylethyl]amino}pyrimidine-5-carboxamide (24); N-({1-azabicyclo[2.2.2]octan-3-yl}methyl)-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (25); 2-[(3,3-dimethyl-1-oxo-1,3-dihydro-2-benzofuran-5-yl)amino]-4-{[(1S)-2-hydroxy-1-phenylethyl]amino}-N-({1-[(morpholin-4-yl)methyl]cyclopropyl}methyl)pyrimidine-5-carboxamide (26); 5-[(5-{1,8-dioxa-3-azaspiro[4.5]dec-2-en-2-yl}-4-{[(1S)-2-hydroxy-1-phenylethyl]amino} pyrimidin-2-yl)amino]-3,3-dimethyl-1,3-dihydro-2-benzofuran-1-one (27); 5-[(4-{[(1S)-2-hydroxy-1-phenylethyl] amino}-5-(3-methyl-1,2,4-oxadiazol-5-yl)pyrimidin-2-yl)amino]-3,3-dimethyl-1,3-dihydro-2-benzofuran-1-one (28); 5-{[5-(3-ethyl-1,2,4-oxadiazol-5-yl)-4-{[(1S)-2-hydroxy-1- phenylethyl]amino}pyrimidin-2-yl]amino}-3,3-dimethyl-1,3-dihydro-2-benzofuran-1-one (29); 5-{[5-(3-cyclopropyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (30); 5-[(4-{[(1S)-2-hydroxy-1-phenylethyl]amino}-5-[3-(morpholin-4-yl)-1,2,4-oxadiazol-5-yl]pyrimidin-2-yl)amino]-3,3-dimethyl-1,3-dihydro-2-benzofuran-1-one (31); 5-[(4-{[(1S)-2-hydroxy-1-phenylethyl]amino}-5-{3-[(morpholin-4-yl)methyl]-1,2,4-oxadiazol-5-yl}pyrimidin-2-yl)amino]-3,3-dimethyl-1,3-dihydro-2-benzofuran-1-one (32); 5-[(4-{[(1S)-2-hydroxy-1-phenylethyl]amino}-5-[3-(oxan-4-yl)-1,2,4-oxadiazol-5-yl]pyrimidin-2-yl)amino]-3,3-dimethyl-1,3-dihydro-2-benzofuran-1-one (33); 5-[(4-{[(1S)-2-hydroxy-1-phenylethyl]amino}-5-[3-(propan-2-yl)-1,2,4-oxadiazol-5-yl]pyrimidin-2-yl)amino]-3,3-dimethyl-1,3-dihydro-2-benzofuran-1-one (34); 5-[(4-{[(1S)-2-hydroxy-1-phenylethyl]amino}-5-(3-propyl-1,2,4-oxadiazol-5-yl)pyrimidin-2-yl)amino]-3,3-dimethyl-1,3-dihydro-2-benzofuran-1-one (35); 5-{[5-(3-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (36); 5-[(4-{[(1S)-2-hydroxy-1-phenylethyl]amino}-5-[3-(6-hydroxy-2-methylhexan-2-yl)-1,2,4-oxadiazol-5-yl]pyrimidin-2-yl)amino]-3,3-dimethyl-1,3-dihydro-2-benzofuran-1-one (37); 5-[(4-{[(1S)-2-hydroxy-1-phenylethyl]amino}-5-{3-[1-(hydroxymethyl)cyclopropyl]-1,2,4-oxadiazol-5-yl}pyrimidin-2-yl)amino]-3,3-dimethyl-1,3-dihydro-2-benzofuran-1-one (38); 5-{[5-(3-tert-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (39); 5-({5-[3-(3,3-difluorocyclobutyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one (40); (S)-5-((4-((2-hydroxy-1-phenylethyl)amino)-5-(3-(1-hydroxy-2-methylpropan-2-yl)-1,2,4-oxadiazol-5-yl)pyrimidin-2-yl)amino)-3,3-dimethylisobenzofuran-1(3H)-one (41); 5-[(4-{[(1S)-2-hydroxy-1-phenylethyl]amino}-5-[3-(pyridin-2-yl)-1,2,4-oxadiazol-5-yl]pyrimidin-2-yl) amino]-3,3-dimethyl-1,3-dihydro-2-benzofuran-1-one (42); 5-[(4-{[(1S)-2-hydroxy-1-phenylethyl]amino}-5-[3-(pyridin-3-yl)-1,2,4-oxadiazol-5-yl]pyrimidin-2-yl)amino]-3,3-dimethyl-1,3-dihydro-2-benzofuran-1-one (43); 5-({5-[3-(4-fluorophenyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one (44); 5-({5-[3-(3-fluorophenyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one (45); 5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (47); 5-[(5-{3-[3-(dimethylamino) bicyclo[1.1.1]pentan-1-yl]-1,2,4-oxadiazol-5-yl}-4-{[(1S)-2-hydroxy-1-phenylethyl]amino}pyrimidin-2-yl)amino]-3,3-dimethyl-1,3-dihydro-2-benzofuran-1-one (48); N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl)bicyclo[1.1.1] pentan-1-yl]acetamide (49); methyl N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl) bicyclo[1.1.1] pentan-1-yl]carbamate (50); 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (51); 5-{2-[(3,3-dimethyl-1-oxo-1,3-dihydro-2-benzofuran-5-yl) amino]-4-{[(1S)-2-hydroxy-1-phenylethyl]amino}pyrimidin-5-yl}-2,3-dihydro-1,3,4-oxadiazol-2-one (52); 5-{2-[(3,3-dimethyl-1-oxo-1,3-dihydro-2-benzofuran-5-yl) amino]-4-{[(1S)-2-hydroxy-1-phenylethyl]amino}pyrimidin-5-yl}-3-ethyl-2,3-dihydro-1,3,4-oxadiazol-2-one (53); 5-[(4-{[(1S)-2-hydroxy-1-phenylethyl]amino}-5-(1,3,4-oxadiazol-2-yl) pyrimidin-2-yl)amino]-3,3-dimethyl-1,3-dihydro-2-benzofuran-1-one (54); 5-[(4- {[(1S)-2-hydroxy-1-phenylethyl]amino}-5-(5-methyl-1,3,4-oxadiazol-2-yl) pyrimidin-2-yl) amino]-3,3-dimethyl-1,3-dihydro-2-benzofuran-1-one (55); N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide (56); 5-[(4-{[(1S)-2-hydroxy-1-phenylethyl]amino}-5-[5-(pyridin-3-yl)-1,3,4-oxadiazol-2-yl]pyrimidin-2-yl)amino]-3,3-dimethyl-1,3-dihydro-2-benzofuran-1-one (57); N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyrazine-2-carbohydrazide (58); 1-({2-[(3,3-dimethyl-1-oxo-1,3-dihydro-2-benzofuran-5-yl)amino]-4- {[(1S)-2-hydroxy-1-phenylethyl]amino}pyrimidin-5-yl}formohydrazido)-N-[3-(dimethylamino)propyl]-N'-ethylmethanimidamide (59); 2-[(3,3-dimethyl-1-oxo-1,3-dihydro-2-benzofuran-5-yl)amino]-4-{[(1S)-2-hydroxy-1-phenylethyl]amino}-N'-(2-hydroxy-2-methylpropanoyl)pyrimidine-5-carbohydrazide (60); 5-[(4-{[(1S)-2-hydroxy-1-phenylethyl]amino}-5-[5-(2-hydroxypropan-2-yl)-1,3,4-oxadiazol-2-yl]pyrimidin-2-yl)amino]-3,3-dimethyl-1,3-dihydro-2-benzofuran-1-one (61); (S)—N'-(cyclopropanecarbonyl)-2-((3,3-dimethyl-1-oxo-1,3-dihydroisobenzofuran-5-yl)amino)-4-((2-hydroxy-1-phenylethyl)amino)pyrimidine-5-carbohydrazide (62); 5-{[5-(5-cyclopropyl-1,3,4-oxadiazol-2-yl)-4-{[(1S)-2-hydroxy-1-phenylethyl]amino}pyrimidin-2-yl]amino}-3,3-dimethyl-1,3-dihydro-2-benzofuran-1-one (63); 2-[(3,3-dimethyl-1-oxo-1,3-dihydro-2-benzofuran-5-yl)amino]-4-{[(1S)-2-hydroxy-1-phenylethyl]amino}-N'-(3,3,3-trifluoro-2-hydroxy-2-methylpropanoyl)pyrimidine-5-carbohydrazide (64); 5-[(4-{[(1S)-2-hydroxy-1-phenylethyl]amino}-5-[5-(1,1,1-trifluoro-2-hydroxypropan-2-yl)-1,3,4-oxadiazol-2-yl]pyrimidin-2-yl)amino]-3,3-dimethyl-1,3-dihydro-2-benzofuran-1-one (65); 5-[(4-{[(1S)-2-hydroxy-1-phenylethyl]amino}-5-[5-(pyridin-2-yl)-1,3,4-oxadiazol-2-yl]pyrimidin-2-yl)amino]-3,3-dimethyl-1,3-dihydro-2-benzofuran-1-one (66); 5-[(4-{[(1S)-2-hydroxy-1-phenylethyl]amino}-5-[5-(pyridazin-3-yl)-1,3,4-oxadiazol-2-yl]pyrimidin-2-yl)amino]-3,3-dimethyl-1,3-dihydro-2-benzofuran-1-one (67); 5-[(4-{[(1S)-2-hydroxy-1-phenylethyl]amino}-5-{5-[1-(trifluoromethyl) cyclopropyl]-1,3,4-oxadiazol-2-yl}pyrimidin-2-yl)amino]-3,3-dimethyl-1,3-dihydro-2-benzofuran-1-one (68); (S)-5-((5-(5-(1,1-dioxidotetrahydro-2H-thiopyran-4-yl)-1,3,4-oxadiazol-2-yl)-4-((2-hydroxy-1-phenylethyl)amino) pyrimidin-2-yl)amino)-3,3-dimethylisobenzofuran-1(3H)-one (69); 1-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,3,4-oxadiazol-2-yl) cyclopropyl 3,3-difluoroazetidine-1-carboxylate (70); ethyl 2-[(3,3-dimethyl-1-oxo-1,3-dihydro-2-benzofuran-5-yl) amino]-4-({[2-(2-hydroxypropan-2-yl) phenyl] methyl}amino)pyrimidine-5-carboxylate (71); 5-{[4-({[2-(2-hydroxypropan-2-yl) phenyl]methyl}amino)-5-(3-methyl-1,2,4-oxadiazol-5-yl)pyrimidin-2-yl]amino}-3,3-dimethyl-1,3-dihydro-2-benzofuran-1-one (72); 5-{[5-(3-cyclopropyl-1,2,4-oxadiazol-5-yl)-4-({[2-(2-hydroxypropan-2-yl)phenyl]methyl}amino)pyrimidin-2-yl amino}-3,3-dimethyl-1,3-dihydro-2-benzofuran-1-one (73); 5-({4-[(1H-indazol-5-yl)amino]-5-(3-methyl-1,2,4-oxadiazol-5-yl)pyrimidin-2-yl}amino)-3,3-dimethyl-1,3-dihydro-2-benzofuran-1-one (74); 5-{[5-(3-cyclopropyl-1,2,4-oxadiazol-5-yl)-4-[(1H-indazol-5-yl) amino]pyrimidin-2-yl] amino}-3,3-dimethyl-1,3-dihydro-2-benzofuran-1-one (75); ethyl 4-[(3-amino-3-methylbutyl)amino]-2-[(3,3-dimethyl-1-oxo-1,3-dihydro-2-benzofuran-5-yl)amino]pyrimidine-5-carboxylate (76); 5-({4-[(3-amino-2,2-dimethylpropyl) amino]-5-[3-(oxan-4-yl)-1,2,4-oxadiazol-5-yl]pyrimidin-2-yl}amino)-3,3-dimethyl-1,3-dihydro-2-benzofuran-1-one (77); or 5-{[5-(3-{1-azabicyclo[2.2.2]octan-4-yl}-1,2,4-oxadiazol-5-yl)-4-{[(1S)-2-hydroxy-1-phenylethyl] amino}pyrimidin-2-yl]amino}-3,3-dimethyl-1,3-dihydro-2-benzofuran-1-one (80).

One embodiment provides a compound of Formula (I) or a salt thereof, wherein said compound is: 5-{[5-(3-{1-azabicyclo[2.2.2]octan-4-yl}-1,2,4-oxadiazol-5-yl)-4-{ [(1S)-2-hydroxy-1-phenylethyl] amino}pyridin-2-yl] amino}-3,3-dimethyl-1,3-dihydro-2-benzofuran-1-one (46); 5-{[5-(3-cyclopropyl-1,2,4-oxadiazol-5-yl)-4-{[(1S)-2-hydroxy-1-phenylethyl] amino}pyridin-2-yl]amino}-3,3-dimethyl-1,3-dihydro-2-benzofuran-1-one (78); 5-{[5-(3-cyclopropyl-1,2,4-oxadiazol-5-yl)-4-{[(1S)-1-cyclopropyl-2-hydroxyethyl]amino} pyridin-2-yl]amino}-3,3-dimethyl-1, 3-dihydro-2-benzofuran-1-one (79); 2-{[5-(3-{1-azabicyclo [2.2.2]octan-4-yl}-1,2,4-oxadiazol-5-yl)-4-{[(1S)-2-hydroxy-1-phenylethyl] amino}pyridin-2-yl]amino}-7,7-dimethyl-5H,7H-furo[3,4-b]pyridin-5-one (81); 2-{[5-(3-{1-azabicyclo[2.2.2]octan-4-yl}-1,2,4-oxadiazol-5-yl)-4-{[(1S)-1-(4-fluorophenyl)-2-hydroxyethyl]amino}pyridin-2-yl]amino}-7,7-dimethyl-5H,7H-furo[3,4-b]pyridin-5-one (82); 2-{[5-(3-{4-fluoro-1-azabicyclo[2.2.2]octan-3-yl}-1, 2,4-oxadiazol-5-yl)-4-{[(1S)-2-hydroxy-1-phenylethyl] amino}pyridin-2-yl]amino}-7,7-dimethyl-5H,7H-furo[3,4-b] pyridin-5-one (83); 2-{[5-(3-{1-azabicyclo [2.2.2]octan-4-yl}-1,2,4-oxadiazol-5-yl)-4-{[(1,3-thiazol-2-yl)methyl] amino}pyridin-2-yl]amino}-7,7-dimethyl-5H,7H-furo[3,4-b] pyridin-5-one (84); 2-{[5-(3-{1-azabicyclo [2.2.2]octan-4-yl}-1,2,4-oxadiazol-5-yl)-4-{[(pyridin-3-yl)methyl] amino}pyridin-2-yl]amino}-7,7-dimethyl-5H,7H-furo[3,4-b] pyridin-5-one (85); 2-{[5-(5-cyclopropyl-1,3,4-oxadiazol-2-yl)-4-{[(1S)-2-hydroxy-1-phenylethyl] amino}pyridin-2-yl]amino}-7,7-dimethyl-5H,7H-furo[3,4-b]pyridin-5-one (86); 2'-{[5-(3-cyclopropyl-1,2,4-oxadiazol-5-yl)-4-{[(1S)-2-hydroxy-1-phenylethyl] amino}pyridin-2-yl]amino}-5'H-spiro [cyclopentane-1,7'-furo[3,4-b]pyridine]-5'-one (87); or 1-{5-[6-({7,7-dimethyl-5-oxo-5H,7H-furo[3,4-b]pyridin-2-yl}amino)-4-{[(1S)-2-hydroxy-1-phenylethyl]amino}pyridin-3-yl]-1,3,4-oxadiazol-2-yl}cyclopropane-1-carbonitrile (88).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —$CHFCH_2OH$, —$CH_2CHFC(CH_3)_2OH$, and $C_{1-4}$ hydroxy-fluoroalkyl.

The term "cycloalkyl," as used herein, refers to a group derived from a non-aromatic monocyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "bicycloalkyl," as used herein, refers to a group derived from a non-aromatic bicyclic hydrocarbon molecule by removal of one hydrogen atom from a saturated ring carbon atom. Representative examples of bicycloalkyl groups include, but are not limited to, bicyclo[1.1.1]pentanyl, bicyclo[2.1.1]hexane, bicyclo[2.2.1]heptane, and bicyclo[2.2.2]octanyl. When numbers appear in a subscript after the symbol "C", the subscript defines with more specificity the number of carbon atoms that a particular cycloalkyl group may contain. For example, "$C_{5-8}$ bicycloalkyl" denotes bicycloalkyl groups with five to eight carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "benzyl", as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The term "heterocyclo", "heterocyclic", or "heterocyclyl" may be used interchangeably and refer to cyclic groups having at least one saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary 4- to 7-membered monocyclic heterocyclyl groups include oxetanyl, tetrahydrofuranyl, pyrrolidinyl, pyrazolinyl, imidazolinyl, oxazolidinyl, isoxazolinyl, thiazolidinyl, isothiazolidinyl, tetrahydropyranyl, morpholinyl, piperidinyl, piperazinyl, azepinyl, and thiamorpholinyl.

The term "bicyclic nitrogen containing heterocyclyl," as used herein, refers to a group derived from a non-aromatic bicyclic nitrogen containing heterocyclyl molecule by removal of one hydrogen atom from a saturated ring atom. The bicyclic nitrogen containing heterocyclyl includes one or more nitrogen heteroatoms. Representative examples of bicyclic nitrogen containing heterocyclyl groups include, but are not limited to, azabicyclo[1.1.1]pentane, azabicyclo[2.1.1]hexane, azabicyclo[2.2.1]heptane, and azabicyclo[2.2.2]octanyl.

The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s)" may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, β-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding.

In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of HPK1, or effective to treat or prevent viral infections and proliferative disorders, such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof, and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the compound of Formula (I) may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compounds of Formula (I) are useful for the treatment of cancer.

In another embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with HPK1 target inhibition in T cells.

In another aspect, the invention provides a method of treating a patient suffering from or susceptible to a medical condition that is associated with HPK1 target inhibition in T cells. A number of medical conditions can be treated. The method comprises administering to the patient a therapeutically effective amount of a composition comprising a compound of Formula (I) and/or a pharmaceutically acceptable salt thereof, a stereoisomer thereof or a tautomer thereof. For example, the compounds described herein may be used to treat or prevent viral infections and proliferative diseases such as cancer.

The compounds for Formula (I) and pharmaceutical compositions comprising at least one compound of Formula (I) are useful in treating or preventing any disease or conditions that are associated with HPK1 target inhibition in T cells. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can inhibit activity of the hematopoietic progenitor kinase 1 (HPK). For example, the compounds of Formula (I) can be used to inhibit activity of HPK1 in a cell or in an individual in need of modulation of the HPK1 by administering an inhibiting amount of a compound of Formula (I) or a salt thereof.

The present invention further provides methods of treating diseases associated with activity or expression, including abnormal activity and/or overexpression, of HPK1 in an individual (e.g., patient) by administering to the individual in need of such treatment a therapeutically effective amount or dose of a compound of Formula (I) or a pharmaceutical composition thereof. Example diseases can include any disease, disorder or condition that is directly or indirectly linked to expression or activity of the HPK1 enzyme, such as over expression or abnormal activity. An HPK1-associated disease can also include any disease, disorder or condition that can be prevented, ameliorated, or cured by modulating HPK1 enzyme activity. Examples of HPK1 associated diseases include cancer and viral infections such as HIV infection, hepatitis B, and hepatitis C.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the HPK1 enzyme with a compound of Formula (I) includes the administration of a compound of the present invention to an individual or patient, such as a human, having HPK1, as well as, for example, introducing a compound of Formula (I) into a sample containing a cellular or purified preparation containing the HPK1 enzyme.

The term "HPKT inhibitor" refers to an agent capable of inhibiting the activity of hematopoietic progenitor kinase 1 (HPK) in T cells resulting in T cell stimulation. The HPKT inhibitor may be a reversible or irreversible HPK1 inhibitor. "A reversible HPK1 inhibitor" is a compound that reversibly inhibits HPK1 enzyme activity either at the catalytic site or at a non-catalytic site and "an irreversible HPK1 inhibitor" is a compound that irreversibly destroys HPK1 enzyme activity by forming a covalent bond with the enzyme.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of HPK1 associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-$\alpha$), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-$\beta$).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as famesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-O1 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J. Biol. Chem., 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of HPK1-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The invention also provides pharmaceutically acceptable compositions which comprise a therapeutically effective amount of one or more of the compounds of Formula (I), formulated together with one or more pharmaceutically acceptable carriers (additives) and/or diluents, and optionally, one or more additional therapeutic agents described above.

The compounds of Formula (I) can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of Formula (I) may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of Formula (I) (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of Formula (I) (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of Formula (I), alone or in combination with a pharmaceutical carrier. Optionally, compounds of Formula (I) can be used alone, in combination with other compounds of Formula (I), or in combination with one or more other therapeutic agent(s), e.g., an anticancer agent or other pharmaceutically active material.

Regardless of the route of administration selected, the compounds of Formula (I), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of Formula (I) employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I) employed in the pharmaceutical composition at levels lower than that required in order to achieve the desired therapeutic effect and gradually increase the dosage until the desired effect is achieved.

In general, a suitable daily dose of a compound of Formula (I) will be that amount of the compound which is the lowest dose effective to produce a therapeutic effect. Such an effective dose will generally depend upon the factors described above. Generally, oral, intravenous, intracerebroventricular and subcutaneous doses of the compounds of Formula (I) for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of Formula (I) to be administered alone, it is preferable to administer the compound as a pharmaceutical formulation (composition).

The above other therapeutic agents, when employed in combination with the compounds of Formula (I), may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

Abbreviations

CSA camphorsulfonic acid
DCC N,N'-dicyclohexyl carbodiimide
DCM dichloromethane
DIPEA N,N-diisopropylethylamine
DMA N,N-dimethylacetamide
DMF N,N-dimethylformamide
DMSO dimethyl sulfoxide
EDC 1-ethyl-3-(3-dimethylaminopropyl)carbodiimide
EtOAc ethyl acetate
EtOH ethanol
h hour(s)
HATU 1-[bis(dimethylamino)methylene]-1H-1,2,3-triazolo[4,5-b]pyridinium 3-oxide hexafluorophosphate
HCl hydrochloric acid
HOBt N-Hydroxybenzotriazole
HPLC high performance liquid chromatography
Hünig's base N,N-diisopropylethylamine
$MgSO_4$ magnesium sulfate
min minutes
NaOH sodium hydroxide
$Na_2SO_4$ sodium sulfate
$NH_4Cl$ ammonium chloride
NMP N-methylpyrrolidinone
OTBS tert-butyldimethylsilyl)oxy
$PdCl_2(dppf)$-$CH_2Cl_2$ [1,1'-bis(diphenylphosphino)ferrocene]dichloropalladium(II), complex with dichloromethane
$Pd_2(dba)_3$ tris(dibenzylideneacetone)dipalladium(0)
$Pd(Ph_3P)_4$ tetrakis(triphenylphosphine)palladium(0)
$t_R$ retention time
TBAF tetrabutylammonium fluoride
THF tetrahydrofuran
Xantphos 4,5-bis(diphenylphosphino)-9,9 dimethyl xanthene LC/MS Conditions:

LC/MS Condition 1: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

LC/MS Condition 2: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1.0 mL/min; Detection: MS and UV at 220 nm.

LC/MS Condition 3: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1.0 mL/min; Detection: MS and UV at 220 nm.

LC/MS Condition 4: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 min, then a 2 min hold at 100% B; Flow: 0.75 mL/min; Detection: MS and UV at 220 nm.

LC/MS Condition 5: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 min, then a 2 min hold at 100% B; Flow: 0.75 mL/min; Detection: MS and UV at 220 nm.

Example 1

5-[(4'-{[(1S)-2-hydroxy-1-phenylethyl]amino}-[2,5'-bipyrimidine]-2'-yl)amino]-1,3-dihydro-2-benzofuran-1-one

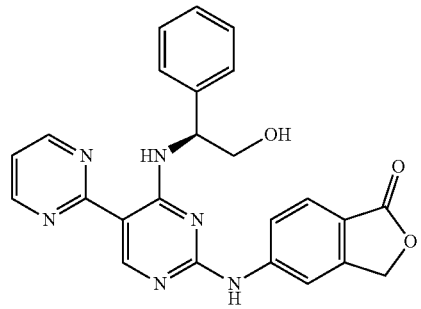

(1)

Preparation 1A: (S)—N-(2-((tert-butyldimethylsilyl)oxy)-1-phenylethyl)-2-chloro-5-iodo pyrimidin-4-amine

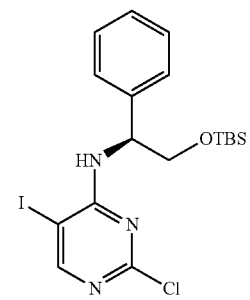

(1A)

To a solution of 2,4-dichloro-5-iodopyrimidine (1.00 g, 3.64 mmol) in 2-propanol (20 mL) was added (S)-2-((tert-butyldimethylsilyl)oxy)-1-phenylethanamine (0.915 g, 3.64 mmol), followed by DIPEA (1.27 mL, 7.28 mmol). The reaction mixture was stirred at room temperature for 48 h. The volatiles were removed under reduced pressure and the residue was then dissolved in DCM, washed with water, brine, then dried over $Na_2SO_4$. The organic layer was then filtered and concentrated under reduced pressure to afford the crude product which was purified via silica gel chromatography eluting with a gradient from 0 to 15% EtOAc in hexanes to afford (S)—N-(2-((tert-butyldimethylsilyl)oxy)-1-phenylethyl)-2-chloro-5-iodo pyrimidin-4-amine (1.51 g, 3.08 mmol, 85% yield) as a white solid. ES [MS] m/z: 490.1 [M+H]$^+$. $^1$H NMR (500 MHz, CDCl$_3$) δ 8.38-8.11 (m, 1H), 7.42-7.25 (m, 5H), 6.64-6.46 (m, 1H), 5.36-5.23 (m, 1H), 4.11-3.97 (m, 1H), 3.95-3.79 (m, 1H), 0.91 (s, 10H), 0.11-0.13 (m, 6H).

Preparation 1B: (S)—N-(2-((tert-butyldimethylsilyl) oxy)-1-phenylethyl)-2'-chloro-[2,5'-bipyrimidin]-4'-amine

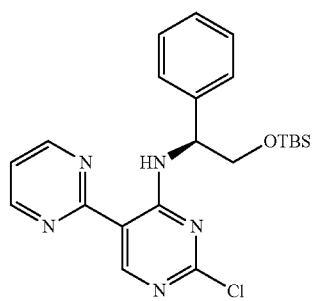

(1B)

An oven dried microwave vial charged with (S)—N-(2-((tert-butyldimethylsilyl) oxy)-1-phenylethyl)-2-chloro-5-iodopyrimidin-4-amine (500 mg, 1.021 mmol), copper (I) iodide (38.9 mg, 0.204 mmol), and Pd(Ph₃P)₄ (118 mg, 0.102 mmol) was purged with nitrogen (g). 1,4-Dioxane (10 mL) and 2-(tributylstannyl)pyrimidine (500 mg, 1.35 mmol) were added and the vessel was again purged with nitrogen. The reaction mixture was heated in a microwave reactor at 130° C. for 0.5 h, followed by heating in an oil bath at 100° C. for 1 h. The reaction mixture was cooled to room temperature then diluted with EtOAc and washed with water. The layers were separated and the aqueous phase was extracted with EtOAc. The combined organic layers were washed with brine, dried over Na₂SO₄, filtered and concentrate under reduced pressure. The crude product was purified via silica gel chromatography, eluting with a gradient from 0 to 25% EtOAc in hexanes. (S)—N-(2-((tert-butyldimethylsilyl)oxy)-1-phenylethyl)-2'-chloro-[2,5'-bipyrimidin]-4'-amine (375 mg, 0.848 mmol) was obtained as a syrup. ES [MS] m/z: 442.9 [M+H]⁺. ¹H NMR (500 MHz, CDCl₃) δ 10.64 (br d, J=8.1 Hz, 1H), 9.48-9.21 (m, 1H), 8.87-8.75 (m, 2H), 7.52-7.18 (m, 7H), 5.68-5.51 (m, 1H), 4.17-4.01 (m, 1H), 3.99-3.91 (m, 1H), 0.92-0.81 (m, 9H), 0.05-0.18 (m, 6H).

Example 1

CSA (18.92 mg, 0.081 mmol) was added to a mixture of (S)—N-(2-((tert-butyldimethylsilyl)oxy)-1-phenylethyl)-2'-chloro-[2,5'-bipyrimidin]-4'-amine (24 mg, 0.054 mmol) and 5-aminoisobenzofuran-1(3H)-one (8.10 mg, 0.054 mmol) in N-methyl-2-pyrrolidinone (0.2 mL) in a 1 dram vial. The vial was capped, sealed and heated to 110° C. overnight. The reaction mixture was diluted with DMF and filtered prior to purifying the crude material via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 20 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the product were combined and dried via centrifugal evaporation. HPLC t_R: 1.61 min; LC/MS Condition 1. ES [MS] m/z: 441.1 [M+H]⁺. ¹H NMR (500 MHz, DMSO-d₆) δ 10.78 (br d, J=7.0 Hz, 1H), 10.28 (s, 1H), 9.21 (s, 1H), 8.92 (d, J=4.8 Hz, 2H), 7.93 (s, 1H), 7.70-7.64 (m, 2H), 7.45-7.35 (m, 5H), 7.26-7.20 (m, 1H), 5.44 (d, J=15.4 Hz, 1H), 5.36 (br d, J=5.1 Hz, 1H), 5.27 (d, J=15.4 Hz, 1H), 3.90 (dd, J=11.0, 4.0 Hz, 1H), 3.79 (dd, J=10.8, 5.7 Hz, 1H), 2.54 (s, 1H).

Example 2

Ethyl 2-[(3,3-dimethyl-1-oxo-1,3-dihydro-2-benzofuran-5-yl)amino]-4-{[(1S)-2-hydroxy-1-phenylethyl]amino}pyrimidine-5-carboxylate

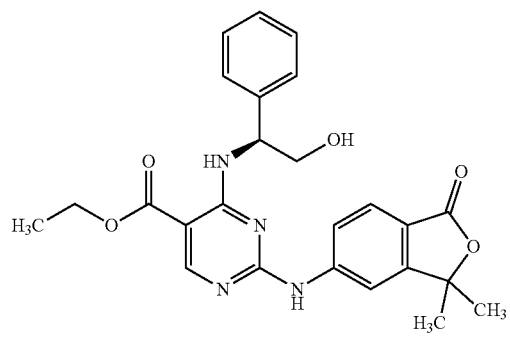

(2)

Preparation 2A: (S)-ethyl 2-chloro-4-((2-hydroxy-1-phenylethyl)amino)pyrimidine-5-carboxylate

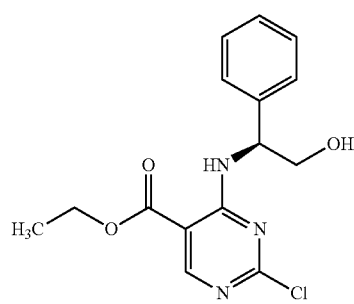

(2A)

To a 200 mL round bottom flask equipped with a stir bar and charged with a solution of ethyl 2,4-dichloropyrimidine-5-carboxylate (6.00 g, 27.1 mmol) in acetonitrile (80 mL) was added Hünig's base (9.46 mL, 54.3 mmol) followed by (S)-2-amino-2-phenylethanol (3.91 g, 28.5 mmol). The resulting mixture was stirred at room temperature for 3 h. The reaction mixture was concentrated under reduced pressure and purified using silica gel chromatography eluting with a gradient from 0 to 50% EtOAc in hexanes to afford (S)-ethyl 2-chloro-4-((2-hydroxy-1-phenylethyl)amino)pyrimidine-5-carboxylate (8.57 g, 26.6 mmol, 98% yield), as a white solid. ES [MS] m/z: 321.9 [M+H]+. 1H NMR (400 MHz, CDCl3) δ 9.18 (br d, J=7.8 Hz, 1H), 8.72 (s, 1H), 7.45-7.39 (m, 4H), 7.38-7.32 (m, 1H), 5.51 (dt, J=8.0, 4.9 Hz, 1H), 4.47-4.35 (m, 2H), 4.07-3.96 (m, 2H), 2.06 (br d, J=7.5 Hz, 1H), 1.42 (t, J=7.2 Hz, 3H).

Preparation 2B:
4-amino-2-(prop-1-en-2-yl)benzonitrile

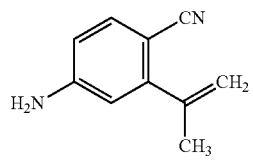

(2B)

To a 500 mL round-bottomed flask were added 4-amino-2-bromobenzonitrile (7.00 g, 35.5 mmol), 4,4,5,5-tetramethyl-2-(prop-1-en-2-yl)-1,3,2-dioxaborolane (6.87 g, 40.9 mmol), potassium carbonate (9.82 g, 71.1 mmol), followed by 1,4-dioxane (90 mL), water (45 mL) and PdCl2(dppf)-CH2Cl2 (0.087 g, 0.107 mmol). Argon was bubbled through the suspension and the flask was sealed and heated at 80° C. overnight. The reaction mixture was diluted with EtOAc, washed with brine and the organic layer was separated, dried over sodium sulfate, filtered and concentrated. The crude material was purified by silica gel chromatography eluting with a gradient from 0 to 50% of a 10% solution of 2 N ammonia in methanol in ethyl acetate in DCM to afford 4-amino-2-(prop-1-en-2-yl)benzonitrile (5.23 g, 33.1 mmol, 93% yield). ES [MS] m/z: 159.12 [M+H]+. 1H NMR (400 MHz, CDCl3) δ 7.47-7.42 (m, 1H), 6.58 (dq, J=4.5, 2.4 Hz, 2H), 5.33 (quin, J=1.4 Hz, 1H), 5.26-5.22 (m, 1H), 4.22-4.09 (m, 2H), 2.17 (dd, J=1.5, 1.0 Hz, 3H), 1.31-1.29 (m, 2H).

Preparation 2C:
4-amino-2-(2-hydroxypropan-2-yl)benzonitrile

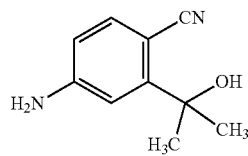

(2C)

To a 500 mL round bottom flask were added 4-amino-2-(prop-1-en-2-yl) benzonitrile (5.00 g, 31.6 mmol), DCM (10 mL), 2-propanol (200 mL), phenylsilane (6.84 g, 63.2 mmol) and tris(2,2,6,6-tetramethyl-3,5-heptanedionato) manganese(III) (1.91 g, 3.16 mmol). The reaction flask was cooled to 0° C. with an ice bath. Air was evacuated from the flask and the reaction mixture was stirred under an atmosphere of oxygen (balloon). After 2 hours, the reaction was quenched with a 20% aqueous solution of sodium thiosulfate and the mixture was extracted with EtOAc. The combined organic layers were washed with brine, dried over MgSO4, filtered and concentrated. ES [MS]m/z: 177.0 [M+H]+.

Preparation 2D:
5-amino-3,3-dimethylisobenzofuran-1(3H)-one

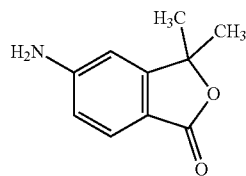

(2D)

To a 200 mL round bottom flask was added 4-amino-2-(2-hydroxypropan-2-yl) benzonitrile (5.57 g, 31.6 mmol), DMF (60 mL), and water (60 mL), followed by the addition of solid NaHCO3 (10.6 g, 126 mmol). The reaction flask was heated to 80° C. After 24 hours, the reaction mixture was filtered through a pad of Celite which was rinsed with EtOAc. The mixture was further diluted with EtOAc and was washed three times with brine. The organic layer was separated, dried over MgSO4, filtered, and concentrated. The crude material was purified by silica gel chromatography eluting with a gradient from 0 to 50% of a 10% solution of 2 N ammonia in methanol in ethyl acetate in DCM to afford 5-amino-3,3-dimethylisobenzofuran-1(3H)-one (4.77 g, 26.9 mmol, 85% yield). ES [MS] m/z: 178.1 [M+H]+. 1H NMR (400 MHz, CDCl3) δ 7.64 (d, J=8.3 Hz, 1H), 6.71 (dd, J=8.3, 2.0 Hz, 1H), 6.54 (d, J=1.8 Hz, 1H), 4.28 (br. s., 2H), 1.62 (s, 6H).

Example 2

(S)-Ethyl 2-chloro-4-((2-hydroxy-1-phenylethyl)amino) pyrimidine-5-carboxylate (23.01 mg, 0.072 mmol) and 4-amino-2-(2-hydroxypropan-2-yl)benzonitrile (12.0 mg, 0.068 mmol) were dissolved in N-methyl-2-pyrrolidinone (1 mL) in a one dram pressure vial. To this was added a 4 M solution of HCl in dioxane (0.102 mL, 0.102 mmol) and the resulting mixture was heated to 80° C. overnight. LC/MS confirmed formation of the desired compound. The filtered reaction mixture was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-67% B over 20 minutes, then a 5-minute hold at 100% B; Flow: 20 mL/min. Fractions containing the product were combined and dried via centrifugal evaporation to afford ethyl 2-[(3,3-dimethyl-1-oxo-1,3-dihydro-2-benzofuran-5-yl)amino]-4-{[(1S)-2-hydroxy-1-phenylethyl]amino}pyrimidine-5-carboxylate (2.1 mg, 6% yield). HPLC tR: 1.88 min; LC/MS Condition 2. ES [MS]+m/z: 463 [M+H]+. 1H NMR (500 MHz, DMSO-d6) δ 10.14 (s, 1H), 8.94 (d, J=7.7 Hz, 1H), 8.68 (s, 1H), 7.96 (s, 1H), 7.72 (d, J=8.4 Hz, 1H), 7.63 (d, J=8.8 Hz, 1H), 7.42-7.34 (m, 4H), 7.28 (d, J=7.0 Hz, 1H), 5.35 (d, J=7.0 Hz, 1H), 5.07 (t, J=5.0 Hz, 1H), 4.34 (q, J=6.8 Hz, 2H), 3.92-3.87 (m, 1H), 3.85-3.79 (m, 1H), 1.59 (s, 3H), 1.55 (s, 3H), 1.36 (t, J=7.2 Hz, 3H).

Example 3

2-[(3,3-dimethyl-1-oxo-1,3-dihydro-2-benzofuran-5-yl)amino]-4-{[(1S)-2-hydroxy-1-phenylethyl]amino}pyrimidine-5-carboxylic acid

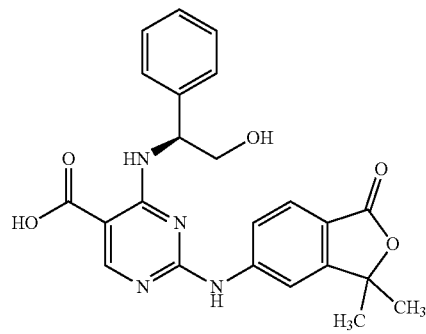

(3)

To a vial charged with a solution of (S)-ethyl 2-((3,3-dimethyl-1-oxo-1,3-dihydroisobenzofuran-5-yl)amino)-4-((2-hydroxy-1-phenylethyl)amino)pyrimidine-5-carboxylate (19.0 mg, 0.041 mmol) dissolved in THF (6 mL) and water (3 mL) was added lithium hydroxide (2.0 mg, 0.082 mmol). The resulting mixture was stirred at room temperature for 2 h. An additional 4 equivalents of lithium hydroxide were added and stirring continued overnight. LCMS analysis indicated consumption of the starting material. The solution was neutralized to pH ~6 using a 2N aqueous solution of HCl. The product was extracted with EtOAc (3×25 mL), and the combined organic phases were dried over MgSO$_4$, filtered and concentrated to afford Example 3. The product was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 18 minutes, then a 4-minute hold at 100% B; Flow: 20 mL/min. Fractions containing the product were combined and dried via centrifugal evaporation to afford 2-[(3,3-dimethyl-1-oxo-1,3-dihydro-2-benzofuran-5-yl)amino]-4-{[(1S)-2-hydroxy-1-phenylethyl]amino}pyrimidine-5-carboxylic acid (6.9 mg, 27.6% yield). HPLC $t_R$: 1.29 min. LC/MS Condition 3. ES [MS] m/z: 435.1 [M+H]$^+$ $^1$H NMR (500 MHz, DMSO-d$_6$) δ 9.67 (br. s., 1H), 8.59 (s, 1H), 8.01 (s, 1H), 7.72 (d, J=8.4 Hz, 1H), 7.61 (d, J=8.4 Hz, 1H), 7.42-7.33 (m, 4H), 7.28-7.23 (m, 1H), 5.33 (br. s., 1H), 3.86 (dd, J=11.0, 4.8 Hz, 1H), 3.80 (dd, J=10.6, 5.9 Hz, 1H), 1.59 (s, 3H), 1.55 (s, 3H).

Example 4

N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide

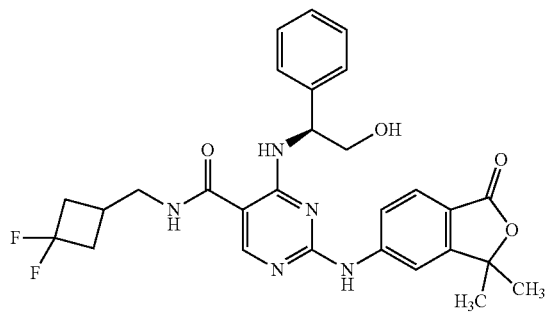

(4)

HATU (11.2 mg, 0.029 mmol) was added to a stirred solution of (S)-2-((3,3-dimethyl-1-oxo-1,3-dihydroisobenzofuran-5-yl)amino)-4-((2-hydroxy-1-phenylethyl) amino) pyrimidine-5-carboxylic acid (8.5 mg, 0.020 mmol), (3,3-difluorocyclobutyl) methanamine (4.74 mg, 0.039 mmol), and Hünig's Base (13.67 μL, 0.078 mmol) in DMF (196 μL) at 0° C. under nitrogen (g). The reaction mixture was then removed from the cold bath and warmed to room temperature. After 16 h, the reaction mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 12 minutes, then a 5-minute hold at 100% B; Flow: 20 mL/min. Fractions containing the product were combined and dried via centrifugal evaporation to afford N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (5.6 mg, 53.2% yield). HPLC $t_R$: 1.89 min; LC/MS Condition 3. ES [MS] m/z: 538.2 [M+H]$^+$. $^1$H NMR (500 MHz, DMSO-d$_6$) δ 10.19-9.97 (m, 1H), 9.80-9.61 (m, 1H), 8.51 (s, 2H), 7.97 (s, 1H), 7.73-7.54 (m, 2H), 7.37 (d, J=4.4 Hz, 4H), 7.29-7.22 (m, 1H), 5.29 (dt, J=7.9, 5.0 Hz, 1H), 5.15 (t, J=5.0 Hz, 1H), 3.89-3.71 (m, 2H), 2.75-2.59 (m, 2H), 2.47-2.33 (m, 3H), 1.61-1.50 (m, 6H).

Example 5

2-[(3,3-dimethyl-1-oxo-1,3-dihydro-2-benzofuran-5-yl)amino]-N-[3-(dimethylamino)propyl]-4-{[(1S)-2-hydroxy-1-phenylethyl]amino}pyrimidine-5-carboxamide (5)

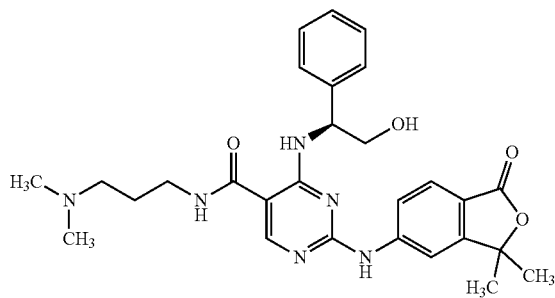

Example 5 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using N,N-dimethyl-1,3-propanediamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. to afford 2-[(3,3-dimethyl-1-oxo-1,3-dihydro-2-benzofuran-5-yl) amino]-N-[3-(dimethylamino)propyl]-4-{[(1S)-2-hydroxy-1-phenylethyl]amino}pyrimidine-5-carboxamide (3.6 mg, 38.6% yield). HPLC $t_R$: 0.96 min; LC/MS Condition 3. ES [MS] m/z: 519.2 [M+H]$^+$. $^1$H NMR (500 MHz, DMSO-$d_6$) δ 9.87-9.70 (m, 1H), 8.66-8.54 (m, 1H), 8.52-8.43 (m, 1H), 8.05-7.94 (m, 1H), 7.73-7.55 (m, 2H), 7.46-7.30 (m, 4H), 7.22 (s, 1H), 5.35-5.22 (m, 1H), 3.88-3.70 (m, 2H), 3.33-3.19 (m, 1H), 2.31 (t, J=7.2 Hz, 2H), 2.23-2.12 (m, 6H), 1.95-1.88 (m, 3H), 1.74-1.63 (m, 2H), 1.61-1.48 (m, 6H).

Example 6

2-[(3,3-dimethyl-1-oxo-1,3-dihydro-2-benzofuran-5-yl)amino]-4-{[(1S)-2-hydroxy-1-phenylethyl]amino}-N-[(pyridin-2-yl)methyl]pyrimidine-5-carboxamide (5)

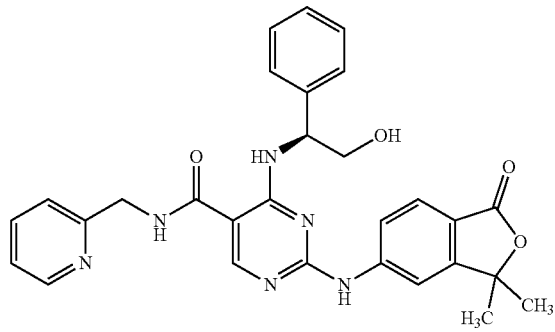

Example 6 was prepare according to the genera preparation procedure for N-[(3,3-difluorocyclobutyl)methyl]-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide using 2-(aminomethyl)pyridine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to afford 2-[(3,3-dimethyl-1-oxo-1,3-dihydro-2-benzofuran-5-yl) amino]-4-{[(1S)-2-hydroxy-1-phenylethyl]amino}-N-[(pyridin-2-yl)methyl]pyrimidine-5-carboxamide (7.9 mg, 83.7% yield). HPLC $t_R$: 1.93 min; LC/MS Condition 2. ES [MS]m/z: 525.2 [M+H]$^+$. $^1$H NMR (500 MHz, DMSO-$d_6$) δ 9.83-9.66 (m, 1H), 9.16-8.98 (m, 1H), 8.84-8.68 (m, 1H), 8.49 (s, 1H), 8.02 (br d, J=4.0 Hz, 1H), 7.87-7.74 (m, 1H), 7.73-7.57 (m, 2H), 7.42 (br d, J=5.9 Hz, 5H), 7.31-7.21 (m, 2H), 5.33-5.25 (m, 1H), 4.61-4.53 (m, 2H), 3.87-3.70 (m, 2H), 1.61-1.50 (m, 6H).

Example 7

2-[(3,3-dimethyl-1-oxo-1,3-dihydro-2-benzofuran-5-yl)amino]-4-{[(1S)-2-hydroxy-1-phenylethyl] amino}-N-[3-(morpholin-4-yl)propyl]pyrimidine-5-carboxamide (7)

Example 7 was prepared according to the general preparation procedure for N-[(3,3-difluorocyclobutyl)methyl]-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide using N-(3-aminopropyl)morpholine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to afford 2-[(3,3-dimethyl-1-oxo-1,3-dihydro-2-benzofuran-5-yl) amino]-4-{[(1S)-2-hydroxy-1-phenylethyl]amino}-N-[3-(morpholin-4-yl)propyl]pyrimidine-5-carboxamide (5.2 mg, 51.5% yield). HPLC $t_R$: 1.82 min; LC/MS Condition 2. ES [MS] m/z: 561.2 [M+H]$^+$. $^1$H NMR (500 MHz, DMSO-$d_6$) δ 9.79 (br d, J=7.7 Hz, 1H), 8.67-8.55 (m, 1H), 8.52-8.37 (m, 1H), 8.10-7.97 (m, 1H), 7.76-7.54 (m, 2H), 7.48-7.31 (m, 4H), 7.30-7.22 (m, 1H), 5.32-5.25 (m, 1H), 3.87-3.72 (m, 2H), 3.55 (s, 2H), 2.44-2.30 (m, 5H), 1.64 (s, 2H), 1.61-1.50 (m, 6H).

Example 8

2-[(3,3-dimethyl-1-oxo-1,3-dihydro-2-benzofuran-5-yl)amino]-4-{[(1S)-2-hydroxy-1-phenylethyl]amino}-N-(2-methoxyethyl)pyrimidine-5-carboxamide (8)

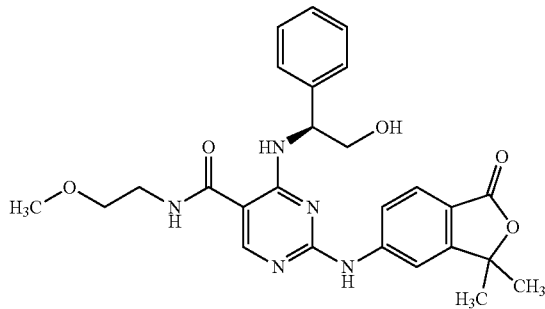

Example 8 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using 2-methoxyethylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 18 minutes, then a 4-minute hold at 100% B; Flow: 20 mL/min. to afford 2-[(3,3-dimethyl-1-oxo-1,3-dihydro-2-benzofuran-5-yl)amino]-4-{[(1S)-2-hydroxy-1-phenylethyl]amino}-N-(2-methoxyethyl)pyrimidine-5-carboxamide (3.5 mg, 39.6% yield). HPLC $t_R$: 0.99 min; LC/MS Condition 3. ES [MS] m/z: 492.1 [M+H]$^+$. $^1$H NMR (500 MHz, DMSO-$d_6$) δ 9.89-9.68 (m, 1H), 8.68-8.55 (m, 1H), 8.53-8.41 (m, 1H), 8.05-7.84 (m, 1H), 7.77-7.58 (m, 2H), 7.41-7.32 (m, 4H), 7.30-7.19 (m, 1H), 5.33 (s, 1H), 3.87-3.72 (m, 2H), 3.35-3.24 (m, 1H), 1.98-1.86 (m, 4H), 1.63-1.47 (m, 6H).

Example 9

2-[(3,3-dimethyl-1-oxo-1,3-dihydro-2-benzofuran-5-yl)amino]-N-[2-(dimethylamino)ethyl]-4-{[(1S)-2-hydroxy-1-phenylethyl]amino}pyrimidine-5-carboxamide (9)

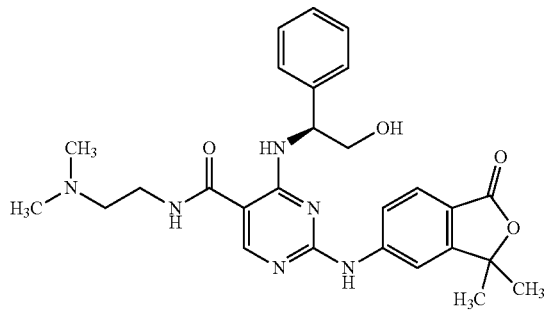

Example 9 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using N,N-dimethylethylenediamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 20 minutes, then a 4-minute hold at 100% B; Flow: 20 mL/min. Fractions containing the product were combined and dried via centrifugal evaporation to afford 2-[(3,3-dimethyl-1-oxo-1,3-dihydro-2-benzofuran-5-yl)amino]-N-[2-(dimethylamino)ethyl]-4-{[(1S)-2-hydroxy-1-phenylethyl]amino}pyrimidine-5-carboxamide (4.1 mg, 45.1% yield). HPLC $t_R$: 1.53 min; LC/MS Condition 3. ES [MS] m/z: 505.2 [M+H]$^+$. $^1$H NMR (500 MHz, DMSO-$d_6$) δ 9.88 (s, 1H), 8.66-8.54 (m, 1H), 8.40-8.32 (m, 1H), 8.05-7.92 (m, 1H), 7.74-7.55 (m, 2H), 7.47-7.33 (m, 3H), 7.30-7.19 (m, 1H), 5.32-5.12 (m, 1H), 3.89-3.67 (m, 2H), 2.43 (t, J=7.0 Hz, 2H), 2.25-2.16 (m, 6H), 1.96-1.88 (m, 3H), 1.65-1.48 (m, 6H).

Example 10

N-benzyl-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (10)

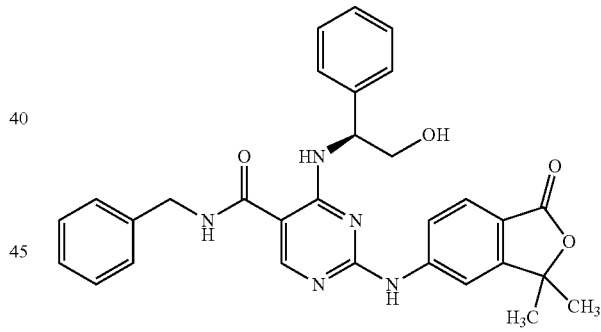

Example 10 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using benzylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 18 minutes, then a 4-minute hold at 100% B; Flow: 20 mL/min to afford N-benzyl-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (3.6 mg, 38.2% yield). HPLC $t_R$: 2.22 min; LC/MS Condition 2. ES [MS] m/z: 524.2 [M+H]$^+$. $^1$H NMR (500 MHz, DMSO-$d_6$) δ 10.18-10.07 (m, 1H), 9.86-9.69 (m, 1H), 9.11-8.92 (m, 1H), 8.74-8.66 (m, 1H), 8.09-7.93 (m, 1H), 7.80-7.55 (m, 2H), 7.44-7.32 (m, 8H), 7.31-7.21 (m, 2H), 5.37-5.22 (m, 1H), 4.58-4.38 (m, 2H), 3.70 (s, 2H), 1.64-1.46 (m, 6H).

Example 11

N-tert-butyl-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (11)

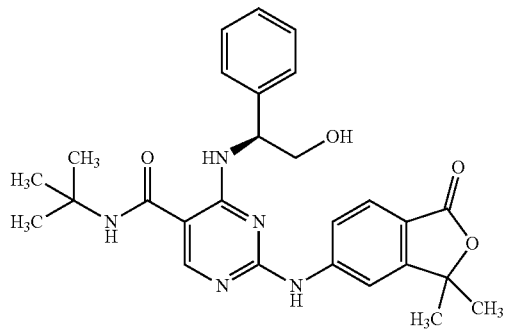

Example 11 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using tert-butylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 19 minutes, then a 4-minute hold at 100% B; Flow: 20 mL/min to afford N-tert-butyl-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (8.7 mg, 98.7% yield). HPLC $t_R$: 1.05 min; LC/MS Condition 2. ES [MS] m/z: 490.1 [M+H]$^+$. $^1$H NMR (500 MHz, DMSO-d$_6$) δ 9.58 (s, 1H), 8.53 (br d, J=1.8 Hz, 1H), 8.09-7.97 (m, 1H), 7.78-7.70 (m, 1H), 7.70-7.56 (m, 2H), 7.42-7.33 (m, 4H), 7.30-7.20 (m, 1H), 5.35-5.23 (m, 1H), 3.88-3.74 (m, 2H), 1.61-1.49 (m, 6H), 1.44-1.35 (m, 9H).

Example 12

2-[(3,3-dimethyl-1-oxo-1,3-dihydro-2-benzofuran-5-yl)amino]-4-{[(1S)-2-hydroxy-1-phenylethyl]amino}-N-(2-methylpropyl)pyrimidine-5-carboxamide (12)

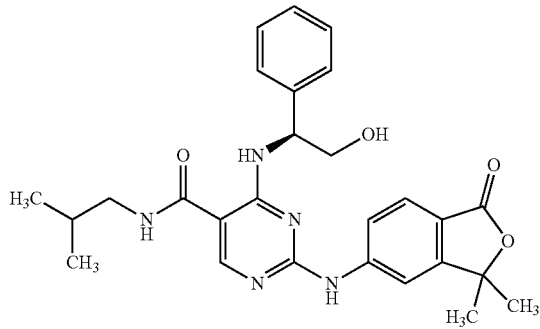

Example 12 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using iso-butylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 18 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-(2-methylpropyl)pyrimidine-5-carboxamide (5.7 mg, 64.7% yield). HPLC $t_R$: 0.99 min; LC/MS Condition 3. ES [MS] m/z: 490.3 [M+H]$^+$. $^1$H NMR (500 MHz, DMSO-d$_6$) δ 9.88-9.66 (m, 1H), 8.66 (br d, J=4.4 Hz, 1H), 8.52-8.38 (m, 1H), 8.11-7.95 (m, 1H), 7.73-7.55 (m, 2H), 7.37 (d, J=4.4 Hz, 4H), 7.30-7.19 (m, 1H), 5.32-5.17 (m, 1H), 3.89-3.68 (m, 2H), 3.14-3.00 (m, 2H), 1.91-1.81 (m, 2H), 1.64-1.47 (m, 6H), 0.92 (d, J=6.6 Hz, 6H).

Example 13

2-[(3,3-dimethyl-1-oxo-1,3-dihydro-2-benzofuran-5-yl)amino]-4-{[(1S)-2-hydroxy-1-phenylethyl]amino}-N-(propan-2-yl)pyrimidine-5-carboxamide (13)

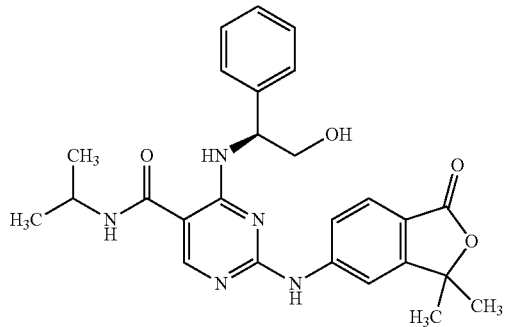

Example 13 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using iso-propylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 19 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-(propan-2-yl)pyrimidine-5-carboxamide (5.7 mg, 66.6% yield). HPLC $t_R$: 2.06 min; LC/MS Condition 2. ES [MS] m/z: 476.2 [M+H]$^+$. $^1$H NMR (500 MHz, DMSO-d$_6$) δ 9.89-9.75 (m, 1H), 8.72-8.56 (m, 1H), 8.18 (d, J=7.7 Hz, 1H), 8.02 (s, 1H), 7.72-7.57 (m, 2H), 7.44-7.33 (m, 4H), 7.21 (s, 1H), 5.24 (s, 1H), 4.06 (br d, J=3.7 Hz, 1H), 3.71 (s, 2H), 1.62-1.50 (m, 6H), 1.23-1.14 (m, 6H).

Example 14

2-[(3,3-dimethyl-1-oxo-1,3-dihydro-2-benzofuran-5-yl)amino]-4-{[(1S)-2-hydroxy-1-phenylethyl] amino}-N-propylpyrimidine-5-carboxamide

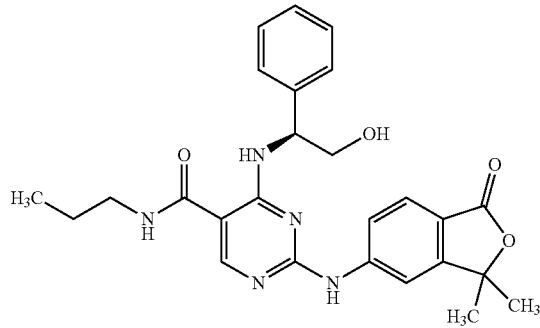

(14)

Example 14 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using n-propylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 18 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-propylpyrimidine-5-carboxamide (4.8 mg, 56.1% yield). HPLC $t_R$: 0.98 min; LC/MS Condition 3. ES [MS] m/z: 476.1 [M+H]$^+$. $^1$H NMR (500 MHz, DMSO-d$_6$) δ 9.93-9.66 (m, 1H), 8.59 (s, 1H), 8.51-8.36 (m, 1H), 8.04-7.92 (m, 1H), 7.59 (s, 2H), 7.40 (s, 4H), 7.29-7.19 (m, 1H), 5.37-5.16 (m, 1H), 3.88-3.66 (m, 2H), 3.26-3.18 (m, 1H), 1.64-1.48 (m, 8H), 0.98-0.85 (m, 3H).

Example 15

2-[(3,3-dimethyl-1-oxo-1,3-dihydro-2-benzofuran-5-yl)amino]-4-{[(1S)-2-hydroxy-1-phenylethyl] amino}-N-(1-phenylethyl)pyrimidine-5-carboxamide

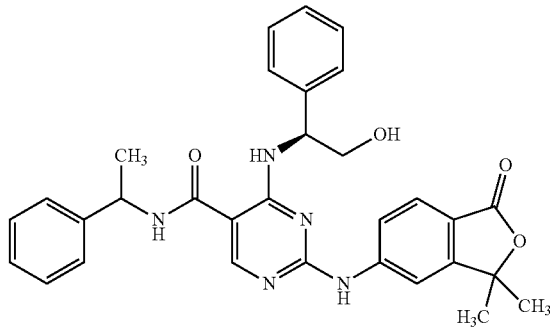

(15)

Example 15 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using DL-alpha-methylbenzylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 19 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-(1-phenylethyl)pyrimidine-5-carboxamide (3.9 mg, 40.3% yield). HPLC $t_R$: 0.99 min; LC/MS Condition 3. ES [MS] m/z: 538.2 [M+H]$^+$. $^1$H NMR (500 MHz, DMSO-d$_6$) δ 10.22-10.05 (m, 1H), 9.82-9.59 (m, 1H), 8.89 (s, 2H), 8.08 (br d, J=12.8 Hz, 1H), 7.77-7.55 (m, 2H), 7.29-7.18 (m, 1H), 7.46-7.16 (m, 1H), 5.32-5.22 (m, 1H), 5.22-5.08 (m, 1H), 3.88-3.66 (m, 2H), 1.62-1.55 (m, 3H), 1.54-1.51 (m, 3H), 1.51-1.44 (m, 3H).

Example 16

2-[(3,3-dimethyl-1-oxo-1,3-dihydro-2-benzofuran-5-yl)amino]-4-{[(1S)-2-hydroxy-1-phenylethyl] amino}-N-[(2-methylphenyl)methyl]pyrimidine-5-carboxamide

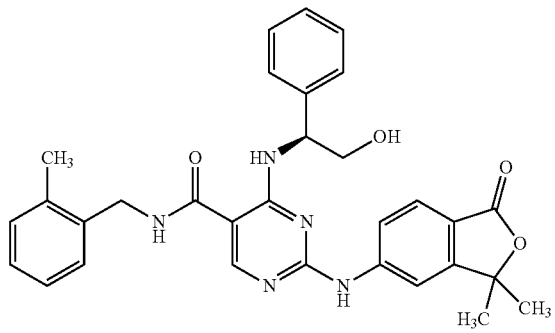

(16)

Example 16 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using 2-methylbenzylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-[(2-methylphenyl)methyl]pyrimidine-5-carboxamide (3.9 mg, 40.3% yield). HPLC $t_R$: 2.07 min; LC/MS Condition 3. ES [MS] m/z: 538.2 [M+H]$^+$. $^1$H NMR (500 MHz, DMSO-d$_6$) δ 9.74-9.58 (m, 1H), 8.78-8.71 (m, 1H), 8.70-8.65 (m, 1H), 8.03 (br d, J=1.8 Hz, 1H), 7.78-7.55 (m, 2H), 7.40 (s, 4H), 7.32-7.23 (m, 2H), 7.23-7.11 (m, 3H), 5.39-5.27 (m, 1H), 4.52-4.42 (m, 2H), 3.70 (br d, J=1.5 Hz, 2H), 2.40-2.30 (m, 3H), 1.57 (d, J=17.2 Hz, 6H).

Example 17

2-[(3,3-dimethyl-1-oxo-1,3-dihydro-2-benzofuran-5-yl)amino]-4-{[(1S)-2-hydroxy-1-phenylethyl]amino}-N-[(1S,2R)-2-phenylcyclopropyl]pyrimidine-5-carboxamide (17)

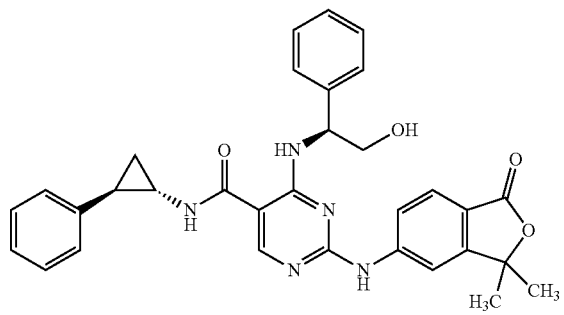

Example 17 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using trans-2-phenylcyclopropylamine hydrochloride instead of (3,3-difluorocyclobutyl) methanamine. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-[(1S,2R)-2-phenylcyclopropyl]pyrimidine-5-carboxamide (3.4 mg, 34.4% yield). HPLC $t_R$: 2.12 min; LC/MS Condition 3. ES [MS] m/z: 550.2 [M+H]$^+$. $^1$H NMR (500 MHz, DMSO-d$_6$) δ 9.78-9.59 (m, 1H), 8.68-8.55 (m, 1H), 8.54-8.45 (m, 1H), 8.04-7.92 (m, 1H), 7.71 (d, J=8.4 Hz, 1H), 7.64-7.53 (m, 1H), 7.42-7.12 (m, OH), 5.38-5.24 (m, 1H), 3.87-3.70 (m, 2H), 2.18-2.07 (m, 1H), 1.65-1.50 (m, 6H), 1.44-1.30 (m, 1H), 1.16 (s, 1H).

Example 18

2-[(3,3-dimethyl-1-oxo-1,3-dihydro-2-benzofuran-5-yl)amino]-N-ethyl-4-{[(1S)-2-hydroxy-1-phenylethyl]amino}pyrimidine-5-carboxamide (18)

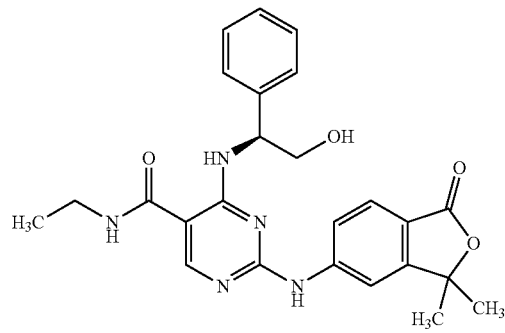

Example 18 was prepared according to the general preparation procedure for N-[(3,3-difluorocyclobutyl)methyl]-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide using ethylamine hydrochloride instead of (3,3-difluorocyclobutyl)methanamine. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 minutes, then a 4-minute hold at 100% B; Flow: 20 mL/min to afford 2-[(3,3-dimethyl-1-oxo-1,3-dihydro-2-benzofuran-5-yl) amino]-N-ethyl-4-{[(1S)-2-hydroxy-1-phenylethyl]amino}pyrimidine-5-carboxamide (7.2 mg, 86.7% yield). HPLC $t_R$: 1.75 min; LC/MS Condition 3. ES [MS] m/z: 462.2 [M+H]$^+$. $^1$H NMR (500 MHz, DMSO-d$_6$) δ 9.66 (s, 1H), 8.63-8.47 (m, 1H), 8.44-8.13 (m, 1H), 8.08-7.89 (m, 1H), 7.77-7.50 (m, 2H), 7.46-7.19 (m, 6H), 5.38-5.21 (m, 1H), 3.88-3.69 (m, 2H), 1.61-1.50 (m, 6H), 1.21-1.09 (m, 3H).

Example 19

2-[(3,3-dimethyl-1-oxo-1,3-dihydro-2-benzofuran-5-yl)amino]-4-{[(1S)-2-hydroxy-1-phenylethyl]amino}-N-[3-(1H-imidazol-1-yl)propyl]pyrimidine-5-carboxamide (19)

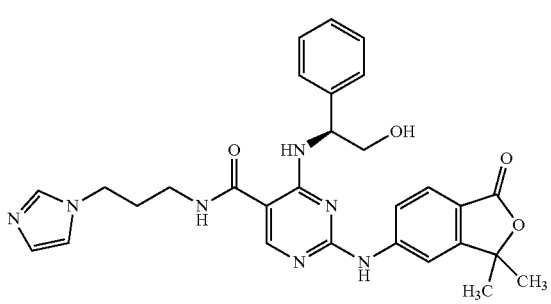

Example 19 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using 1-(3-aminopropyl)imidazole instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 14-54% B over 20 minutes, then a 4-minute hold at 100% B; Flow: 20 mL/min to afford 2-[(3,3-dimethyl-1-oxo-1,3-dihydro-2-benzofuran-5-yl) amino]-4-{[(1S)-2-hydroxy-1-phenylethyl]amino}-N-[3-(1H-imidazol-1-yl)propyl]pyrimidine-5-carboxamide (8.7 mg, 89.2% yield). HPLC $t_R$: 1.54 min; LC/MS Condition 3. ES [MS] m/z: 542.3 [M+H]$^+$. $^1$H NMR (500 MHz, DMSO-d$_6$) δ 9.69-9.55 (m, 1H), 8.66-8.50 (m, 1H), 8.26 (s, 1H), 8.02-7.86 (m, 1H), 7.75-7.57 (m, 3H), 7.45-7.32 (m, 4H), 7.30-7.22 (m, 1H), 7.21-7.15 (m, 1H), 7.02-6.80 (m, 1H), 5.37-5.26 (m, 1H), 4.06 (t, J=7.0 Hz, 2H), 3.72 (br d, J=2.2 Hz, 2H), 3.29-3.19 (m, 1H), 2.06-1.96 (m, 3H), 1.62-1.50 (m, 6H).

Example 20

2-[(3,3-dimethyl-1-oxo-1,3-dihydro-2-benzofuran-5-yl)amino]-4-{[(1S)-2-hydroxy-1-phenylethyl]amino}-N-[(5-methylpyrazin-2-yl)methyl]pyrimidine-5-carboxamide (20)

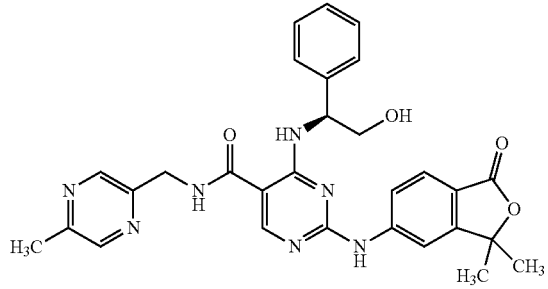

Example 20 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using 2-(aminomethyl)-5-methylpyrazine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 15-55% B over 19 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-[(5-methylpyrazin-2-yl)methyl]pyrimidine-5-carboxamide (6.2 mg, 63.8% yield). HPLC $t_R$: 1.48 min; LC/MS Condition 2. ES [MS] m/z: 540.2 [M+H]$^+$. $^1$H NMR (500 MHz, DMSO-d$_6$) δ 9.69-9.57 (m, 1H), 9.02-8.86 (m, 1H), 8.65 (s, 1H), 8.58-8.37 (m, 2H), 7.97 (d, J=0.7 Hz, 1H), 7.84-7.54 (m, 2H), 7.45-7.29 (m, 5H), 7.26-7.17 (m, 1H), 5.39-5.21 (m, 1H), 4.75-4.46 (m, 2H), 3.68 (s, 2H), 1.66-1.40 (m, 7H).

Example 21

2-[(3,3-dimethyl-1-oxo-1,3-dihydro-2-benzofuran-5-yl)amino]-4-{[(1S)-2-hydroxy-1-phenylethyl]amino}-N-(prop-2-yn-1-yl)pyrimidine-5-carboxamide (21)

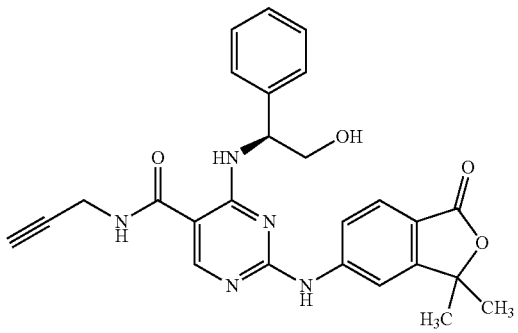

Example 21 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using propargylamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 minutes, then a 4-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-(prop-2-yn-1-yl)pyrimidine-5-carboxamide (3.9 mg, 46.0% yield). HPLC $t_R$: 1.75 min; LC/MS Condition 3. ES [MS] m/z: 472.2 [M+H]$^+$. $^1$H NMR (500 MHz, DMSO-d$_6$) δ 9.74-9.59 (m, 1H), 8.85 (s, 1H), 8.66-8.51 (m, 1H), 7.96 (d, J=1.1 Hz, 1H), 7.74 (s, 1H), 7.56 (s, 1H), 7.43-7.32 (m, 4H), 7.30-7.21 (m, 1H), 5.38 (s, 1H), 4.15-3.98 (m, 2H), 3.89-3.73 (m, 2H), 1.62-1.45 (m, 6H).

Example 22

N-(1-benzylpyrrolidin-3-yl)-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide (22)

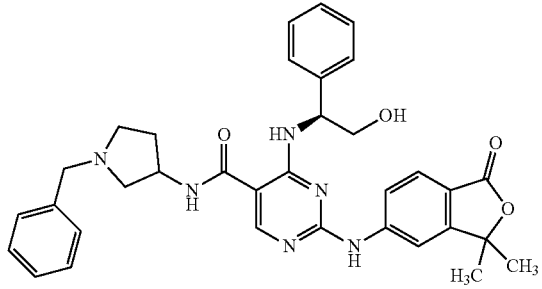

Example 22 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using 1-benzyl-3-aminopyrrolidine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 20 minutes, then a 4-minute hold at 100% B; Flow: 20 mL/min to afford N-(1-benzylpyrrolidin-3-yl)-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (7.1 mg, 66.6% yield). HPLC $t_R$: 1.62 min; LC/MS Condition 2. ES [MS] m/z: 593.2 [M+H]+. 1H NMR (500 MHz, DMSO-$d_6$) δ 9.64-9.44 (m, 1H), 8.67-8.52 (m, 1H), 8.37-8.17 (m, 1H), 7.93-7.83 (m, 1H), 7.76-7.67 (m, 1H), 7.59 (d, J=8.4 Hz, 1H), 7.37-7.14 (m, 12H), 5.33-5.19 (m, 1H), 4.46-4.28 (m, 1H), 3.86-3.71 (m, 2H), 3.59-3.45 (m, 3H), 2.97-2.79 (m, 1H), 2.73 (s, 1H), 2.28-2.09 (m, 1H), 1.63-1.45 (m, 6H).

Example 23

2-[(3,3-dimethyl-1-oxo-1,3-dihydro-2-benzofuran-5-yl)amino]-4-{[(1S)-2-hydroxy-1-phenylethyl]amino}-N-[(3-methyloxetan-3-yl)methyl]pyrimidine-5-carboxamide

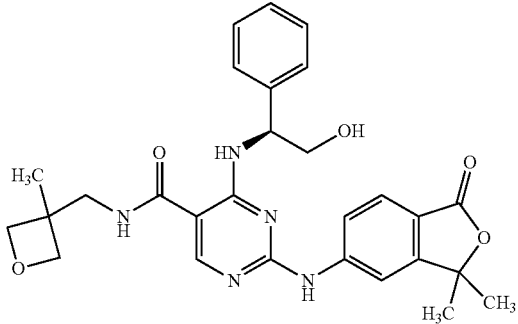

(23)

Example 23 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using (3-methyloxetan-3-yl)methanamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-[(3-methyloxetan-3-yl)methyl]pyrimidine-5-carboxamide (12.6 mg, 88.0% yield). HPLC $t_R$: 1.57 min; LC/MS Condition 2. ES [MS] m/z: 518.2 [M+H]+. 1H NMR (500 MHz, DMSO-$d_6$) δ 9.48 (br d, J=19.1 Hz, 1H), 8.69-8.31 (m, 2H), 8.05-7.83 (m, 1H), 7.78-7.55 (m, 2H), 7.41-7.31 (m, 4H), 7.28-7.21 (m, 1H), 5.37-5.25 (m, 1H), 4.54-4.44 (m, 2H), 4.24 (d, J=5.5 Hz, 2H), 3.87-3.70 (m, 2H), 1.56 (br d, J=16.1 Hz, 6H), 1.35-1.25 (m, 3H).

Example 24

2-[(3,3-dimethyl-1-oxo-1,3-dihydro-2-benzofuran-5-yl)amino]-N-{[(3R)-3-hydroxy-1-azabicyclo[2.2.2]octan-3-yl]methyl}-4-{[(1S)-2-hydroxy-1-phenylethyl]amino}pyrimidine-5-carboxamide

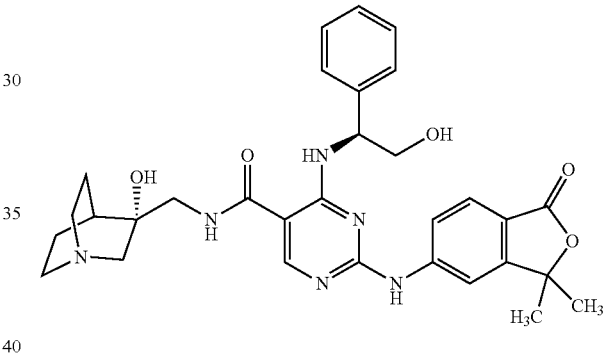

(24)

Example 24 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using (1S,3R,4S)-3-(aminomethyl)quinuclidin-3-ol bishydrochloride instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to afford 2-[(3,3-dimethyl-1-oxo-1,3-dihydro-2-benzofuran-5-yl)amino]-N-{[(3R)-3-hydroxy-1-azabicyclo[2.2.2]octan-3-yl]methyl}-4-{[(1S)-2-hydroxy-1-phenylethyl]amino}pyrimidine-5-carboxamide (17 mg, 100% yield). HPLC $t_R$: 1.3 min; LC/MS Condition 2. ES [MS] m/z: 573.3 [M+H]+. 1H NMR (500 MHz, DMSO-$d_6$) δ 9.60-9.40 (m, 1H), 8.65-8.52 (m, 1H), 8.09-7.84 (m, 2H), 7.77 (br dd, J=16.3, 3.1 Hz, 1H), 7.54 (s, 1H), 7.44-7.29 (m, 5H), 7.29-7.13 (m, 1H), 5.35-5.18 (m, 1H), 3.87-3.66 (m, 2H), 2.89-2.59 (m, 6H), 2.08-1.68 (m, 10H), 1.63-1.44 (m, 7H), 1.36-1.22 (m, 1H).

Example 25

N-({1-azabicyclo[2.2.2]octan-3-yl}methyl)-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (25)

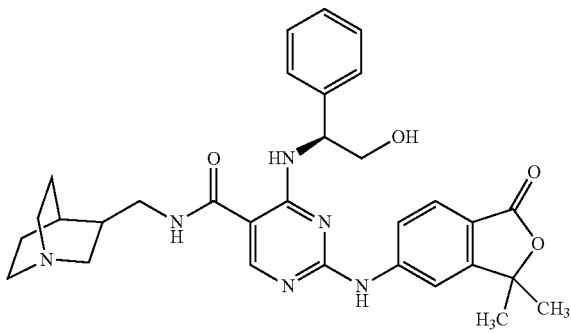

Example 25 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using (1S,4S)-quinuclidin-3-ylmethanamine instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to afford N-({1-azabicyclo[2.2.2]octan-3-yl}methyl)-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (17.9 mg, 82% yield). HPLC $t_R$: 1.33 min; LC/MS Condition 2. ES [MS] m/z: 557.2 [M+H]$^+$. $^1$H NMR (500 MHz, DMSO-d$_6$) δ 9.71-9.55 (m, 1H), 8.67-8.49 (m, 1H), 8.41-8.26 (m, 1H), 8.09-7.86 (m, 1H), 7.71 (br d, J=7.7 Hz, 1H), 7.63 (br d, J=2.6 Hz, 1H), 7.46-7.32 (m, 4H), 7.16 (s, 1H), 5.35-5.26 (m, 1H), 3.70 (s, 2H), 3.49-3.23 (m, 1H), 3.08 (s, 1H), 2.47-2.40 (m, 1H), 2.06 (s, 1H), 1.85-1.75 (m, 2H), 1.74-1.61 (m, 1H), 1.56 (br d, J=16.5 Hz, 6H), 1.49-1.36 (m, 1H).

Example 26

2-[(3,3-dimethyl-1-oxo-1,3-dihydro-2-benzofuran-5-yl)amino]-4-{[(1S)-2-hydroxy-1-phenylethyl]amino}-N-({1-[(morpholin-4-yl)methyl]cyclopropyl}methyl)pyrimidine-5-carboxamide (26)

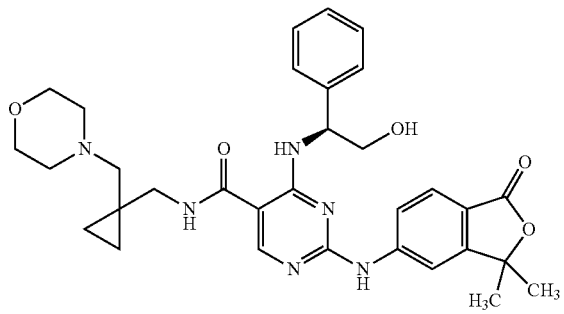

Example 26 was prepared according to the general preparation procedure for N-[(3,3-difluorocyclobutyl)methyl]-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide using ((1-(morpholinomethyl)cyclopropyl)methanamine bishydrochloride instead of (3,3-difluorocyclobutyl)methanamine. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to afford 2-[(3,3-dimethyl-1-oxo-1,3-dihydro-2-benzofuran-5-yl)amino]-4-{[(1S)-2-hydroxy-1-phenylethyl]amino}-N-({1-[(morpholin-4-yl)methyl]cyclopropyl}methyl)pyrimidine-5-carboxamide (17.7 mg, 100% yield). HPLC $t_R$: 1.24 min; LC/MS Condition 3. ES [MS] m/z: 587.2 [M+H]$^+$. $^1$H NMR (500 MHz, DMSO-d$_6$) δ 9.66-9.47 (m, 1H), 8.62-8.49 (m, 1H), 8.04-7.87 (m, 1H), 7.80-7.67 (m, 1H), 7.63-7.49 (m, 1H), 7.40-7.29 (m, 4H), 7.27-7.17 (m, 1H), 5.37-5.22 (m, 1H), 3.88-3.70 (m, 2H), 3.68-3.51 (m, 3H), 2.45-2.38 (m, 3H), 2.35-2.23 (m, 2H), 1.48 (s, 6H), 0.67-0.45 (m, 2H), 0.43-0.19 (m, 2H).

Example 27

5-[(5-{1,8-dioxa-3-azaspiro[4.5]dec-2-en-2-yl}-4-{[(1S)-2-hydroxy-1-phenylethyl]amino}pyrimidin-2-yl)amino]-3,3-dimethyl-1,3-dihydro-2-benzofuran-1-one (27)

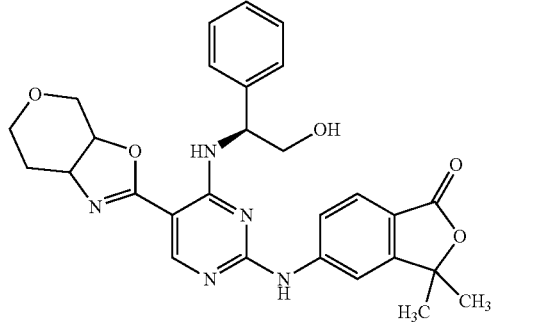

HATU (42.5 mg, 0.112 mmol) was added to a stirred solution of (S)-2-((3,3-dimethyl-1-oxo-1,3-dihydroisobenzofuran-5-yl)amino)-4-((2-hydroxy-1-phenylethyl)amino)pyrimidine-5-carboxylic acid (24.3 mg, 0.056 mmol), 4-(aminomethyl)tetrahydro-2H-pyran-4-ol (14.67 mg, 0.112 mmol), and Hünig's Base (39.1 μL, 0.224 mmol) in DMF (559 μL) at 0° C. under nitrogen (g). The reaction mixture was then removed from the cold bath and warmed to room temperature. After 16 h, LC/MS indicated conversion to the amide intermediate, (S)-2-((3,3-dimethyl-1-oxo-1,3-dihydroisobenzofuran-5-yl)amino)-4-((2-hydroxy-1-phenylethyl) amino)-N-((4-hydroxytetrahydro-2H-pyran-4-yl)methyl)pyrimidine-5-carboxamide. The volatiles were removed under positive nitrogen (g) pressure. A concentrated aqueous solution of $H_2SO_4$ (0.3 mL) was added to the reaction flask to induce cyclization, and the reaction mixture was stirred for 1 h. The volatiles were removed under reduced pressure, the solids were dissolved in methanol, the mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 20 minutes, then a 4-minute hold at 100% B; Flow: 20 mL/min to afford 5-[(5-{1,8-dioxa-3-azaspiro [4.5]dec-2-en-2-yl}-4-{[(1S)-2-hydroxy-1-phenylethyl]amino} pyrimidin-2-yl)amino]-3,3-dimethyl-1,3-dihydro-2-benzofuran-1-one (4 mg, 13.1% yield). HPLC $t_R$: 1.50 min; LC/MS Condition 3. ES [MS] m/z: 530.2 [M+H]$^+$. $^1$H NMR (500 MHz, DMSO-d$_6$) δ 9.79-9.60 (m, 1H), 8.60-8.36 (m, 1H), 8.14-7.93 (m, 1H), 7.76-7.70 (m, 1H), 7.62 (d, J=8.4 Hz, 1H), 7.44-7.33 (m, 4H), 7.32-7.21 (m, 1H), 5.45-5.32 (m, 1H), 3.89-3.76 (m, 6H), 3.74-3.61 (m, 2H), 1.91-1.74 (m, 4H), 1.57 (d, J=18.7 Hz, 6H).

Example 28

5-[(4-{[(1S)-2-hydroxy-1-phenylethyl]amino}-5-(3-methyl-1,2,4-oxadiazol-5-yl) pyrimidin-2-yl)amino]-3,3-dimethyl-1,3-dihydro-2-benzofuran-1-one (28)

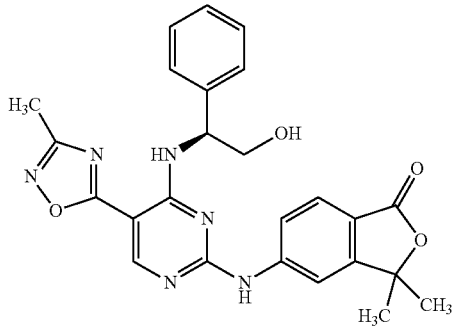

To a vial charged with (S)-ethyl 2-((3,3-dimethyl-1-oxo-1,3-dihydroisobenzofuran-5-yl)amino)-4-((2-hydroxy-1-phenylethyl)amino)pyrimidine-5-carboxylate (Example 2, 23.0 mg, 0.050 mmol) were added N-hydroxyacetimidamide (18.4 mg, 0.249 mmol) and molecular sieves (3 Å, freshly activated, 100 mg). The vial was flushed with nitrogen and treated with EtOH (2 mL). After stirring for 5 min, the mixture was treated with sodium ethanolate (13.5 mg, 0.199 mmol). The resulting mixture was sealed and heated at 70° C. overnight. The reaction mixture was cooled to room temperature, diluted with EtOAc, and washed with water. The reaction mixture was concentrated under reduced pressure and the crude material was redissolved in methanol prior to purification via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to afford 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one (4.8 mg, 18.4% yield). HPLC $t_R$: 1.92 min; LC/MS Condition 3. ES [MS] m/z: 473.2 [M+H]$^+$. $^1$H NMR (500 MHz, DMSO-d$_6$) δ 10.24 (s, 1H), 8.98 (d, J=8.1 Hz, 1H), 8.81 (s, 1H), 7.98 (s, 1H), 7.75 (d, J=8.4 Hz, 1H), 7.65 (d, J=8.4 Hz, 1H), 7.45-7.41 (m, 2H), 7.40-7.35 (m, 2H), 7.31-7.23 (m, 1H), 5.44 (d, J=7.7 Hz, 1H), 3.94 (dd, J=10.8, 4.2 Hz, 1H), 3.86 (dd, J=11.0, 5.5 Hz, 1H), 2.46 (s, 3H), 1.60 (s, 3H), 1.56 (s, 3H).

Example 29

5-{[5-(3-ethyl-1,2,4-oxadiazol-5-yl)-4-{[(1S)-2-hydroxy-1-phenylethyl]amino}pyrimidin-2-yl] amino}-3,3-dimethyl-1,3-dihydro-2-benzofuran-1-one (29)

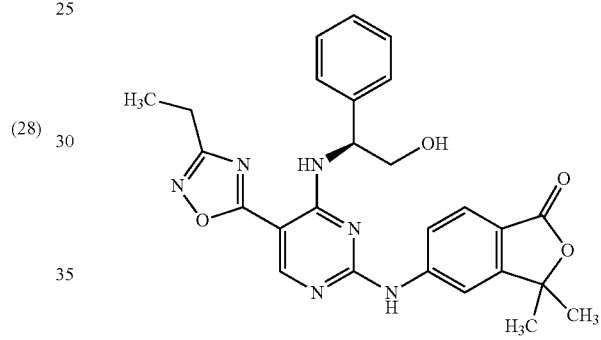

Example 29 was prepared according to the general preparation procedure for 5-[(4-{[(1S)-2-hydroxy-1-phenylethyl] amino}-5-(3-methyl-1,2,4-oxadiazol-5-yl)pyrimidin-2-yl) amino]-3,3-dimethyl-1,3-dihydro-2-benzofuran-1-one using N-hydroxypropionimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to afford 5-{[5-(3-ethyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (10.5 mg, 32.2% yield). HPLC $t_R$: 1.87 min; LC/MS Condition 3. ES [MS] m/z: 487.1 [M+H]$^+$. $^1$H NMR (500 MHz, DMSO-d$_6$) δ 9.19 (d, J=8.1 Hz, 1H), 8.83 (s, 1H), 7.99 (s, 1H), 7.72 (d, J=8.4 Hz, 1H), 7.66 (d, J=8.4 Hz, 1H), 7.45-7.41 (m, 2H), 7.41-7.36 (m, 2H), 7.31-7.26 (m, 1H), 5.40 (d, J=7.3 Hz, 1H), 5.26 (t, J=5.0 Hz, 1H), 3.96-3.90 (m, 1H), 3.85 (dt, J=10.4, 4.9 Hz, 1H), 2.83 (q, J=7.6 Hz, 2H), 1.59 (s, 3H), 1.54 (s, 3H), 1.33 (t, J=7.5 Hz, 3H).

Example 30

5-{[5-(3-cyclopropyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one

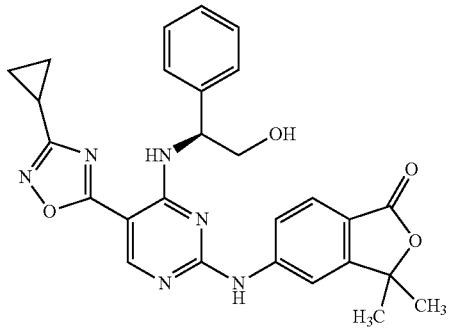

(30)

Example 30 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxycyclopropanecarboximidamide. The crude material was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 33-73% B over 23 minutes, then a 2-minute hold at 100% B; Flow: 20 mL/min to afford 5-{[5-(3-cyclopropyl-1,2,4-oxadiazol-5-yl)-4-{[(1S)-2-hydroxy-1-phenylethyl]amino}pyrimi- din-2-yl]amino}-3,3-dimethyl-1,3-dihydro-2-benzofuran-1-one (10.3 mg, 38.2% yield). HPLC $t_R$: 1.99 min; LC/MS Condition 2. ES [MS] m/z: 499.1 [M+H]$^+$. $^1$H NMR (500 MHz, DMSO-$d_6$) δ 10.41 (s, 1H), 9.16 (d, J=7.7 Hz, 1H), 8.79 (s, 1H), 7.99 (s, 1H), 7.71 (d, J=8.4 Hz, 1H), 7.65 (d, J=8.4 Hz, 1H), 7.42-7.36 (m, 4H), 7.30-7.26 (m, 1H), 5.37-5.32 (m, 1H), 5.24 (t, J=4.8 Hz, 1H), 3.91 (dt, J=10.6, 5.0 Hz, 1H), 3.87-3.81 (m, 1H), 2.26-2.19 (m, 1H), 1.58 (s, 3H), 1.53 (s, 3H), 1.19-1.07 (m, 4H), 1.02-0.97 (m, 1H).

Example 31

5-[(4-{[(1S)-2-hydroxy-1-phenylethyl]amino}-5-[3-(morpholin-4-yl)-1,2,4-oxadiazol-5-yl]pyrimidin-2-yl)amino]-3,3-dimethyl-1,3-dihydro-2-benzofuran-1-one (31)

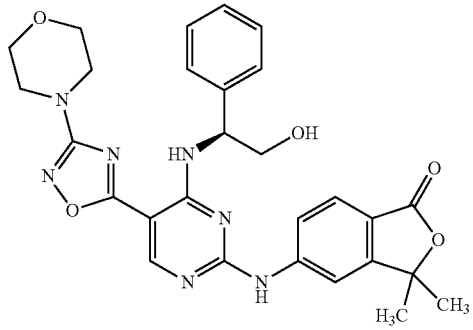

Example 31 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxymorpholine-4-carboximidamide. The crude reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min to afford 5-[(4-{[(1S)-2-hydroxy-1-phenylethyl]amino}-5-[3-(morpholin-4-yl)-1,2,4-oxadiazol-5-yl]pyrimidin-2-yl)amino]-3,3-dimethyl-1,3-dihydro-2-benzofuran-1-one (9.8 mg, 26.7% yield). HPLC $t_R$: 2.52 min; LC/MS Condition 2. ES [MS] m/z: 544.1 [M+H]$^+$. $^1$H NMR (500 MHz, DMSO-$d_6$) δ 10.40 (br. s., 1H), 9.24 (d, J=7.3 Hz, 1H), 8.76 (s, 1H), 7.95 (s, 1H), 7.70 (d, J=8.4 Hz, 1H), 7.64 (d, J=8.4 Hz, 1H), 7.43-7.35 (m, 4H), 7.30-7.24 (m, 1H), 5.33 (br. s., 1H), 5.28 (t, J=4.6 Hz, 1H), 3.98-3.91 (m, 1H), 3.91-3.85 (m, 1H), 3.74 (t, J=4.6 Hz, 3H), 3.47-3.36 (m, 1H), 1.58 (s, 3H), 1.52 (s, 3H).

Example 32

5-[(4-{[(1S)-2-hydroxy-1-phenylethyl]amino}-5-{3-[(morpholin-4-yl)methyl]-1,2,4-oxadiazol-5-yl}pyrimidin-2-yl)amino]-3,3-dimethyl-1,3-dihydro-2-benzofuran-1-one (32)

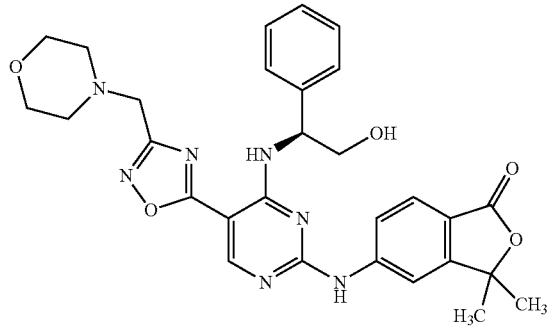

Example 32 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxy-2-morpholinoacetimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to afford 5-[(4-{[(1S)-2-hydroxy-1-phenylethyl]amino}-5-{3-[(morpholin-4-yl)methyl]-1,2,4-oxadiazol-5-yl}pyrimidin-2-yl) amino]-3,3-dimethyl-1,3-dihydro-2-benzofuran-1-one (15.5 mg, 48.9% yield). HPLC $t_R$: 1.29 min; LC/MS Condition 3. ES [MS] m/z: 558.2 [M+H]$^+$. $^1$H NMR (500 MHz, DMSO-$d_6$) δ 10.46 (br. s., 1H), 9.08 (d, J=7.7 Hz, 1H), 8.85 (s, 1H), 8.03 (s, 1H), 7.72 (d, J=8.8 Hz, 1H), 7.67 (d, J=8.4 Hz, 1H), 7.43 (d, J=7.7 Hz, 2H), 7.38 (t, J=7.5 Hz, 2H), 7.32-7.26 (m, 1H), 5.42 (d, J=7.3 Hz, 1H), 5.22 (t, J=5.0 Hz, 1H), 3.92 (dt, J=10.5, 5.0 Hz, 1H), 3.86-3.82 (m, 1H), 3.80 (s, 2H), 3.60 (t, J=4.4 Hz, 3H), 2.61 (br. s., 4H), 1.60 (s, 3H), 1.56 (s, 3H).

Example 33

5-[(4-{[(1S)-2-hydroxy-1-phenylethyl]amino}-5-[3-(oxan-4-yl)-1,2,4-oxadiazol-5-yl]pyrimidin-2-yl)amino]-3,3-dimethyl-1,3-dihydro-2-benzofuran-1-one

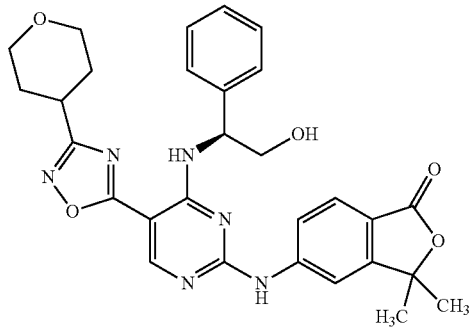

(33)

Example 33 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxytetrahydro-2H-pyran-4-carboximidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-70% B over 20 minutes, then a 5-minute hold at 100% B; Flow: 20 mL/min to afford 5-[(4-{[(1S)-2-hydroxy-1-phenylethyl]amino}-5-[3-(oxan-4-yl)-1,2,4-oxadiazol-5-yl]pyrimidin-2-yl)amino]-3,3-dimethyl-1,3-dihydro-2-benzofuran-1-one (6.7 mg, 19.4%). HPLC $t_R$: 1.79 min; LC/MS Condition 3. ES [MS] m/z: 543.1 [M+H]⁺. ¹H NMR (500 MHz, DMSO-d₆) δ 9.25 (d, J=7.3 Hz, 1H), 8.83 (s, 1H), 8.00 (s, 1H), 7.72 (d, J=7.7 Hz, 1H), 7.66 (d, J=8.4 Hz, 1H), 7.45-7.41 (m, 2H), 7.41-7.36 (m, 2H), 7.31-7.26 (m, 1H), 5.38 (d, J=7.7 Hz, 1H), 5.27 (t, J=4.8 Hz, 1H), 3.97-3.90 (m, 3H), 3.89-3.83 (m, 1H), 3.56-3.49 (m, 1H), 3.26-3.16 (m, 1H), 1.98 (d, J=13.2 Hz, 2H), 1.90-1.76 (m, 2H), 1.59 (s, 3H), 1.54 (s, 3H).

Example 34

5-[(4-{[(1S)-2-hydroxy-1-phenylethyl]amino}-5-[3-(propan-2-yl)-1,2,4-oxadiazol-5-yl]pyrimidin-2-yl)amino]-3,3-dimethyl-1,3-dihydro-2-benzofuran-1-one

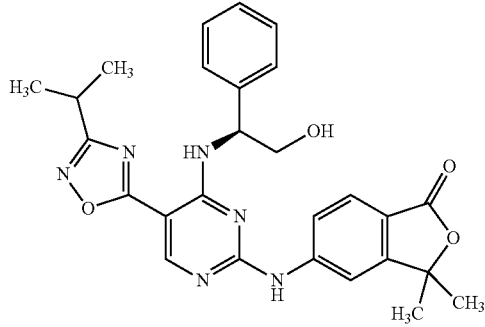

(34)

Example 34 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxyisobutyrimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min to afford 5-[(4-{[(1S)-2-hydroxy-1-phenylethyl]amino}-5-[3-(propan-2-yl)-1,2,4-oxadiazol-5-yl]pyrimidin-2-yl)amino]-3,3-dimethyl-1,3-dihydro-2-benzofuran-1-one (27.8 mg, 89% yield). HPLC $t_R$: 1.93 min; LC/MS Condition 4. ES [MS] m/z: 501.3 [M+H]⁺. ¹H NMR (500 MHz, DMSO-d₆) δ 10.43 (br. s., 1H), 9.28 (d, J=7.3 Hz, 1H), 8.82 (s, 1H), 8.02 (s, 1H), 7.71 (d, J=8.4 Hz, 1H), 7.66 (d, J=8.4 Hz, 1H), 7.45-7.42 (m, 2H), 7.41-7.36 (m, 2H), 7.31-7.26 (m, 1H), 5.39 (d, J=7.3 Hz, 1H), 5.24 (t, J=5.0 Hz, 1H), 3.96-3.90 (m, 1H), 3.89-3.82 (m, 1H), 3.18 (quin, J=6.9 Hz, 1H), 1.59 (s, 3H), 1.55 (s, 3H), 1.36 (dd, J=6.8, 4.6 Hz, 6H).

Example 35

5-[(4-{[(1S)-2-hydroxy-1-phenylethyl]amino}-5-(3-propyl-1,2,4-oxadiazol-5-yl)pyrimidin-2-yl)amino]-3,3-dimethyl-1,_3-dihydro-2-benzofuran-1-one

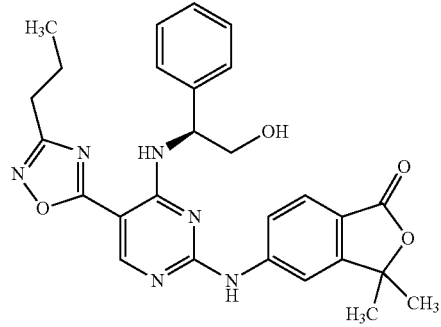

(35)

Example 35 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxybutyrimidamide and with heating in the microwave for 0.25 h at 140° C. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 38-78% B over 22 minutes. ¹H NMR (500 MHz, DMSO-d₆) δ 10.42 (br. s., 1H), 9.17 (d, J=7.7 Hz, 1H), 8.83 (s, 1H), 8.00 (s, 1H), 7.72 (d, J=8.4 Hz, 1H), 7.66 (d, J=8.1 Hz, 1H), 7.44-7.35 (m, 4H), 7.30-7.26 (m, 1H), 5.39 (br. s., 1H), 5.24 (t, J=4.8 Hz, 1H), 3.95-3.89 (m, 1H), 3.87-3.81 (m, 1H), 3.38 (s, 1H), 2.79 (t, J=7.3 Hz, 2H), 1.84-1.76 (m, 2H), 1.59 (s, 3H), 1.54 (s, 3H), 0.99 (t, J=7.3 Hz, 3H).

Example 36

5-{[5-(3-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one

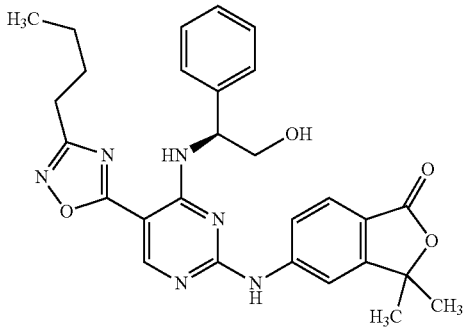

(36)

Example 36 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxypentaimidamide and with heating in the microwave for 0.25 h at 140° C. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 20 minutes, then a 5-minute hold at 100% B; Flow: 20 mL/min to afford 5-{[5-(3-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (6.7 mg, 24.1% yield). HPLC $t_R$: 2.00 min; LC/MS Condition 3. ES [MS] m/z: 515.2 [M+H]$^+$. $^1$H NMR (500 MHz, DMSO-d$_6$) δ 10.43 (br. s., 1H), 9.17 (d, J=7.3 Hz, 1H), 8.83 (s, 1H), 8.02 (s, 1H), 7.72 (d, J=8.4 Hz, 1H), 7.66 (d, J=8.4 Hz, 1H), 7.44-7.41 (m, 2H), 7.40-7.36 (m, 2H), 7.32-7.26 (m, 1H), 5.40 (d, J=7.3 Hz, 1H), 3.96-3.89 (m, 1H), 3.88-3.80 (m, 1H), 2.81 (t, J=7.3 Hz, 2H), 1.76 (quin, J=7.3 Hz, 2H), 1.59 (s, 3H), 1.55 (s, 3H), 1.41 (sxt, J=7.6 Hz, 2H), 0.94 (t, J=7.3 Hz, 3H).

Example 37

5-[(4-{[(1S)-2-hydroxy-1-phenylethyl]amino}-5-[3-(6-hydroxy-2-methylhexan-2-yl)-1,2,4-oxadiazol-5-yl]pyrimidin-2-yl)amino]-3,3-dimethyl-1,3-dihydro-2-benzofuran-1-one

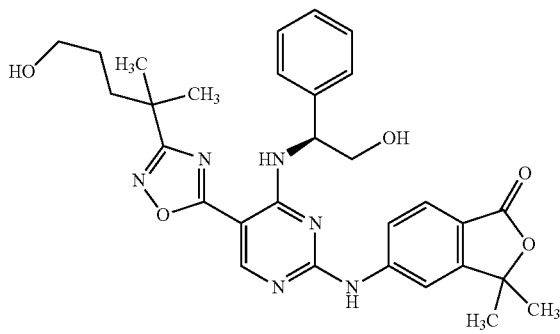

(37)

Example 37 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N,6-dihydroxy-2,2-dimethylhexanimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 38-78% B over 19 minutes, then a 4-minute hold at 100% B; Flow: 20 mL/min to afford 5-[(4-{[(1S)-2-hydroxy-1-phenylethyl]amino}-5-[3-(6-hydroxy-2-methylhexan-2-yl)-1,2,4-oxadiazol-5-yl]pyrimidin-2-yl)amino]-3,3-dimethyl-1,3-dihydro-2-benzofuran-1-one (23.1 mg, 70.1% yield). HPLC $t_R$: 1.86 min; LC/MS Condition 3. ES [MS] m/z: 573.1 [M+H]$^+$. $^1$H NMR (500 MHz, DMSO-d$_6$) δ 9.37 (d, J=7.7 Hz, 1H), 8.81 (s, 1H), 8.03 (s, 1H), 7.74 (d, J=8.8 Hz, 1H), 7.68 (d, J=8.4 Hz, 1H), 7.44-7.41 (m, 2H), 7.41-7.36 (m, 2H), 7.31-7.26 (m, 1H), 5.38 (br. s., 1H), 5.26-5.21 (m, 1H), 4.39-4.35 (m, 1H), 3.97-3.89 (m, 1H), 3.87-3.80 (m, 1H), 3.44-3.33 (m, 1H), 1.72 (br. s., 2H), 1.61 (s, 3H), 1.57 (s, 3H), 1.38 (d, J=2.6 Hz, 8H), 1.21 (d, J=7.3 Hz, 2H).

Example 38

5-[(4-{[(1S)-2-hydroxy-1-phenylethyl]amino}-5-{3-[1-(hydroxymethyl)cyclopropyl]-1,2,4-oxadiazol-5-yl}pyrimidin-2-yl)amino]-3,3-dimethyl-1,3-dihydro-2-benzofuran-1-one

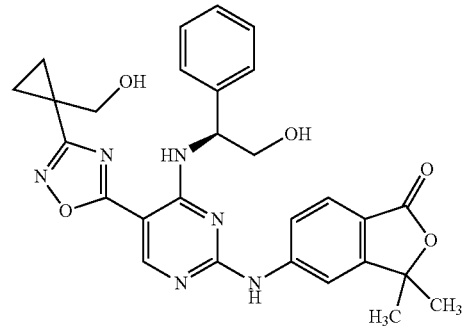

(38)

Example 38 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxy-1-(hydroxymethyl)cyclopropanecarboximidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 16 minutes, then a 5-minute hold at 100% B; Flow: 20 mL/min to afford 5-[(4-{[(1S)-2-hydroxy-1-phenylethyl]amino}-5-{3-[1-(hydroxymethyl)cyclopropyl]-1,2,4-oxadiazol-5-yl}pyrimidin-2-yl)amino]-3,3-dimethyl-1,3-dihydro-2-benzofuran-1-one (15.5 mg, 47% yield). HPLC $t_R$: 1.69 min; LC/MS Condition 2. ES [MS] m/z: 529.1 [M+H]$^+$. $^1$H NMR (500 MHz, DMSO-d$_6$) δ 9.22 (d, J=7.7 Hz, 1H), 8.80 (s, 1H), 8.00 (s, 1H), 7.73-7.69 (m, 1H), 7.67-7.64 (m, 1H), 7.43-7.36 (m, 4H), 7.31-7.26 (m, 1H), 5.36 (d, J=7.3 Hz, 1H), 5.25 (t, J=4.8 Hz, 1H), 4.91 (t, J=5.9 Hz, 1H), 3.95-3.89 (m, 1H), 3.84 (d, J=5.9 Hz, 3H), 1.59 (s, 3H), 1.54 (s, 3H), 1.29-1.22 (m, 1H), 1.18-1.11 (m, 3H).

Example 39

5-{[5-(3-tert-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one

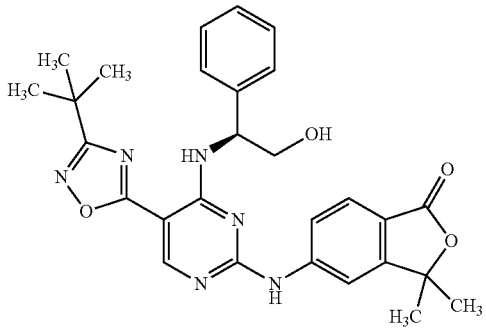

(39)

Example 39 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxypivalimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 42-82% B over 19 minutes, then a 4-minute hold at 100% B; Flow: 20 mL/min to afford 5-{[5-(3-tert-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (15.2 mg, 54.6%). HPLC $t_R$: 2.15 min; LC/MS Condition 3. ES [MS] m/z: 515.1 [M+H]$^+$. $^1$H NMR (500 MHz, DMSO-d$_6$) δ 9.35 (d, J=7.7 Hz, 1H), 8.80 (s, 1H), 8.02 (s, 1H), 7.72-7.64 (m, 2H), 7.44-7.35 (m, 4H), 7.28 (t, J=7.2 Hz, 1H), 5.37 (br d, J=7.3 Hz, 1H), 5.23 (t, J=4.8 Hz, 1H), 3.92 (dd, J=10.8, 5.7 Hz, 1H), 3.87-3.82 (m, 1H), 1.59 (s, 3H), 1.54 (s, 3H), 1.40 (s, 9H).

Example 40

5-({5-[3-(3,3-difluorocyclobutyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one

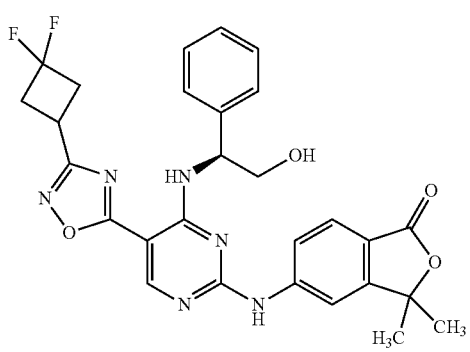

(40)

Example 40 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using (Z)-3,3-difluoro-N'-hydroxycyclobutanecarboximidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min to afford 5-({5-[3-(3,3-difluorocyclobutyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one (6 mg, 16.9% yield). HPLC $t_R$: 2.14 min; LC/MS Condition 3. ES [MS] m/z: 549.03 [M+H]$^+$. $^1$H NMR (500 MHz, DMSO-d$_6$) δ 10.46 (br s, 1H), 9.15 (br d, J=7.7 Hz, 1H), 8.84 (s, 1H), 8.04 (s, 1H), 7.73-7.64 (m, 2H), 7.45-7.35 (m, 4H), 7.30-7.25 (m, 1H), 5.38 (br s, 1H), 5.23 (t, J=5.0 Hz, 1H), 3.93-3.87 (m, 1H), 3.87-3.80 (m, 1H), 3.71 (br s, 1H), 3.36 (br d, J=5.9 Hz, 1H), 3.34-2.88 (m, 4H), 1.59 (s, 3H), 1.55 (s, 3H).

Example 41

(S)-5-((4-((2-hydroxy-1-phenylethyl)amino)-5-(3-(1-hydroxy-2-methylpropan-2-yl)-1,2,4-oxadiazol-5-yl)pyrimidin-2-yl)amino)-3,3-dimethylisobenzofuran-1(3H)-one

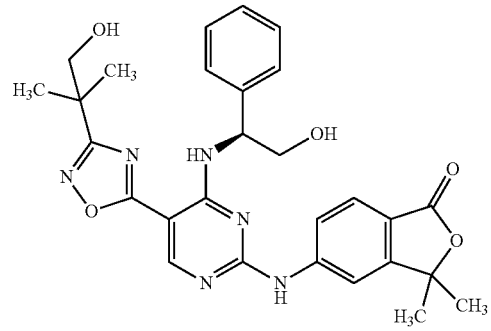

(41)

Preparation 41A: (S)-ethyl 4-((2-((tert-butyldimethylsilyl)oxy)-1-phenylethyl)amino)-2-((3,3-dimethyl-1-oxo-1,3-dihydroisobenzofuran-5-yl)amino)pyrimidine-5-carboxylate

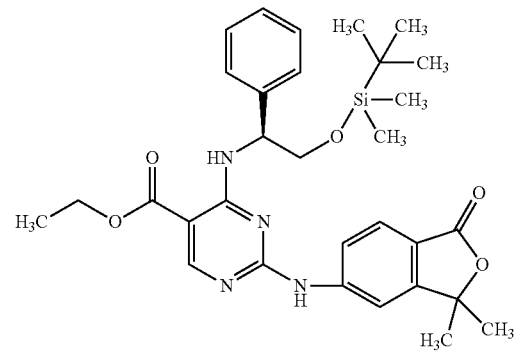

(41A)

To a 100 mL round bottom flask equipped with a stir bar and charged with an ice-cooled solution of (S)-ethyl 2-((3,3-dimethyl-1-oxo-1,3-dihydroisobenzofuran-5-yl) amino)-4-((2-hydroxy-1-phenylethyl) amino)pyrimidine-5-carboxylate (200.0 mg, 0.432 mmol) and tert-butylchlorodimethylsilane (71.7 mg, 0.476 mmol) in DCM (20 mL) was added 1H-imidazole (88 mg, 1.297 mmol). The resulting mixture was stirred for 5 minutes and the ice-water bath was removed and stirring was continued at room temperature. After 18 h, the reaction was not complete and additional 1H-imidazole (88 mg, 1.297 mmol) along with 2.0 equivalents of tert-butylchlorodimethylsilane (143.4 mg, 0.952 mmol) were added. After 1 h at room temperature, the reaction mixture was diluted with DCM and water, and then stirred vigorously. The organic layer was separated and the aqueous layer extracted once more with DCM. The combined organic layers were dried over MgSO$_4$, filtered through a thin pad of silica gel (about 2 cm) and concentrated. The crude material was purified by silica gel chromatography eluting with a gradient from 10 to 70% EtOAc in hexanes to afford (S)-ethyl 4-((2-((tert-butyldimethylsilyl)oxy)-1-phenylethyl)amino)-2-((3,3-dimethyl-1-oxo-1,3-dihydroisobenzofuran-5-yl)amino)pyrimidine-5-carboxylate (221.0 mg, 0.383 mmol, 89% yield) as a pale yellow solid. ES [MS] m/z: 577.2 [M+H]$^+$. $^1$H NMR (400 MHz, CDCl$_3$) δ 9.21 (br d, J=7.5 Hz, 1H), 8.73 (s, 1H), 7.72 (d, J=8.5 Hz, 1H), 7.60 (s, 1H), 7.57-7.50 (m, 2H), 7.42-7.30 (m, 5H), 5.39-5.33 (m, 1H), 4.45-4.35 (m, 2H), 4.04 (dd, J=4.5, 10.3 Hz, 1H), 3.92 (dd, J=5.1, 10.2 Hz, 1H), 2.07 (s, 1H), 1.69-1.57 (m, 6H), 1.42 (t, J=7.0 Hz, 3H), 0.96-0.81 (m, 9H), −0.10 (s, 3H).

Preparation 41B: (S)-5-((4-((2-((tert-butyldimethylsilyl)oxy)-1-phenylethyl)amino)-5-(3-(1-((tert-butyldimethylsilyl)oxy)-2-methylpropan-2-yl)-1,2,4-oxadiazol-5-yl)pyrimidin-2-yl)amino)-3,3-dimethylisobenzofuran-1(3H)-one (41B)

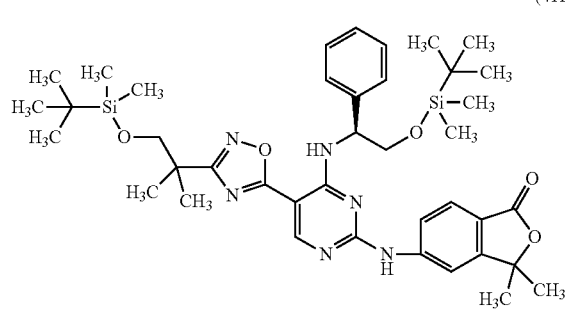

A vial was charged with (S)-ethyl 4-((2-((tert-butyldimethylsilyl)oxy)-1-phenylethyl)amino)-2-((3,3-dimethyl-1-oxo-1,3-dihydroisobenzofuran-5-yl)amino) pyrimidine-5-carboxylate (70.0 mg, 0.121 mmol), 3-((tert-butyldimethylsilyl)oxy)-N-hydroxy-2,2-dimethylpropanimidamide (120 mg, 0.485 mmol), and molecular sieves (3 Å, freshly activated, 80 mg). The vial was flushed with nitrogen and anhydrous EtOH (3 mL) was added. After stirring for 5 min, the mixture was treated with sodium ethanolate (0.291 mL, 0.728 mmol) and the vial was sealed and placed in a 70° C. bath. After 20 h, the reaction mixture was cooled to room temperature, diluted with EtOAc, and washed with brine. The organic layer was separated, dried over MgSO$_4$, filtered and concentrated.

Example 41

To a stirring solution of (S)-5-((4-((2-((tert-butyldimethylsilyl)oxy)-1-phenylethyl)amino)-5-(3-(1-((tert-butyldimethylsilyl)oxy)-2-methylpropan-2-yl)-1,2,4-oxadiazol-5-yl) pyrimidin-2-yl)amino)-3,3-dimethylisobenzofuran-1(3H)-one (74.0 mg, 0.097 mmol) in THF at 0° C. was added TBAF (0.49 mL, 0.49 mmol, 1 M solution in THF). After 10 min, the ice bath was removed and stirring was continued at room temperature. After 2 h, the reaction was quenched with a saturated aqueous solution of NH$_4$Cl and diluted with EtOAc. The organic layer was separated, filtered and concentrated prior to purification via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 25-65% B over 25 minutes, then a 5-minute hold at 100% B; Flow: 20 mL/min to afford (S)-5-((4-((2-hydroxy-1-phenylethyl) amino)-5-(3-(1-hydroxy-2-methylpropan-2-yl)-1,2,4-oxadiazol-5-yl)pyrimidin-2-yl) amino)-3,3-dimethylisobenzofuran-1(3H)-one (19.5 mg, 37.7% yield). HPLC t$_R$: 1.61 min; LC/MS Condition 3. ES [MS] m/z: 531.2 [M+H]$^+$. $^1$H NMR (500 MHz, DMSO-d$_6$) δ 8.71 (s, 1H), 8.00 (s, 1H), 7.71 (br d, J=8.44 Hz, 1H), 7.64 (d, J=8.07 Hz, 1H), 7.35-7.41 (m, 4H), 7.27 (t, J=6.45 Hz, 1H), 5.30-5.36 (m, 1H), 4.04 (s, 1H), 3.86 (br dd, J=9.90, 5.14 Hz, 1H), 3.78 (dt, J=10.73, 5.46 Hz, 1H), 1.59 (s, 3H), 1.54 (s, 3H), 1.31 (br d, J=4.03 Hz, 6H).

Example 42

5-[(4-{[(1S)-2-hydroxy-1-phenylethyl]amino}-5-[3-(pyridin-2-yl)-1,2,4-oxadiazol-5-yl]pyrimidin-2-yl) amino]-3,3-dimethyl-1,3-dihydro-2-benzofuran-1-one (42)

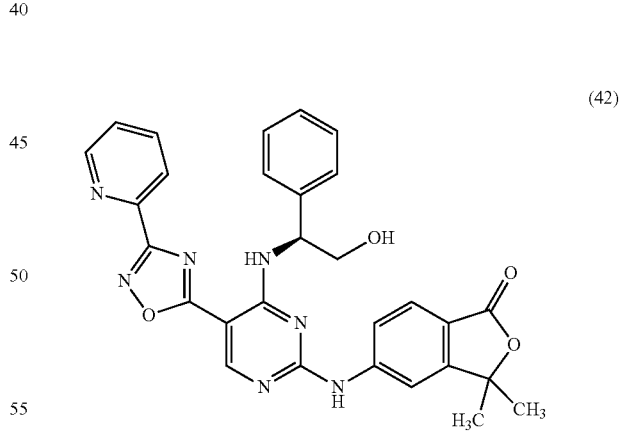

Example 42 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxypicolinimidamide. The compound was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 34-74% B over 19 minutes, then a 4-minute hold at 100% B; Flow: 20 mL/min. Fractions containing the product were combined and dried via centrifugal evaporation to afford 5-[(4-{[(1S)-2-hydroxy-1-phenylethyl]amino}-5-[3-(pyridin-2-yl)-1,2,4-oxadiazol-5-yl]pyrimidin-2-yl)amino]-3,3-dimethyl-1,3-dihydro-2-benzofuran-1-one (2.1 mg, 7.3% yield). HPLC $t_R$: 1.80 min; LC/MS Condition 2. ES [MS] m/z: 536.1 [M+H]⁺. ¹H NMR (500 MHz, DMSO-$d_6$) δ 10.48 (br. s., 1H), 9.41 (d, J=7.0 Hz, 1H), 8.94 (s, 1H), 8.83 (d, J=3.3 Hz, 1H), 8.25 (d, J=7.7 Hz, 1H), 8.10-8.06 (m, 1H), 7.99 (s, 1H), 7.73 (d, J=9.5 Hz, 1H), 7.70-7.64 (m, 3H), 7.49 (d, J=7.7 Hz, 2H), 7.41 (d, J=7.3 Hz, 2H), 7.29 (t, J=7.5 Hz, 1H), 4.03-3.98 (m, 1H), 3.97-3.91 (m, 1H), 3.43 (br. s., 1H), 1.60 (s, 3H), 1.53 (s, 3H).

Example 43

5-[(4-{[(1S)-2-hydroxy-1-phenylethyl]amino}-5-[3-(pyridin-3-yl)-1,2,4-oxadiazol-5-yl]pyrimidin-2-yl)amino]-3,3-dimethyl-1,3-dihydro-2-benzofuran-1-one

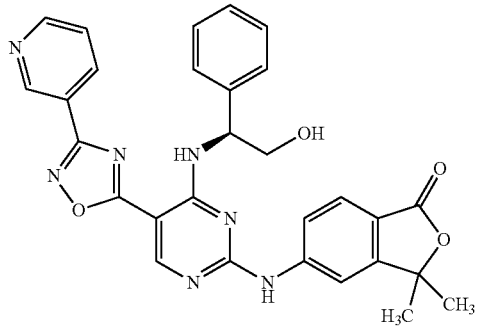

(43)

Example 43 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using N-hydroxynicotinimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the product were combined and dried via centrifugal evaporation to afford 5-[(4-{[(1S)-2-hydroxy-1-phenylethyl]amino}-5-[3-(pyridin-3-yl)-1,2,4-oxadiazol-5-yl]pyrimidin-2-yl)amino]-3,3-dimethyl-1,3-dihydro-2-benzofuran-1-one (10.4 mg, 34.5% yield). HPLC $t_R$; 1.55 min; LC/MS Condition 3. ES [MS] m/z: 536.1 [M+H]⁺. ¹H NMR (500 MHz, DMSO-$d_6$) δ 10.49 (br. s., 1H), 9.43 (d, J=7.7 Hz, 1H), 9.33 (s, 1H), 8.93 (s, 1H), 8.84 (d, J=4.8 Hz, 1H), 8.49 (d, J=7.7 Hz, 1H), 7.95 (s, 1H), 7.73 (d, J=8.8 Hz, 1H), 7.69-7.63 (m, 2H), 7.48 (d, J=7.7 Hz, 2H), 7.39 (t, J=7.7 Hz, 2H), 7.31-7.25 (m, 1H), 5.46-5.38 (m, 2H), 4.05-3.93 (m, 2H), 1.59 (s, 3H), 1.52 (s, 3H).

Example 44

5-({5-[3-(4-fluorophenyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one

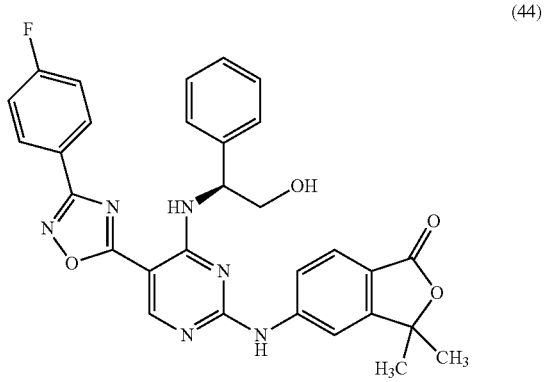 [SMILES: CC1(C)OC(=O)c2ccc(Nc3ncc(-c4nc(-c5ccc(F)cc5)no4)c(N[C@H](CO)c4ccccc4)n3)cc21]

(44)

Example 44 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using 4-fluoro-N-hydroxybenzimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min to afford 5-({5-[3-(4-fluorophenyl)-1,2,4-oxadiazol-5-yl]-4-{[(1S)-2-hydroxy-1-phenylethyl]amino} pyrimidin-2-yl}amino)-3,3-dimethyl-1,3-dihydro-2-benzofuran-1-one (7.7 mg, 31.9% yield). HPLC $t_R$: 2.1 min; LC/MS Condition 5. ES [MS] m/z: 553.2 [M+H]⁺. ¹H NMR (500 MHz, DMSO-$d_6$) δ 9.44 (d, J=7.3 Hz, 1H), 8.91 (s, 1H), 8.21 (dd, J=8.6, 5.3 Hz, 2H), 7.97 (s, 1H), 7.73 (d, J=7.7 Hz, 1H), 7.65 (d, J=8.4 Hz, 1H), 7.50-7.44 (m, 4H), 7.40 (t, J=7.7 Hz, 2H), 7.31-7.26 (m, 1H), 5.43-5.38 (m, 2H), 4.04-3.99 (m, 1H), 3.98-3.92 (m, 1H), 1.59 (s, 3H), 1.53 (s, 3H).

Example 45

5-({5-[3-(3-fluorophenyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one

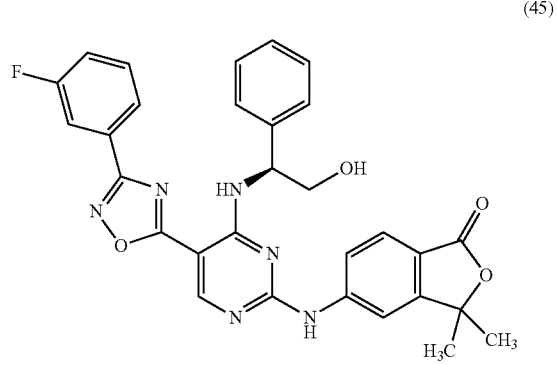 [SMILES: CC1(C)OC(=O)c2ccc(Nc3ncc(-c4nc(-c5cccc(F)c5)no4)c(N[C@H](CO)c4ccccc4)n3)cc21]

(45)

Example 45 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using 3-fluoro-N-hydroxybenzimidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 48-88% B over 19 minutes, then a 4-minute hold at 100% B; Flow: 20 mL/min to afford 5-({5-[3-(3-fluorophenyl)-1,2,4-oxadiazol-5-yl]-4-{[(1S)-2-hydroxy-1-phenylethyl]amino} pyrimidin-2-yl}amino)-3,3-dimethyl-1,3-dihydro-2-benzofuran-1-one (11.2 mg, 36.4% yield). HPLC $t_R$: 2.09 min; LC/MS Condition 3. ES [MS] m/z: 553.1 [M+H]⁺. ¹H NMR (500 MHz, DMSO-d₆) δ 10.49 (br. s., 1H), 9.45 (d, J=7.3 Hz, 1H), 8.92 (s, 1H), 8.01 (d, J=8.1 Hz, 1H), 7.97 (s, 1H), 7.91 (d, J=8.8 Hz, 1H), 7.75-7.64 (m, 3H), 7.55-7.51 (m, 1H), 7.48 (d, J=7.7 Hz, 2H), 7.40 (t, J=7.7 Hz, 2H), 7.31-7.26 (m, 1H), 5.45-5.37 (m, 2H), 4.06-3.93 (m, 2H), 3.39 (s, 1H), 1.59 (s, 3H), 1.52 (s, 3H).

Example 46

5-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-3,3-dimethyl-1,3-dihydro-2-benzofuran-1-one (46)

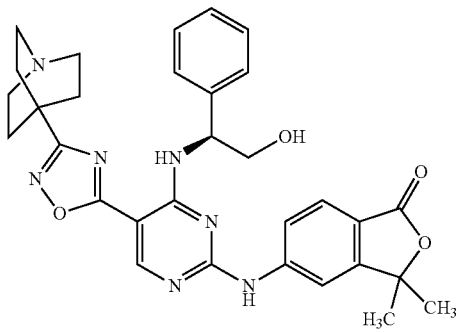

Example 46 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using (Z)—N'-hydroxyquinuclidine-4-carboximidamide. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 14-54% B over 22 minutes, then a 4-minute hold at 100% B; Flow: 20 mL/min to afford 5-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-3,3-dimethyl-1,3-dihydro-2-benzofuran-1-one (6.4 mg, 23.1% yield). HPLC $t_R$: 1.20 min; LC/MS Condition 3. ES [MS] m/z: 567.2 [M+H]⁺. ¹H NMR (500 MHz, DMSO-d₆) δ 8.81-8.70 (m, 1H), 8.68-8.53 (m, 1H), 7.83-7.68 (m, 1H), 7.49 (br d, J=8.1 Hz, 2H), 7.38-7.30 (m, 4H), 7.29-7.23 (m, 1H), 6.04-5.99 (m, 1H), 4.70-4.57 (m, 1H), 3.85 (dd, J=10.6, 4.4 Hz, 1H), 3.05-2.87 (m, 6H), 1.98-1.88 (m, 6H), 1.82 (br s, 2H), 1.47 (br d, J=7.0 Hz, 6H).

Example 47

5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (47)

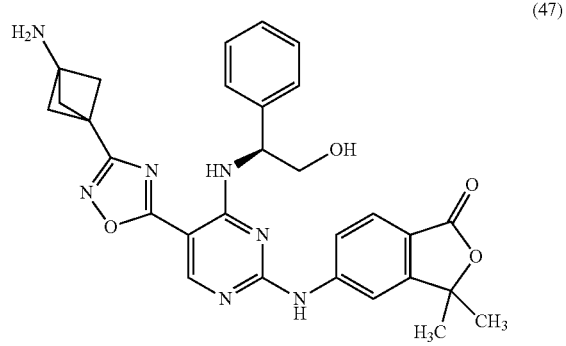 [SMILES: CC1(C)OC(=O)c2ccc(Nc3ncc(-c4nc(C56CC(N)(C5)C6)no4)c(N[C@H](CO)c4ccccc4)n3)cc21]

Example 47 was prepared according to the general preparation procedure for 5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one using tert-butyl (3-(N-hydroxycarbamimidoyl)bicyclo[1.1.1]pentan-1-yl)carbamate. To a stirring solution of the intermediate (S)-tert-butyl (3-(5-(2-((3,3-dimethyl-1-oxo-1,3-dihydroisobenzofuran-5-yl) amino)-4-((2-hydroxy-1-phenylethyl)amino)pyrimidin-5-yl)-1,2,4-oxadiazol-3-yl) bicyclo[1.1.1]pentan-1-yl)carbamate (30.0 mg, 0.047 mmol) in 1,4-dioxane (10 mL) at 0° C. was added a 4 M solution of HCl in dioxane (0.117 mL, 0.469 mmol). After 2 hours, the reaction mixture was concentrated to dryness, and dissolved in 5 mL of methanol. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the product were combined and dried via centrifugal evaporation to afford 5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (7.7 mg, 29.5% yield). HPLC $t_R$: 1.29 min; LC/MS Condition 3. ES [MS] m/z: 540.2 [M+H]⁺. ¹H NMR (500 MHz, DMSO-d₆) δ 9.22 (d, J=7.7 Hz, 1H), 8.80 (s, 1H), 8.08 (s, 1H), 7.68 (q, J=8.2 Hz, 2H), 7.46-7.38 (m, 4H), 7.33-7.28 (m, 1H), 5.36 (d, J=7.3 Hz, 1H), 3.92 (d, J=5.5 Hz, 1H), 3.85 (dd, J=11.0, 4.8 Hz, 1H), 2.14 (s, 5H), 1.92 (s, 2H), 1.60 (s, 3H), 1.56 (s, 3H).

Example 48

5-[(5-{3-[3-(dimethylamino)bicyclo[1.1.1]pentan-1-yl]-1,2,4-oxadiazol-5-yl}-4-{[(1S)-2-hydroxy-1-phenylethyl]amino}pyrimidin-2-yl)amino]-3,3-dimethyl-1,3-dihydro-2-benzofuran-1-one

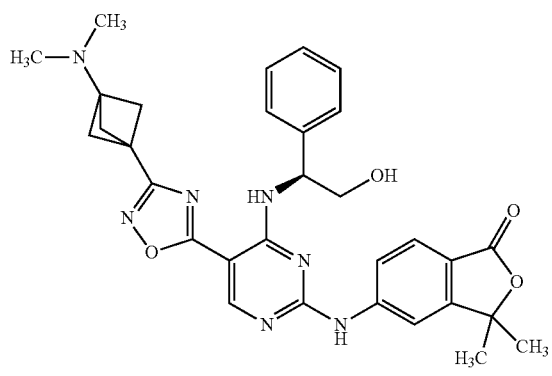

(48)

To a stirring solution of 5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (30.0 mg, 0.056 mmol) in acetonitrile (5 mL) at room temperature was added formaldehyde (66.8 mg, 2.224 mmol) and sodium cyanoborohydride (10.5 mg, 0.167 mmol) followed by acetic acid (0.15 mL). The reaction mixture was stirred for 3 h prior to quenching with a saturated aqueous solution of potassium bicarbonate. The reaction mixture was extracted with EtOAc (3×20 mL), and the combined organic layers were dried over magnesium sulfate, filtered and concentrated to dryness. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the product were combined and dried via centrifugal evaporation to afford 5-[(5-{3-[3-(dimethylamino)bicyclo[1.1.1]pentan-1-yl]-1,2,4-oxadiazol-5-yl}-4-{[(1S)-2-hydroxy-1-phenylethyl]amino}pyrimidin-2-yl)amino]-3,3-dimethyl-1,3-dihydro-2-benzofuran-1-one (13.8 mg, 43.3% yield). HPLC $t_R$: 1.42 min; LC/MS Condition 3. ES [MS] m/z: 568.1 [M+H]$^+$. $^1$H NMR (500 MHz, DMSO-$d_6$) δ 10.49 (br. s., 1H), 9.13 (d, J=7.7 Hz, 1H), 8.84 (s, 1H), 8.03 (s, 1H), 7.71 (d, J=8.8 Hz, 1H), 7.66 (d, J=8.1 Hz, 1H), 7.46-7.39 (m, 4H), 7.32-7.28 (m, 1H), 7.25 (s, 1H), 7.15 (s, 1H), 7.05 (s, 1H), 5.38 (d, J=7.0 Hz, 1H), 3.93 (dd, J=10.8, 4.2 Hz, 1H), 3.86 (dd, J=10.8, 5.0 Hz, 1H), 2.80 (s, 6H), 1.59 (s, 3H), 1.55 (s, 3H).

Example 49

N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl) bicyclo[1.1.1]penta-1-yl]acetamide

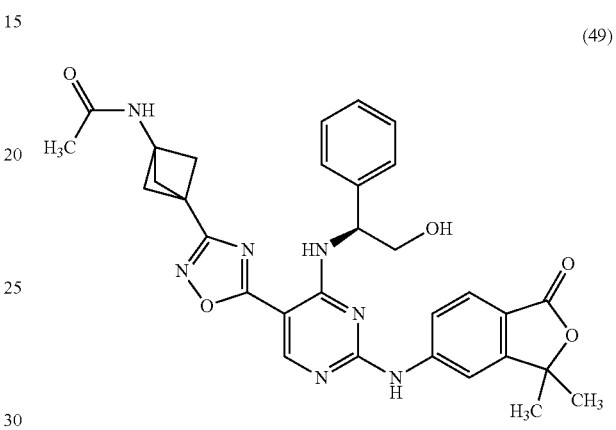

(49)

To a stirring solution of 5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (8.0 mg, 0.015 mmol) in 1,4-dioxane (1 mL) and DCM (0.5 mL) at 0° C. was added acetyl chloride (1.2 mg, 0.015 mmol) dissolved in 0.5 mL of DCM. The ice bath was removed after 5 minutes, and the reaction mixture was warmed to room temperature with stirring. After 75 minutes, the reaction mixture was concentrated to dryness, and dissolved in 2 mL of methanol, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 19 minutes, then a 4-minute hold at 100% B; Flow: 20 mL/min. Fractions containing the product were combined and dried via centrifugal evaporation to afford N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl)bicyclo[1.1.1]pentan-1-yl]acetamide (7.2 mg, 79% yield). HPLC $t_R$: 1.57 min; LC/MS Condition 3. ES [MS] m/z: 582.2 [M+H]$^+$. $^1$H NMR (500 MHz, DMSO-$d_6$) δ 9.13 (br d, J=7.7 Hz, 1H), 8.80 (s, 1H), 8.49 (s, 1H), 8.06 (s, 1H), 7.74 (dd, J=8.4, 1.8 Hz, 1H), 7.66 (d, J=8.4 Hz, 1H), 7.46-7.42 (m, 2H), 7.40 (t, J=7.0 Hz, 2H), 7.33-7.28 (m, 1H), 5.39 (dt, J=7.8, 4.7 Hz, 1H), 3.93 (dd, J=11.0, 4.4 Hz, 1H), 3.86 (dd, J=10.8, 5.0 Hz, 1H), 2.48-2.40 (m, 6H), 1.89 (s, 1H), 1.82 (s, 3H), 1.61 (s, 3H), 1.58 (s, 3H).

Example 50

Methyl N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl) bicyclo[1.1.1]pentan-1-yl]carbamate

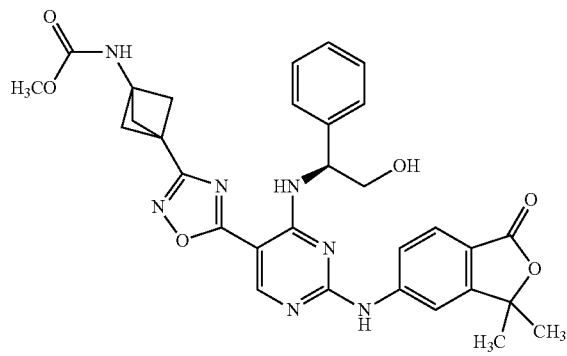

(50)

To a stirring solution of 5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (5.0 mg, 9.27 μmol) in 1,4-dioxane (1 mL) and DCM (0.5 mL) at 0° C. was added methyl carbonochloridate (0.88 mg, 9.27 μmol) dissolved in 0.5 mL of DCM. The ice bath was removed after 5 minutes and the reaction mixture was warmed to room temperature with stirring. After 45 minutes, the reaction mixture was concentrated to dryness, dissolved in 2 mL of methanol, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the product were combined and dried via centrifugal evaporation to afford methyl N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl)bicyclo[1.1.1]pentan-1-yl]carbamate (1.2 mg, 21.7% yield). HPLC $t_R$: 1.87 min; LC/MS Condition 2. ES [MS] m/z: 598.2 [M+H]$^+$. $^1$H NMR (500 MHz, DMSO-d$_6$) δ 9.13 (d, J=7.6 Hz, 1H), 8.83-8.78 (m, 1H), 8.05 (s, 1H), 7.94-7.88 (m, 1H), 7.74 (br d, J=8.4 Hz, 1H), 7.66 (d, J=8.4 Hz, 1H), 7.46-7.42 (m, 2H), 7.39 (t, J=7.0 Hz, 2H), 7.32-7.28 (m, 1H), 5.41-5.36 (m, 1H), 5.09 (t, J=4.6 Hz, 1H), 3.96-3.90 (m, 1H), 3.89-3.83 (m, 1H), 3.59-3.55 (m, 3H), 2.40 (s, 6H), 1.61 (s, 3H), 1.58 (s, 3H).

Example 51

2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide

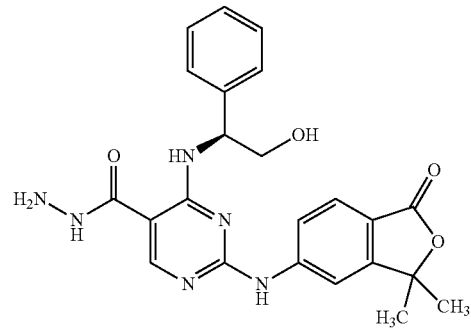

(51)

To a solution of (S)-ethyl 2-((3,3-dimethyl-1-oxo-1,3-dihydroisobenzofuran-5-yl) amino)-4-((2-hydroxy-1-phenylethyl)amino)pyrimidine-5-carboxylate (100.0 mg, 0.216 mmol) in ethanol (5 mL) at room temperature was added hydrazine (70.7 mg, 2.162 mmol) slowly. The resulting mixture was stirred at 70° C. After 3 days, the reaction mixture was concentrated to afford the crude product which was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the product were combined and dried via centrifugal evaporation to afford 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (97 mg, 100% yield). HPLC $t_R$: 1.35 min; LC/MS Condition 3. ES [MS] m/z: 449.0 [M+H]$^+$. $^1$H NMR (500 MHz, DMSO-d$_6$) δ 10.05 (s, 1H), 9.66 (br d, J=8.1 Hz, 1H), 8.53 (s, 1H), 7.96 (s, 1H), 7.71-7.66 (m, 1H), 7.62 (d, J=8.4 Hz, 1H), 7.40-7.35 (m, 4H), 7.30-7.23 (m, 1H), 5.28 (br s, 1H), 3.88-3.81 (m, 1H), 3.77 (br d, J=5.9 Hz, 1H), 2.57-2.53 (m, 2H), 1.85 (s, 2H), 1.58 (s, 3H), 1.53 (s, 3H).

Example 52

5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-2,3-dihydro-1,3,4-oxadiazol-2-one (52)

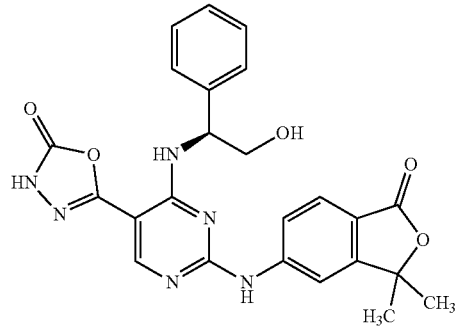

To a solution of 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (93.0 mg, 0.207 mmol) in THF (10 mL) at room temperature under nitrogen was added 1,1'-carbonyldiimidazole (50.4 mg, 0.311 mmol), followed by triethylamine (0.207 mL, 0.829 mmol). After 1 h, the reaction mixture was concentrated and redissolved in THF, followed by addition of 0.5 mL of a 1 N aqueous solution of NaOH. After stirring for an additional 0.5 h, the reaction mixture was diluted with EtOAc and washed with brine. The organic layer was dried over MgSO$_4$, filtered and concentrated to afford a crude residue which was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the product were combined and dried via centrifugal evaporation to afford 5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-2,3-dihydro-1,3,4-oxadiazol-2-one (6.0 mg, 6.15 yield). HPLC $t_R$: 1.43 min; LC/MS Condition 2. ES [MS] m/z: 475.1 [M+H]$^+$. $^1$H NMR (500 MHz, DMSO-d$_6$) δ 10.05 (s, 1H), 8.44 (s, 1H), 8.15 (d, J=8.1 Hz, 1H), 7.90 (s, 1H), 7.74 (d, J=8.4 Hz, 1H), 7.62 (d, J=8.4 Hz, 1H), 7.42-7.34 (m, 4H), 7.29-7.24 (m, 1H), 5.42 (d, J=7.7 Hz, 1H), 3.95-3.88 (m, 1H), 3.86-3.79 (m, 1H), 1.58 (s, 3H), 1.54 (s, 3H).

Example 53

5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-3-ethyl-2,3-dihydro-1,3,4-oxadiazol-2-one

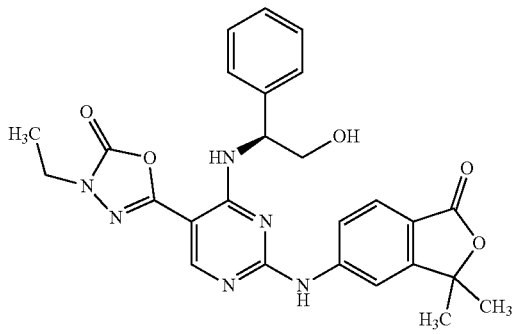

(53)

To a 20 mL vial was added 5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-2,3-dihydro-1,3,4-oxadiazol-2-one (25.0 mg, 0.053 mmol), iodoethane (9.86 mg, 0.063 mmol), and DMF (3 mL) followed by potassium carbonate (21.8 mg, 0.158 mmol). The resulting reaction mixture was stirred at room temperature. After 1 hour, LCMS indicated the formation of the product. The crude material was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the product were combined and dried via centrifugal evaporation to afford 5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-3-ethyl-2,3-dihydro-1,3,4-oxadiazol-2-one (5.5 mg, 20.8% yield). HPLC $t_R$: 1.56 min; LC/MS Condition 3. ES [MS] m/z: 503.1 [M+H]$^+$. $^1$H NMR (500 MHz, DMSO-d$_6$) δ 10.10 (s, 1H), 8.46 (s, 1H), 8.20 (d, J=7.3 Hz, 1H), 7.94 (s, 1H), 7.63 (d, J=8.4 Hz, 1H), 7.44-7.40 (m, 2H), 7.40-7.35 (m, 2H), 7.30-7.25 (m, 1H), 5.44-5.36 (m, 1H), 3.96-3.89 (m, 1H), 3.88-3.83 (m, 1H), 3.82-3.78 (m, 2H), 2.55 (s, 1H), 1.59 (s, 3H), 1.55 (s, 3H), 1.37 (t, J=7.2 Hz, 3H).

Example 54

5-[(4-{[(1S)-2-hydroxy-1-phenylethyl]amino}-5-(1,3,4-oxadiazol-2-yl)pyrimidin-2-yl) amino]-3,3-dimethyl-1,3-dihydro-2-benzofuran-1-one

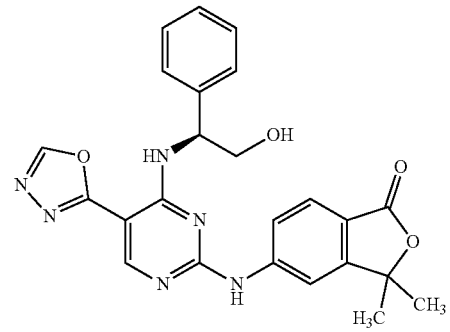

(54)

To a stirred solution of 2-[(3,3-dimethyl-1-oxo-1,3-dihydro-2-benzofuran-5-yl) amino]-4-{[(1S)-2-hydroxy-1-phenylethyl]amino}pyrimidine-5-carbohydrazide (25.0 mg, 0.056 mmol) in acetic acid (1 mL) at room temperature was added triethoxymethane (83 mg, 0.557 mmol). The resulting mixture was stirred at 100° C. overnight. The reaction mixture was cooled to room temperature, concentrated to dryness, dissolved in 15 mL of a 10% solution of EtOH in EtOAc and washed with brine. The organic layer was separated and concentrated to dryness, and then redissolved in 2 mL of methanol, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 22 minutes, then a 4-minute hold at 100% B; Flow: 20 mL/min. Fractions containing the product were combined and dried via centrifugal evaporation to afford 5-[(4-{[(1S)-2-hydroxy-1-phenylethyl]amino}-5-(1,3,4-oxadiazol-2-yl)pyrimidin-2-yl)amino]-3,3-dimethyl-1,3-dihydro-2-benzofuran-1-one (2 mg, 7.2% yield). HPLC $t_R$: 1.89 min; LC/MS Condition 2. ES [MS] m/z: 459.1 [M+H]$^+$. $^1$H NMR (500 MHz, DMSO-d$_6$) δ 10.32 (s, 1H), 9.36 (s, 1H), 8.93 (br d, J=7.34 Hz, 1H), 8.71 (s, 1H), 7.96 (s, 1H), 7.74 (br d, J=8.80 Hz, 1H), 7.65 (d, J=8.80 Hz, 1H), 7.36-7.44 (m, 4H), 7.26-7.30 (m, 1H), 5.42-5.47 (m, 1H), 5.29 (t, J=4.95 Hz, 1H), 3.93 (br dd, J=10.64, 5.87 Hz, 1H), 3.83-3.88 (m, 1H), 3.41 (br d, J=2.93 Hz, 1H), 1.59 (s, 3H), 1.54 (s, 3 H).

Example 55

5-[(4-{[(1S)-2-hydroxy-1-phenylethyl]amino}-5-(5-methyl-1,3,4-oxadiazol-2-yl)pyrimidin-2-yl)amino]-3,3-dimethyl-1,3-dihydro-2-benzofuran-1-one (55)

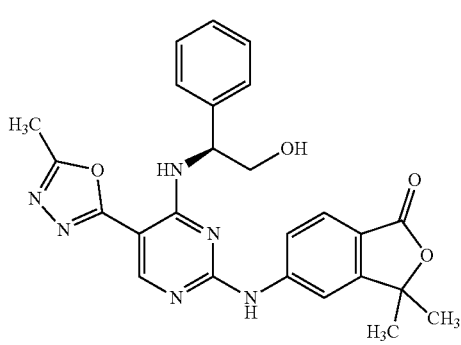

To a solution of 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (30.0 mg, 0.067 mmol) in EtOH (1 mL) at room temperature was added 1,1,1-trimethoxyethane (161 mg, 1.34 mmol), followed by NH$_4$Cl (0.716 mg, 0.013 mmol). The resulting mixture was stirred at 78° C. (refluxing). After 18 h, the reaction mixture was cooled to room temperature, concentrated to dryness, and was then redissolved in 2 mL of methanol, filtered and purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 12-52% B over 22 minutes, then a 4-minute hold at 100% B; Flow: 20 mL/min. Fractions containing the product were combined and dried via centrifugal evaporation to afford 5-[(4-{[(1S)-2-hydroxy-1-phenylethyl]amino}-5-(5-methyl-1,3,4-oxadiazol-2-yl)pyrimidin-2-yl)amino]-3,3-dimethyl-1,3-dihydro-2-benzofuran-1-one (5.7 mg, 19.9%). HPLC t$_R$: 1.64 min; LC/MS Condition 2. ES [MS]m/z: 473.2 [M+H]$^+$. $^1$H NMR (500 MHz, DMSO-d$_6$) δ 10.11 (s, 1H), 8.82 (d, J=8.1 Hz, 1H), 8.62 (s, 1H), 7.97 (s, 1H), 7.75 (dd, J=8.4, 1.5 Hz, 1H), 7.64 (d, J=8.4 Hz, 1H), 7.44-7.40 (m, 2H), 7.37 (t, J=7.2 Hz, 2H), 7.27 (t, J=7.2 Hz, 1H), 5.48-5.44 (m, 1H), 3.96-3.91 (m, 1H), 3.85 (dt, J=10.5, 5.0 Hz, 1H), 3.19 (s, 1H), 2.60 (s, 3H), 1.60 (s, 3H), 1.58-1.54 (m, 3H).

Example 56

N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide (56)

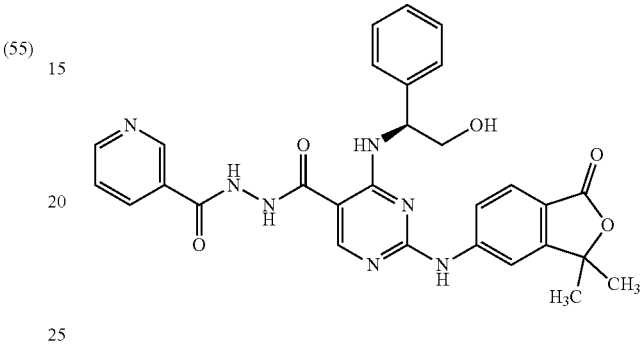

To a solution of 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (40.0 mg, 0.089 mmol) in DCM (10 mL) at room temperature was added nicotinic acid (16.5 mg, 0.134 mmol), followed by EDC (25.6 mg, 0.134 mmol). The resulting mixture was stirred at room temperature and then heated to 40° C. After 18 h, the reaction mixture was cooled to room temperature and concentrated to dryness, and the resulting residue was redissolved in a 10% solution of EtOH in EtOAc and washed with brine. The organic layer was separated, dried over Na$_2$SO$_4$, filtered and concentrated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 25 minutes, then a 4-minute hold at 100% B; Flow: 20 mL/min. Fractions containing the product were combined and dried via centrifugal evaporation to afford N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide (49 mg, 99% yield). HPLC t$_R$: 1.66 min; LC/MS Condition 2. ES [MS]m/z: 554.2 [M+H]$^+$. $^1$H NMR (500 MHz, DMSO-d$_6$) δ 9.70-9.55 (m, 1H), 9.10 (s, 1H), 8.81-8.78 (m, 1H), 8.77 (s, 1H), 8.29 (br d, J=8.1 Hz, 1H), 7.97 (s, 1H), 7.71 (br d, J=8.4 Hz, 1H), 7.64 (d, J=8.4 Hz, 1H), 7.60 (dd, J=7.9, 5.0 Hz, 1H), 7.39-7.34 (m, 4H), 7.26 (td, J=5.8, 3.1 Hz, 1H), 5.35-5.28 (m, 1H), 3.87-3.82 (m, 1H), 3.77 (dt, J=10.3, 5.1 Hz, 1H), 1.59 (s, 3H), 1.55 (s, 3H).

Example 57

5-[(4-{[(1S)-2-hydroxy-1-phenylethyl]amino}-5-[5-(pyridin-3-yl)-1,3,4-oxadiazol-2-yl]pyrimidin-2-yl)amino]-3,3-dimethyl-1,3-dihydro-2-benzofuran-1-one

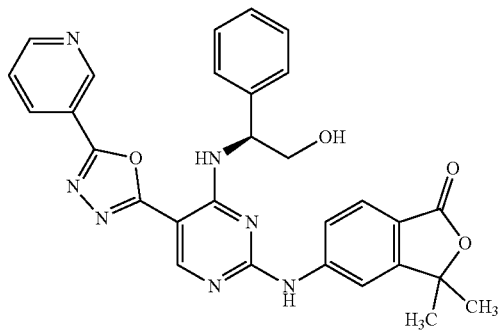

(57)

To a solution of N'-{2-[(3,3-dimethyl-1-oxo-1,3-dihydro-2-benzofuran-5-yl) amino]-4-{[(1S)-2-hydroxy-1-phenylethyl]amino}pyrimidine-5-carbonyl}pyridine-3-carbohydrazide (35.0 mg, 0.063 mmol) in THF (8 mL) at room temperature was added p-toluenesulfonyl chloride (24.1 mg, 0.126 mmol), followed by triethylamine (0.026 mL, 0.190 mmol). The resulting mixture was stirred at room temperature and then heated to 55° C. After 64 h, the reaction mixture was cooled to room temperature, concentrated to dryness, and dissolved in 15 mL of a 10% solution of EtOH in EtOAc. The solution was washed with brine, the organic layer was separated, concentrated, and then redissolved in 2 mL of methanol, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 23 minutes, then a 4-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 32-72% B over 20 minutes, then a 4-minute hold at 100% B; Flow: 20 mL/min. Fractions containing the product were combined and dried via centrifugal evaporation to afford 5-[(4-{[(1S)-2-hydroxy-1-phenylethyl]amino}-5-[5-(pyridin-3-yl)-1,3,4-oxadiazol-2-yl]pyrimidin-2-yl)amino]-3,3-dimethyl-1,3-dihydro-2-benzofuran-1-one (3.1 mg, 9.2% yield). HPLC $t_R$: 2.04 min; LC/MS Condition 2. ES [MS] m/z: 536.2 [M+H]$^+$. $^1$H NMR (500 MHz, DMSO-d$_6$) δ 10.16 (s, 1H), 9.33 (s, 1H), 8.92 (s, 1H), 8.88-8.80 (m, 2H), 8.52 (d, J=7.8 Hz, 1H), 7.97 (s, 1H), 7.77 (d, J=8.4 Hz, 1H), 7.70-7.63 (m, 2H), 7.47-7.42 (m, 2H), 7.38 (t, J=7.5 Hz, 2H), 7.30-7.25 (m, 1H), 5.51-5.45 (m, 1H), 3.99-3.93 (m, 1H), 3.88 (dt, J=10.7, 5.1 Hz, 1H), 3.43-3.22 (m, 1H), 1.60 (s, 3H), 1.57 (s, 3H).

Example 58

N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl} pyrazine-2-carbohydrazide

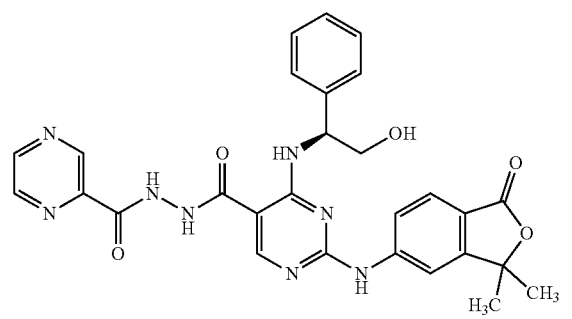

(58)

Example 58 was prepared according to the general preparation procedure for N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide using pyrazine-2-carboxylic acid. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min to afford N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyrazine-2-carbohydrazide (25 mg, 44.9% yield). HPLC $t_R$: 1.72 min; LC/MS Condition 2. ES [MS] m/z: 555.2 [M+H]$^+$. $^1$H NMR (500 MHz, DMSO-d$_6$) δ 9.98 (s, 1H), 9.50-9.40 (m, 1H), 9.23-9.21 (m, 1H), 8.92 (d, J=2.6 Hz, 1H), 8.79 (s, 1H), 8.75 (s, 1H), 7.95 (s, 1H), 7.74 (d, J=8.4 Hz, 1H), 7.63 (d, J=8.4 Hz, 1H), 7.38-7.33 (m, 4H), 7.25 (br t, J=6.6 Hz, 1H), 5.35-5.30 (m, 1H), 3.87-3.82 (m, 1H), 3.77 (dt, J=10.6, 5.3 Hz, 1H), 2.56-2.53 (m, 1H), 1.59 (s, 3H), 1.56 (s, 3H).

Example 59

1-({2-[(3,3-dimethyl-1-oxo-1,3-dihydro-2-benzofuran-5-yl)amino]-4-{[(1S)-2-hydroxy-1-phenylethyl]amino}pyrimidin-5-yl}formohydrazido)-N-[3-(dimethylamino)propyl]-N'-ethylmethanimidamide

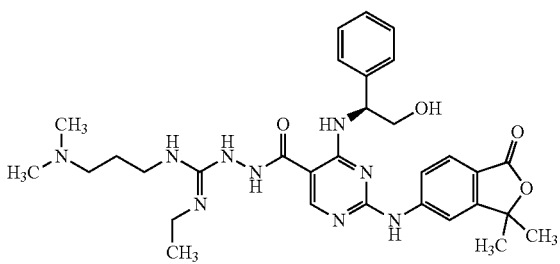

(59)

To a 20 mL scintillation vial were added (2-[(3,3-dimethyl-1-oxo-1,3-dihydro-2-benzofuran-5-yl)amino]-4-{1[(1S)-2-hydroxy-1-phenylethyl]amino}pyrimidine-5-carbohydrazide (40.0 mg, 0.089 mmol), sodium pyrimidine-2-carboxylate (15.6 mg, 0.107 mmol), N1-((ethylimino)methylene)-N3,N3-dimethylpropane-1,3-diamine, HCl (25.6 mg, 0.134 mmol) and DCM (10 mL). The reaction mixture was stirred and heated to 40° C. After 3 h, the mixture was concentrated to dryness, diluted with EtOAc and washed with brine. The layers were separated and the organic layer was dried over MgSO$_4$, filtered and concentrated. The crude residue was dissolved in 2 mL of methanol, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-40% B over 25 minutes, then a 5-minute hold at 100% B; Flow: 20 mL/min. Fractions containing the product were combined and dried via centrifugal evaporation to afford 1-({2-[(3,3-dimethyl-1-oxo-1,3-dihydro-2-benzofuran-5-yl)amino]-4-{[(1S)-2-hydroxy-1-phenylethyl]amino}pyrimidin-5-yl}formohydrazido)-N-[3-(dimethylamino)propyl]-N'-ethylmethanimidamide (19.8 mg, 36.8%). HPLC t$_R$: 1.22 min; LC/MS Condition 2. ES [MS] m/z: 604.2 [M+H]$^+$. $^1$H NMR (500 MHz, DMSO-d$_6$) δ 10.07 (s, 1H), 9.33 (br d, J=7.7 Hz, 1H), 8.76 (s, 1H), 8.07-7.98 (m, 1H), 7.90 (s, 1H), 7.74 (d, J=8.2 Hz, 1H), 7.62 (d, J=8.4 Hz, 1H), 7.39-7.34 (m, 4H), 7.30-7.21 (m, 1H), 5.35-5.30 (m, 1H), 3.89-3.84 (m, 1H), 3.82-3.75 (m, 1H), 3.12-3.05 (m, 1H), 2.84-2.76 (m, 6H), 2.55-2.52 (m, 2H), 1.99-1.88 (m, 2H), 1.61-1.50 (m, 6H), 1.19 (br s, 3H).

Example 60

2-[(3,3-dimethyl-1-oxo-1,3-dihydro-2-benzofuran-5-yl)amino]-4-{[(1S)-2-hydroxy-1-phenylethyl]amino}-N'-(2-hydroxy-2-methylpropanoyl)pyrimidine-5-carbohydrazide (60)

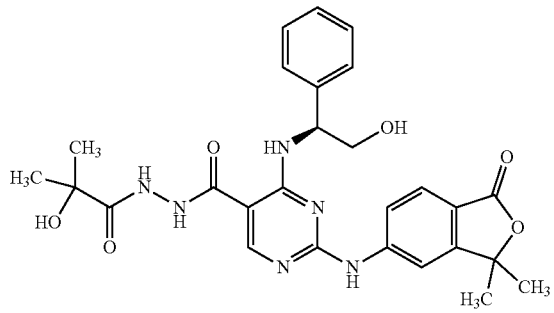

To a stirred solution of 2-hydroxy-2-methylpropanoic acid (9.98 mg, 0.096 mmol) in DCM (6 mL) and DMA (2 mL) at room temperature were added DCC (19.7 mg, 0.096 mmol) and HOBt (0.020 mL, 0.096 mmol). After stirring for 1 hour, 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (43 mg, 0.096 mmol) was added. The resulting mixture was stirred at room temperature overnight. The reaction mixture was then concentrated to dryness, and redissolved in a 10% solution of EtOH in EtOAc and washed with brine. The organic layer was separated, dried over Na$_2$SO$_4$, and concentrated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 25 minutes, then a 5-minute hold at 100% B; Flow: 20 mL/min. Fractions containing the product were combined and dried via centrifugal evaporation to afford 2-[(3,3-dimethyl-1-oxo-1,3-dihydro-2-benzofuran-5-yl)amino]-4-{[(1S)-2-hydroxy-1-phenylethyl]amino}-N'-(2-hydroxy-2-methylpropanoyl)pyrimidine-5-carbohydrazide (32 mg, 50% yield). HPLC t$_R$: 1.26 min; LC/MC Condition 3. ES [MS] m/z: 535.1 [M+H]$^+$. $^1$H NMR (500 MHz, DMSO-d$_6$) δ 9.94 (br d, J=1.1 Hz, 1H), 9.42 (br s, 1H), 8.68 (s, 1H), 7.92 (br s, 1H), 7.73 (br d, J=8.4 Hz, 1H), 7.62 (d, J=8.4 Hz, 1H), 7.40-7.33 (m, 4H), 7.25 (br t, J=6.2 Hz, 1H), 7.22-7.06 (m, 2H), 5.35-5.29 (m, 1H), 3.88-3.82 (m, 1H), 3.77 (br dd, J=10.6, 5.9 Hz, 1H), 1.58 (s, 3H), 1.55 (s, 3H), 1.36 (s, 6H).

Example 61

5-[(4-{[(1S)-2-hydroxy-1-phenylethyl]amino}-5-[5-(2-hydroxypropan-2-yl)-1,3,4-oxadiazol-2-yl]pyrimidin-2-yl)amino]-3,3-dimethyl-1,3-dihydro-2-benzofuran-1-one (61)

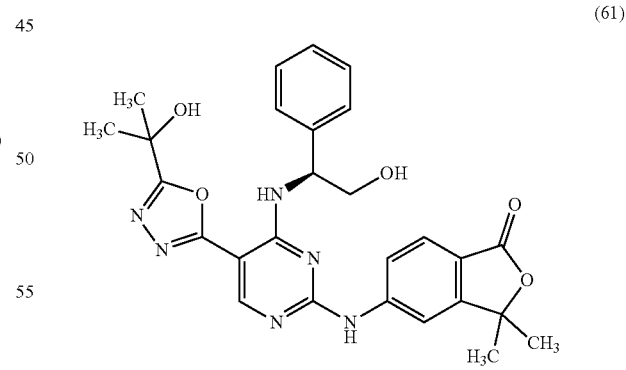

To a solution of 2-[(3,3-dimethyl-1-oxo-1,3-dihydro-2-benzofuran-5-yl)amino]-4-{[(1S)-2-hydroxy-1-phenylethyl]amino}-N'-(2-hydroxy-2-methylpropanoyl) pyrimidine-5-carbohydrazide (15.0 mg, 0.028 mmol) in DCM (8 mL) at room temperature was added p-toluenesulfonyl chloride (10.7 mg, 0.056 mmol), followed by triethylamine (0.012 mL, 0.084 mmol). The resulting mixture was stirred at room temperature. After 18 h, the reaction mixture was concentrated to dryness, redissolved in 2 mL of methanol, and filtered prior to purification via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the product were combined and dried via centrifugal evaporation to afford 5-[(4-{[(1S)-2-hydroxy-1-phenylethyl]amino}-5-[5-(2-hydroxypropan-2-yl)-1,3,4-oxadiazol-2-yl]pyrimidin-2-yl) amino]-3,3-dimethyl-1,3-dihydro-2-benzofuran-1-one (4.5 mg, 29.8% yield). HPLC $t_R$: 1.43 min; LC/MS Condition 3. ES [MS] m/z: 517.1 [M+H]$^+$. $^1$H NMR (500 MHz, DMSO-$d_6$) δ 10.18-10.13 (m, 1H), 8.84 (br d, J=7.7 Hz, 1H), 8.68 (s, 1H), 8.00 (s, 1H), 7.75 (d, J=8.8 Hz, 1H), 7.65 (d, J=8.1 Hz, 1H), 7.45-7.40 (m, 2H), 7.38 (t, J=7.5 Hz, 2H), 7.28 (t, J=7.0 Hz, 1H), 5.83 (s, 1H), 5.49-5.43 (m, 1H), 3.96-3.90 (m, 1H), 3.85 (dt, J=10.5, 5.2 Hz, 1H), 1.65 (s, 6H), 1.60 (s, 3H), 1.56 (s, 3H), 1.26 (t, J=7.3 Hz, 1H).

Example 62

(S)—N'-(cyclopropanecarbonyl)-2-((3,3-dimethyl-1-oxo-1,3-dihydroisobenzofuran-5-yl) amino)-4-((2-hydroxy-1-phenylethyl)amino)pyrimidine-5-carbohydrazide (62)

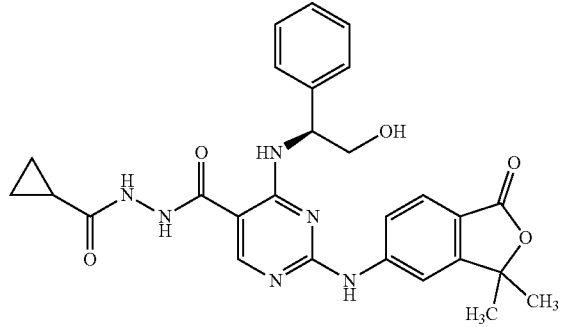

To a solution of 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (50.0 mg, 0.111 mmol) in DCM (10 mL) at room temperature was added cyclopropanecarboxylic acid (14.4 mg, 0.167 mmol), followed by EDC (32.1 mg, 0.167 mmol). The resulting mixture was stirred at room temperature and then heated to 40° C. After 1 h, the reaction mixture was diluted with DCM and washed with water. The organic layer was separated, dried over MgSO$_4$, filtered and concentrated to afford a crude residue which was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the product were combined and dried via centrifugal evaporation to afford (S)—N'-(cyclopropanecarbonyl)-2-((3,3-dimethyl-1-oxo-1,3-dihydroisobenzofuran-5-yl) amino)-4-((2-hydroxy-1-phenylethyl)amino)pyrimidine-5-carbohydrazide (11.5 mg, 20% yield). HPLC $t_R$: 1.47 min; LC/MS Condition 3. ES [MS] m/z: 517.0 [M+H]$^+$. $^1$H NMR (500 MHz, DMSO-$d_6$) δ 10.16 (br s, 1H), 8.67 (s, 1H), 7.96 (s, 1H), 7.69 (br d, J=8.8 Hz, 1H), 7.63 (d, J=8.4 Hz, 1H), 7.37 (d, J=4.4 Hz, 4H), 7.29-7.23 (m, 1H), 5.31 (br s, 1H), 5.18 (s, 1H), 3.92 (s, 1H), 2.56-2.54 (m, 1H), 1.70 (br s, 1H), 1.59 (s, 3H), 1.54 (s, 3H), 0.85-0.74 (m, 4H).

Example 63

5-{[5-(5-cyclopropyl-1,3,4-oxadiazol-2-yl)-4-{[(1S)-2-hydroxy-1-phenylethyl]amino}pyrimidin-2-yl] amino}-3,3-dimethyl-1,3-dihydro-2-benzofuran-1-one (63)

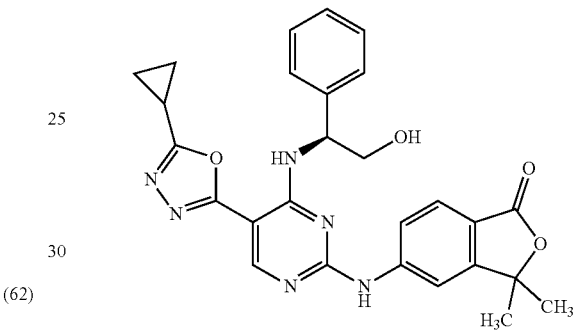

To a solution of (S)—N'-(cyclopropanecarbonyl)-2-((3,3-dimethyl-1-oxo-1,3-dihydroisobenzofuran-5-yl)amino)-4-((2-hydroxy-1-phenylethyl)amino)pyrimidine-5-carbohydrazide (30.0 mg, 0.058 mmol) in THF (2 mL) at room temperature was added p-toluenesulfonyl chloride (22.1 mg, 0.116 mmol), followed by triethylamine (17.6 mg, 0.174 mmol). The resulting mixture was stirred at room temperature and then heated to 55° C. After 18 h, the reaction mixture was cooled to room temperature and concentrated to dryness, dissolved in 15 mL of a 10% solution of EtOH in EtOAc solution and washed with brine. The organic layer was separated and concentrated to dryness, then redissolved in 2 mL of 1,4-dioxane and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 23 minutes, then a 5-minute hold at 100% B; Flow: 20 mL/min. Fractions containing the product were combined and dried via centrifugal evaporation to afford 5-{[5-(5-cyclopropyl-1,3,4-oxadiazol-2-yl)-4-{[(1S)-2-hydroxy-1-phenylethyl]amino}pyrimidin-2-yl] amino}-3,3-dimethyl-1,3-dihydro-2-benzofuran-1-one (6.5 mg, 22.2% yield). HPLC $t_R$: 2.07 min; LC/MS Condition 2. ES [MS] m/z [M+H]$^+$: 499.0. $^1$H NMR (500 MHz, DMSO-$d_6$) δ 10.30 (s, 1H), 8.85 (br d, J=7.7 Hz, 1H), 8.65 (s, 1H), 7.99 (s, 1H), 7.71 (br d, J=8.1 Hz, 1H), 7.64 (d, J=8.4 Hz, 1H), 7.43-7.35 (m, 4H), 7.27 (t, J=7.0 Hz, 1H), 5.43 (br d, J=7.3 Hz, 1H), 5.26 (t, J=5.0 Hz, 1H), 3.94-3.81 (m, 2H), 3.37 (s, 1H), 2.56-2.53 (m, 1H), 2.38-2.30 (m, 1H), 1.59 (s, 3H), 1.54 (s, 3H), 1.23-1.14 (m, 4H).

Example 64

2-[(3,3-dimethyl-1-oxo-1,3-dihydro-2-benzofuran-5-yl)amino]-4-{[(1S)-2-hydroxy-1-phenylethyl]amino}-N'-(3,3,3-trifluoro-2-hydroxy-2-methylpropanoyl)pyrimidine-5-carbohydrazide

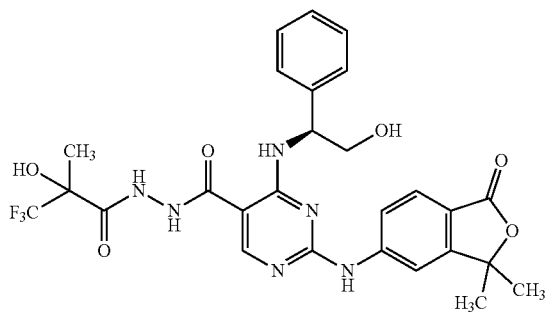

(64)

To a stirred solution of 2-[(3,3-dimethyl-1-oxo-1,3-dihydro-2-benzofuran-5-yl) amino]-4-{[(1S)-2-hydroxy-1-phenylethyl]amino}pyrimidine-5-carbohydrazide (60.0 mg, 0.134 mmol) in DCM (10 mL) at room temperature was added 3,3,3-trifluoro-2-hydroxy-2-methylpropanoic acid (31.7 mg, 0.201 mmol), followed by EDC (38.5 mg, 0.201 mmol). The resulting mixture was stirred at room temperature and then heated to 40° C. After 6 h, the reaction mixture was cooled to room temperature, concentrated to dryness, and redissolved in a 10% solution of EtOH in EtOAc and was washed with brine. The organic layer was separated, dried over $Na_2SO_4$, and concentrated to afford a crude residue which was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 23 minutes, then a 4-minute hold at 100% B; Flow: 20 mL/min. Fractions containing the product were combined and dried via centrifugal evaporation to afford 2-[(3,3-dimethyl-1-oxo-1,3-dihydro-2-benzofuran-5-yl)amino]-4-{[(1S)-2-hydroxy-1-phenylethyl]amino}-N'-(3,3,3-trifluoro-2-hydroxy-2-methylpropanoyl)pyrimidine-5-carbohydrazide (62 mg, 79% yield). HPLC $t_R$: 1.84 min; LC/MS Condition 2. ES [MS] m/z: 589.2 [M+H]+. 1H NMR (500 MHz, DMSO-$d_6$) δ 8.63 (s, 1H), 8.00 (s, 1H), 7.67 (d, J=8.29 Hz, 1H), 7.61 (d, J=8.21 Hz, 1H), 7.40-7.44 (m, 2H), 7.36 (t, J=7.70 Hz, 2H), 7.23-7.28 (m, 1H), 5.25-5.32 (m, 1H), 3.83 (br dd, J=10.82, 4.22 Hz, 1H), 3.77 (br dd, J=10.64, 5.87 Hz, 1H), 1.59 (s, 3H), 1.55 (br d, J=10.27 Hz, 6H).

Example 65

5-[(4-{[(1S)-2-hydroxy-1-phenylethyl]amino}-5-[5-(1,1,1-trifluoro-2-hydroxypropan-2-yl)-1,3,4-oxadiazol-2-yl]pyrimidin-2-yl)amino]-3,3-dimethyl-1,3-dihydro-2-benzofuran-1-one

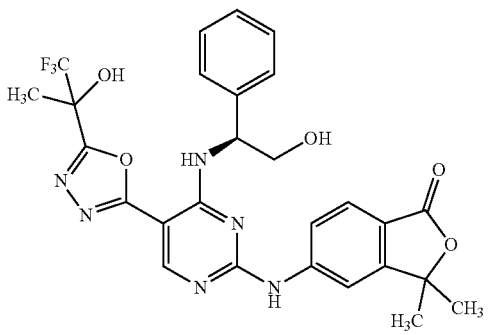

(65)

To a solution of 2-[(3,3-dimethyl-1-oxo-1,3-dihydro-2-benzofuran-5-yl)amino]-4-{[(1S)-2-hydroxy-1-phenylethyl]amino}-N'-(3,3,3-trifluoro-2-hydroxy-2-methylpropanoyl)pyrimidine-5-carbohydrazide (50.0 mg, 0.085 mmol) in THF (8 mL) at room temperature was added p-toluenesulfonyl chloride (32.4 mg, 0.170 mmol), followed by triethylamine (0.035 mL, 0.255 mmol). The resulting mixture was stirred at room temperature and then heated to 55° C. After 5 days, LCMS analysis indicated complete conversion to two isomeric products. The reaction mixture was concentrated to dryness, then dissolved in 15 mL of a 10% solution of EtOH in EtOAc which was washed with brine (3×20 mL). The organic layer was separated and concentrated to dryness, and then redissolved in 2 mL of methanol, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the product were combined and dried via centrifugal evaporation to afford 5-[(4-{[(1S)-2-hydroxy-1-phenylethyl]amino}-5-[5-(1,1,1-trifluoro-2-hydroxypropan-2-yl)-1,3,4-oxadiazol-2-yl]pyrimidin-2-yl)amino]-3,3-dimethyl-1,3-dihydro-2-benzofuran-1-one (6.3 mg, 12.5% yield). HPLC $t_R$: 1.96 min; LC/MS Condition 3. ES [MS] m/z: 571.2 [M+H]+. 1H NMR (500 MHz, DMSO-$d_6$): δ 8.83 (br d, J=7.7 Hz, 1H), 8.69 (s, 1H), 8.00 (s, 1H), 7.71 (d, J=8.4 Hz, 1H), 7.66 (d, J=8.4 Hz, 1H), 7.41-7.46 (m, 2H), 7.39 (t, J=7.1 Hz, 2H), 7.28 (t, J=7.2 Hz, 1H), 5.42-5.48 (m, 1H), 3.90-3.97 (m, 1H), 3.85 (dd, J=10.6, 5.1 Hz, 1H), 1.87 (s, 3H), 1.59 (s, 3H), 1.54 (s, 3H).

Example 66

5-[(4-{[(1S)-2-hydroxy-1-phenylethyl]amino}-5-[5-(pyridin-2-yl)-1,3,4-oxadiazol-2-yl]pyrimidin-2-yl)amino]-3,3-dimethyl-1,3-dihydro-2-benzofuran-1-one

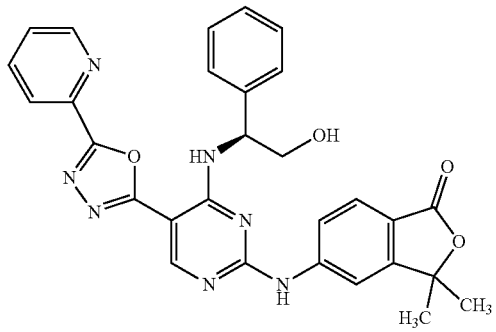

(66)

(S)-2-((3,3-dimethyl-1-oxo-1,3-dihydroisobenzofuran-5-yl)amino)-4-((2-hydroxy-1-phenylethyl)amino)-N'-picolinoylpyrimidine-5-carbohydrazide was prepared according to the general procedure for N'-{2-[(3,3-dimethyl-1-oxo-1,3-dihydro-2-benzofuran-5-yl) amino]-4-{[(1S)-2-hydroxy-1-phenylethyl]amino}pyrimidine-5-carbonyl}pyridine-3-carbohydrazide using picolinic acid.

To a solution of (S)-2-((3,3-dimethyl-1-oxo-1,3-dihydroisobenzofuran-5-yl) amino)-4-((2-hydroxy-1-phenylethyl)amino)-N'-picolinoylpyrimidine-5-carbohydrazide (33.0 mg, 0.060 mmol) in THF (8 mL) at room temperature was added p-toluenesulfonyl chloride (22.7 mg, 0.119 mmol), and followed by triethylamine (0.025 mL, 0.179 mmol). The resulting mixture was stirred at room temperature and then heated to 55° C. The reaction mixture was cooled to room temperature, concentrated to dryness, and dissolved in 15 mL of a 10% solution of EtOH in EtOAc. The solution was washed with brine, the organic layer was separated, concentrated, and then redissolved in 2 mL of methanol, filtered and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 27 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the product were combined and dried via centrifugal evaporation to afford 5-[(4-{[(1S)-2-hydroxy-1-phenylethyl]amino}-5-[5-(pyridin-2-yl)-1,3,4-oxadiazol-2-yl]pyrimidin-2-yl)amino]-3,3-dimethyl-1,3-dihydro-2-benzofuran-1-one (3.2 mg, 9.6% yield). HPLC $t_R$: 1.77 min; LC/MS Condition 3. ES [MS] m/z: 536.2 [M+H]$^+$. $^1$H NMR (500 MHz, DMSO-$d_6$) δ 10.20 (s, 1H), 8.90 (br d, J=7.7 Hz, 1H), 8.84-8.81 (m, 1H), 8.81 (s, 1H), 8.29 (d, J=8.1 Hz, 1H), 8.09 (t, J=7.9 Hz, 1H), 7.99 (s, 1H), 7.76 (d, J=8.4 Hz, 1H), 7.68-7.63 (m, 2H), 7.46 (d, J=7.2 Hz, 2H), 7.39 (t, J=7.5 Hz, 2H), 7.31-7.26 (m, 1H), 5.52-5.46 (m, 1H), 4.00-3.94 (m, 1H), 3.89 (dt, J=10.5, 5.2 Hz, 1H), 3.30-3.28 (m, 1H), 1.61 (s, 3H), 1.57 (s, 3H).

Example 67

5-[(4-{[(1S)-2-hydroxy-1-phenylethyl]amino}-5-[5-(pyridazin-3-yl)-1,3,4-oxadiazol-2-yl]pyrimidin-2-yl)amino]-3,3-dimethyl-1,3-dihydro-2-benzofuran-1-one

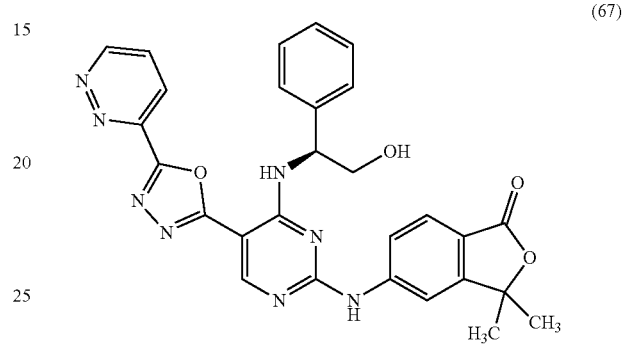

(67)

(S)—N'-(2-((3,3-dimethyl-1-oxo-1,3-dihydroisobenzofuran-5-yl) amino)-4-((2-hydroxy-1-phenylethyl)amino)pyrimidine-5-carbonyl)pyridazine-3-carbohydrazide was prepared according to the general procedure for N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide using pyridazine-3-carboxylic acid.

To a solution of (S)—N'-(2-((3,3-dimethyl-1-oxo-1,3-dihydroisobenzofuran-5-yl) amino)-4-((2-hydroxy-1-phenylethyl)amino)pyrimidine-5-carbonyl)pyridazine-3-carbohydrazide (30.0 mg, 0.054 mmol) in THF (8 mL) at room temperature was added p-toluenesulfonyl chloride (20.6 mg, 0.108 mmol), followed by triethylamine (0.023 mL, 0.162 mmol). The resulting mixture was stirred at room temperature and then heated to 55° C. After 18 h, the reaction mixture was concentrated to dryness, dissolved in 15 mL of a 10% solution of EtOH in EtOAc and washed with brine. The organic layer was separated, dried over MgSO$_4$, concentrated to dryness, and then redissolved in 2 mL of DMSO and filtered prior to purification via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 25 minutes, then a 5-minute hold at 100% B; Flow: 20 mL/min. Fractions containing the product were combined and dried via centrifugal evaporation to afford 5-[(4-{[(1S)-2-hydroxy-1-phenylethyl]amino}-5-[5-(pyridazin-3-yl)-1,3,4-oxadiazol-2-yl]pyrimidin-2-yl)amino]-3,3-dimethyl-1,3-dihydro-2-benzofuran-1-one (1.7 mg, 5% yield). HPLC $t_R$: 1.43 min; LC/MS Condition 3. ES [MS] m/z: 537.1 [M+H]$^+$.

Example 68

5-[(4-{[(1S)-2-hydroxy-1-phenylethyl]amino}-5-{5-[1-(trifluoromethyl)cyclopropyl]-1,3,4-oxadiazol-2-yl}pyrimidin-2-yl)amino]-3,3-dimethyl-1,3-dihydro-2-benzofuran-1-one

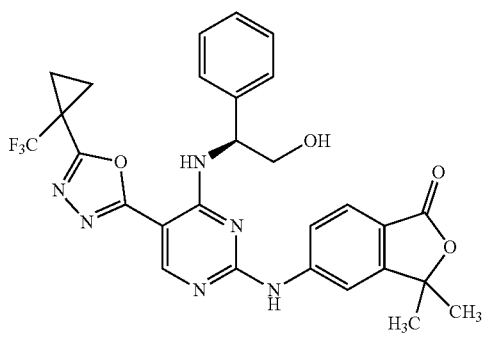

(68)

(S)-2-((3,3-dimethyl-1-oxo-1,3-dihydroisobenzofuran-5-yl)amino)-4-((2-hydroxy-1-phenylethyl)amino)-N'-(1-(trifluoromethyl)cyclopropanecarbonyl) pyrimidine-5-carbohydrazide was prepared according to the general procedure for N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide using 1-(trifluoromethyl)cyclopropanecarboxylic acid.

To a solution of (S)-2-((3,3-dimethyl-1-oxo-1,3-dihydroisobenzofuran-5-yl) amino)-4-((2-hydroxy-1-phenylethyl)amino)-N'-(1-(trifluoromethyl) cyclopropanecarbonyl)pyrimidine-5-carbohydrazide (25.0 mg, 0.043 mmol) in THF (2 mL) at room temperature was added p-toluenesulfonyl chloride (16.3 mg, 0.086 mmol), followed by triethylamine (13.0 mg, 0.128 mmol). The resulting mixture was stirred at room temperature and then heated to 55° C. over 4 days. The reaction mixture was concentrated to dryness, dissolved in 15 mL of a 10% EtOH in EtOAc solution and washed with brine. The organic layer was separated and concentrated to dryness, and then redissolved in 2 mL of methanol, filtered, and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 36-76% B over 25 minutes, then a 5-minute hold at 100% B; Flow: 20 mL/min. Fractions containing the product were combined and dried via centrifugal evaporation to afford 5-[(4-{[(1S)-2-hydroxy-1-phenylethyl]amino}-5-{5-[1-(trifluoromethyl)cyclopropyl]-1,3,4-oxadiazol-2-yl}pyrimidin-2-yl)amino]-3,3-dimethyl-1,3-dihydro-2-benzofuran-1-one (10.3 mg, 43.7% yield). HPLC $t_R$: 2.14 min; LC/MS Condition 3. ES [MS] m/z: 567.0 [M+H]$^+$. $^1$H NMR (500 MHz, DMSO-d$_6$) δ ppm 10.37 (br s, 1H), 8.83 (br d, J=7.70 Hz, 1H), 8.69 (s, 1H), 7.99 (s, 1H), 7.72 (d, J=8.27 Hz, 1H), 7.66 (d, J=8.14 Hz, 1H), 7.36-7.45 (m, 4H), 7.24-7.32 (m, 1H), 5.41-5.47 (m, 1H), 5.28 (t, J=4.77 Hz, 1H), 3.82-3.95 (m, 2H), 2.56 (s, 2H), 1.69-1.81 (m, 4H), 1.51-1.62 (m, 6H).

Example 69

(S)-5-((5-(5-(1,1-dioxidotetrahydro-2H-thiopyran-4-yl)-1,3,4-oxadiazol-2-yl)-4-((2-hydroxy-1-phenylethyl)amino)pyrimidin-2-yl)amino)-3,3-dimethylisobenzofuran-1(3H)-one

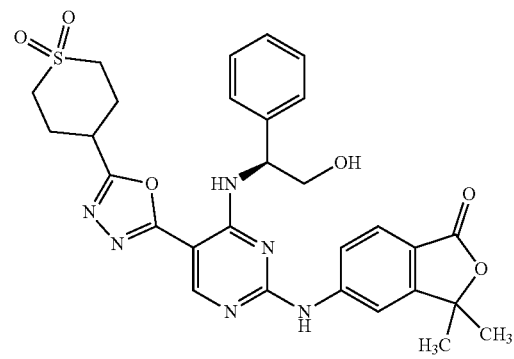

(69)

To a solution of 2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (30.0 mg, 0.067 mmol) in DCM (6 mL) at room temperature was added tetrahydro-2H-thiopyran-4-carboxylic acid 1,1-dioxide (17.9 mg, 0.100 mmol), followed by EDC (19.2 mg, 0.100 mmol). The resulting mixture was stirred at room temperature and then heated to 55° C. After 1 h, LCMS showed formation of the intermediate (S)-2-((3,3-dimethyl-1-oxo-1,3-dihydroisobenzofuran-5-yl)amino)-N-(1,1-dioxidotetrahydro-2H-thiopyran-4-carbonyl)-4-((2-hydroxy-1-phenylethyl)amino)pyrimidine-5-carbohydrazide. The reaction mixture was cooled to room temperature prior to the addition of p-toluenesulfonyl chloride (25.5 mg, 0.134 mmol) and triethylamine (0.047 mL, 0.334 mmol). The resulting mixture was stirred at room temperature overnight. The reaction mixture was then concentrated, redissolved in 2 mL of methanol, filtered, and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the product were combined and dried via centrifugal evaporation to afford (S)-5-((5-(5-(1,1-dioxidotetrahydro-2H-thiopyran-4-yl)-1,3,4-oxadiazol-2-yl)-4-((2-hydroxy-1-phenylethyl)amino)pyrimidin-2-yl)amino)-3,3-dimethylisobenzofuran-1(3H)-one (18 mg, 44.2% yield). HPLC $t_R$: 1.46 min; LC/MS Condition 3. ES [MS] m/z: 591.2 [M+H]$^+$. $^1$H NMR (500 MHz, DMSO-d$_6$) δ 10.19-9.97 (m, 1H), 8.88-8.72 (m, 1H), 8.69-8.56 (m, 1H), 7.89 (br d, J=9.9 Hz, 1H), 7.77-7.70 (m, 1H), 7.66-7.58 (m, 1H), 7.46-7.33 (m, 4H), 7.30-7.21 (m, 1H), 5.38 (s, 1H), 3.95-3.88 (m, 1H), 3.88-3.79 (m, 1H), 3.57-3.46 (m, 1H), 3.39-3.25 (m, 1H), 2.54 (s, 3H), 2.39-2.27 (m, 2H), 1.62-1.57 (m, 3H), 1.56-1.53 (m, 3H).

Example 70

1-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,3,4-oxadiazol-2-yl)cyclopropyl 3,3-difluoroazetidine-1-carboxylate

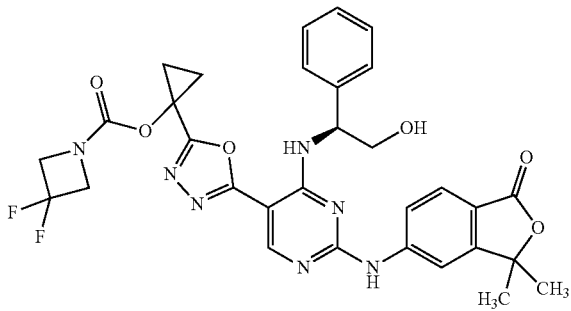

(70)

(S)-1-(2-(2-((3,3-dimethyl-1-oxo-1,3-dihydroisobenzofuran-5-yl) amino)-4-((2-hydroxy-1-phenylethyl)amino)pyrimidine-5-carbonyl)hydrazinecarbonyl)cyclopropyl 3,3-difluoro azetidine-1-carboxylate was prepared in an analogous manner to N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide using 1-((3,3-difluoroazetidine-1-carbonyl)oxy)cyclopropanecarboxylic acid To a stirred solution of (S)-1-(2-(2-((3,3-dimethyl-1-oxo-1,3-dihydroisobenzofuran-5-yl)amino)-4-((2-hydroxy-1-phenylethyl)amino)pyrimidine-5-carbonyl)hydrazinecarbonyl)cyclopropyl 3,3-difluoroazetidine-1-carboxylate (30.0 mg, 0.046 mmol) in THF (8 mL) at room temperature was added p-toluenesulfonyl chloride (17.6 mg, 0.092 mmol), followed by triethylamine (14.0 mg, 0.138 mmol). The resulting mixture was stirred at room temperature and then heated to 55° C. After two days, the reaction mixture was cooled to room temperature and concentrated to dryness. The residue was then dissolved in 15 mL of a 10% solution of EtOH in EtOAc and washed with brine. The organic layer was separated and concentrated to dryness, and then redissolved in 2 mL of methanol, filtered and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 4-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 38-78% B over 20 minutes, then a 5-minute hold at 100% B; Flow: 20 mL/min. Fractions containing the product were combined and dried via centrifugal evaporation to afford 1-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,3,4-oxadiazol-2-yl)cyclopropyl 3,3-difluoroazetidine-1-carboxylate (7.9 mg, 27% yield). HPLC $t_R$: 2.16 min; LC/MS Condition 3. ES [MS] m/z: 634.2 [M+H]$^+$. $^1$H NMR (DMSO-d$_6$, 500 MHz): δ 10.35 (br s, 1H), 8.83 (br d, J=7.7 Hz, 1H), 8.68 (s, 1H), 8.00 (s, 1H), 7.69-7.74 (m, 1H), 7.65 (d, J=8.3 Hz, 1H), 7.34-7.44 (m, 4H), 7.28 (br t, J=7.2 Hz, 1H), 5.40-5.47 (m, 1H), 4.35-4.59 (m, 4H), 3.89-3.95 (m, 1H), 3.84 (dd, J=11.0, 5.5 Hz, 1H), 1.65-1.72 (m, 2H), 1.60-1.65 (m, 2H), 1.59 (s, 3H), 1.54 (s, 3H).

Example 71

Ethyl 2-[(3,3-dimethyl-1-oxo-1,3-dihydro-2-benzofuran-5-yl)amino]-4-({[2-(2-hydroxypropan-2-yl)phenyl]methyl}amino)pyrimidine-5-carboxylate

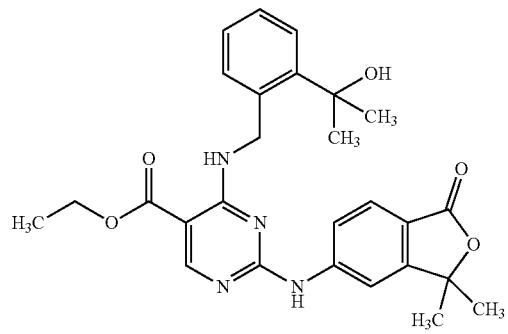

(71)

Preparation 71A: ethyl 2-chloro-4-((2-(prop-1-en-2-yl)benzyl)amino)pyrimidine-5-carboxylate

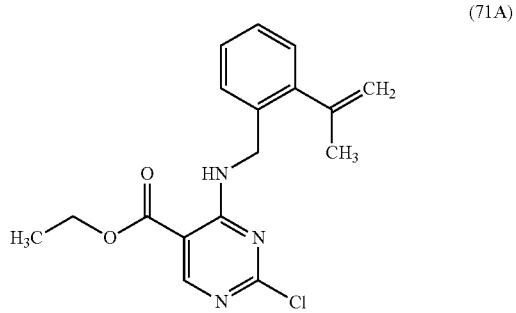 [SMILES: C=C(C)c1ccccc1CNc1nc(Cl)ncc1C(=O)OCC]

(71A)

To a 200 mL round bottom flask equipped with a stir bar and charged with a solution of ethyl 2,4-dichloropyrimidine-5-carboxylate (760 mg, 3.44 mmol) in acetonitrile (15 mL) was added DIPEA (1.19 mL, 6.88 mmol) followed by (2-(prop-1-en-2-yl)phenyl)methanamine hydrochloride (632 mg, 3.44 mmol). The resulting mixture was stirred at room temperature for 3 h. The reaction mixture was concentrated under reduced pressure and purified via silica gel chromatography eluting with a gradient from 0 to 20% EtOAc in hexanes to afford ethyl 2-chloro-4-((2-(prop-1-en-2-yl)benzyl) amino)pyrimidine-5-carboxylate (0.75 g, 2.26 mmol, 66% yield) as a light brown solid. ES [MS] m/z: 332.2 [M+H]$^+$. $^1$H NMR (500 MHz, CDCl$_3$) δ 8.69 (s, 1H), 8.62 (br. s., 1H), 7.44-7.38 (m, 1H), 7.34-7.24 (m, 2H), 7.23-7.17 (m, 1H), 5.29 (s, 1H), 4.95 (s, 1H), 4.77 (d, J=5.7 Hz, 2H), 4.35 (q, J=7.1 Hz, 2H), 2.11 (s, 3H), 1.39 (t, J=7.2 Hz, 3H).

Preparation 71B: Ethyl 2-chloro-4-((2-(prop-1-en-2-yl)benzyl)amino)pyrimidine-5-carboxylate

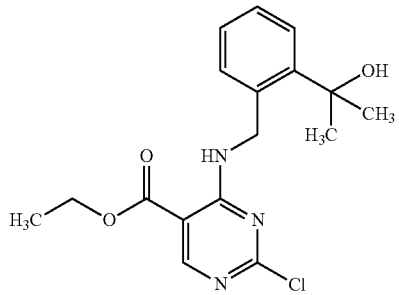

(71B)

A flask charged with a solution of ethyl 2-chloro-4-((2-(prop-1-en-2-yl)benzyl) amino)pyrimidine-5-carboxylate (750 mg, 2.260 mmol) in 2-propanol (36 mL) and DCM (7.2 mL) was purged with oxygen and cooled in an ice water bath. Tris(2,2,6,6-tetramethyl-3,5-heptanedionato)manganese(III) (137 mg, 0.226 mmol) was added as a solid in one portion followed by phenylsilane (0.56 mL, 4.52 mmol) as a neat liquid. The reaction mixture was stirred vigorously for 4 h under a balloon atmosphere of oxygen and then quenched with 10 mL of a 20% aqueous solution of sodium thiosulfate with stirring for 30 min. The mixture was extracted with ethyl acetate, and the combined organics were washed with brine, dried over $MgSO_4$, filtered and concentrated to afford a brown oil which was purified by silica gel chromatography eluted with 0 to 40% EtOAc in hexanes to yield ethyl 2-chloro-4-((2-(2-hydroxypropan-2-yl)benzyl) amino)pyrimidine-5-carboxylate (800 mg, 2.29 mmol, >98% yield). ES [MS] m/z: 350.25 [M+H]$^+$. $^1$H NMR (500 MHz, $CDCl_3$) δ 9.20-9.05 (m, 1H), 8.56 (s, 1H), 7.55-7.48 (m, 1H), 7.36-7.30 (m, 1H), 7.27-7.20 (m, 2H), 5.08 (d, J=6.1 Hz, 2H), 4.26 (q, J=7.1 Hz, 2H), 1.73 (s, 6H), 1.33 (t, J=7.2 Hz, 3H).

Example 71

To a microwave vial equipped with a stir bar and charged with ethyl 2-chloro-4-((2-(2-hydroxypropan-2-yl)benzyl) amino)pyrimidine-5-carboxylate (147 mg, 0.420 mmol), 5-amino-3,3-dimethylisobenzofuran-1(3H)-one (74.5 mg, 0.420 mmol), XantPhos (24.31 mg, 0.042 mmol), $Pd_2(dba)_3$ (38.5 mg, 0.042 mmol), potassium phosphate tribasic (268 mg, 1.26 mmol) was added 1,4-dioxane (8 mL). The vial was purged with an atmosphere of argon, sealed and heated to 100° C. in an oil bath for 9 h. The crude material was filtered and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 40-80% B over 16 minutes, then a 7-minute hold at 100% B; Flow: 20 mL/min. Fractions containing the product were combined and dried via centrifugal evaporation to afford ethyl 2-[(3,3-dimethyl-1-oxo-1,3-dihydro-2-benzofuran-5-yl)amino]-4-({[2-(2-hydroxypropan-2-yl)phenyl] methyl}amino)pyrimidine-5-carboxylate (63 mg, 30.6% yield). HPLC $t_R$: 2.32 min; LC/MS Condition 2. ES [MS] m/z: 491.1 [M+H]$^+$. $^1$H NMR (500 MHz, DMSO-$d_6$) δ 10.39 (br s, 1H), 8.83 (t, J=5.7 Hz, 1H), 8.66 (s, 1H), 8.37 (s, 1H), 7.73-7.68 (m, 2H), 7.38 (br d, J=8.4 Hz, 2H), 7.25-7.15 (m, 2H), 5.34 (s, 1H), 5.12 (d, J=5.9 Hz, 2H), 4.23 (q, J=7.2 Hz, 2H), 3.45-3.38 (m, 2H), 1.58 (s, 6H), 1.49 (s, 6H), 1.29 (t, J=7.0 Hz, 3H).

Example 72

5-{[4-({[2-(2-hydroxypropan-2-yl)phenyl] methyl}amino)-5-(3-methyl-1,2,4-oxadiazol-5-yl) pyrimidin-2-yl]amino}-3,3-dimethyl-1,3-dihydro-2-benzofuran-1-one

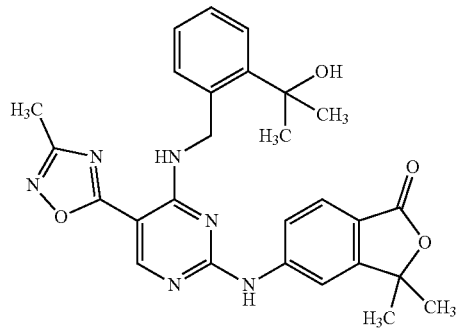

(72)

A vial equipped with a stir bar and charged with ethyl 2-[(3,3-dimethyl-1-oxo-1,3-dihydro-2-benzofuran-5-yl) amino]-4-({[2-(2-hydroxypropan-2-yl)phenyl] methyl}amino)pyrimidine-5-carboxylate (15 mg, 0.031 mmol), N-hydroxyacetimidamide (13.59 mg, 0.183 mmol), and molecular sieves (3 Å, freshly activated, 40 mg) was flushed with nitrogen and treated with EtOH (0.5 mL). After stirring for 5 min, the mixture was treated with sodium ethanolate (21 wt % in ethanol) (0.049 mL, 0.122 mmol). The vial was sealed and placed in an 80° C. bath overnight. The reaction mixture was cooled to room temperature and quenched by addition of solid ammonium chloride (0.22 mmol) and concentrated under a stream of nitrogen. The residue was redissolved in DMF, filtered, and was purified via preparative LC/MS with the following conditions: Column: Waters Xbridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 38-78% B over 19 minutes, then a 4-minute hold at 100% B; Flow: 20 mL/min. Fractions containing the product were combined and dried via centrifugal evaporation to afford 5-{[4-({[2-(2-hydroxypropan-2-yl)phenyl]methyl}amino)-5-(3-methyl-1,2,4-oxadiazol-5-yl)pyrimidin-2-yl]amino}-3,3-dimethyl-1,3-dihydro-2-benzofuran-1-one (9.4 mg, 61.4% yield). HPLC $t_R$: 2.33 min; LC/MS Condition 2. ES [MS] m/z: 501 [M+H]$^+$. $^1$H NMR (500 MHz, DMSO-$d_6$) δ 10.48 (br s, 1H), 8.94 (br t, J=5.9 Hz, 1H), 8.79 (s, 1H), 8.34 (s, 1H), 7.78-7.68 (m, 2H), 7.43-7.36 (m, 2H), 7.25-7.20 (m, 1H), 7.16 (t, J=7.3 Hz, 1H), 5.32 (s, 1H), 5.23 (br d, J=5.9 Hz, 2H), 3.45-3.33 (m, 3H), 2.56-2.54 (m, 2H), 2.38 (s, 3H), 1.61 (s, 6H), 1.49 (s, 6H).

Example 73

5-{[5-(3-cyclopropyl-1,2,4-oxadiazol-5-yl)-4-({[2-(2-hydroxypropan-2-yl)phenyl]methyl}amino)pyrimidin-2-yl]amino}-3,3-dimethyl-1,3-dihydro-2-benzofuran-1-one

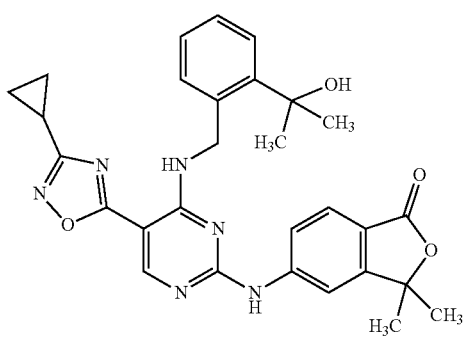

(73)

Example 73 was prepared according to the general preparation procedure for 5-{[4-({[2-(2-hydroxypropan-2-yl)phenyl]methyl}amino)-5-(3-methyl-1,2,4-oxadiazol-5-yl)pyrimidin-2-yl]amino}-3,3-dimethyl-1,3-dihydro-2-benzofuran-1-one. The compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 20 minutes, then a 5-minute hold at 100% B; Flow: 20 mL/min to afford 5-{[5-(3-cyclopropyl-1,2,4-oxadiazol-5-yl)-4-({[2-(2-hydroxypropan-2-yl)phenyl]methyl}amino)pyrimidin-2-yl]amino}-3,3-dimethyl-1,3-dihydro-2-benzofuran-1-one (25.6 mg, 59.6% yield). HPLC $t_R$: 2.52 min; LC/MS Condition 2. ES [MS] m/z: 527.0 [M+H]$^+$. $^1$H NMR (500 MHz, DMSO-d$_6$) δ 10.45 (br s, 1H), 8.78 (t, J=6.1 Hz, 1H), 8.73 (s, 1H), 8.33 (s, 1H), 7.79 (br d, J=8.4 Hz, 1H), 7.71 (d, J=8.4 Hz, 1H), 7.42 (d, J=7.2 Hz, 1H), 7.39-7.36 (m, 1H), 7.23 (t, J=7.7 Hz, 1H), 7.18-7.13 (m, 1H), 5.32 (s, 1H), 5.17 (br d, J=5.9 Hz, 2H), 2.55-2.52 (m, 1H), 2.15-2.09 (m, 1H), 1.58 (s, 6H), 1.53 (s, 6H), 1.03 (br d, J=8.1 Hz, 2H), 0.96 (br s, 2H).

Example 74

5-({4-[(1H-indazol-5-yl)amino]-5-(3-methyl-1,2,4-oxadiazol-5-yl)pyrimidin-2-yl}amino)-3,3-dimethyl-1,3-dihydro-2-benzofuran-1-one

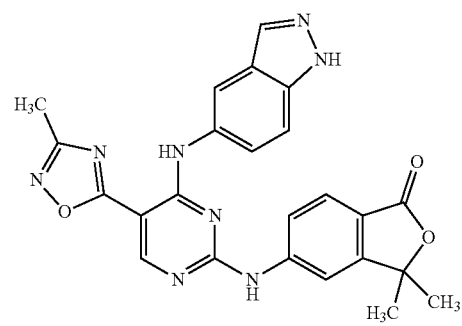

(74)

Preparation 74A: Ethyl 4-((1H-indazol-5-yl)amino)-2-chloropyrimidine-5-carboxylate

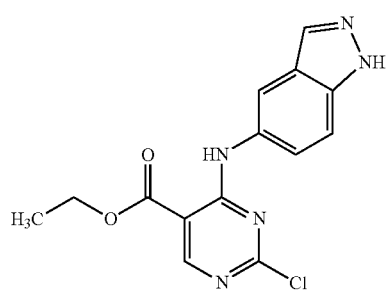

(74A)

To a flask charged with a solution of ethyl 2,4-dichloropyrimidine-5-carboxylate (200 mg, 0.905 mmol) and 1H-indazol-5-amine (120 mg, 0.905 mmol) in acetonitrile (3.6 mL) was added Hünig's Base (474 μl, 2.71 mmol). The reaction mixture was stirred at ambient temperature under N$_2$ (g) for 16 h. The crude material was purified using silica gel chromatography eluting with a gradient of 0 to 100% ethyl acetate in hexanes to afford ethyl 4-((1H-indazol-5-yl)amino)-2-chloropyrimidine-5-carboxylate (208.2 mg, 0.655 mmol, 72.4% yield) as a yellow solid. ES [MS] m/z: 317.9. [M+H]$^+$.

Preparation 74B: Ethyl 4-((1H-indazol-5-yl)amino)-2-((3,3-dimethyl-1-oxo-1,3-dihydroisobenzofuran-5-yl)amino) pyrimidine-5-carboxylate

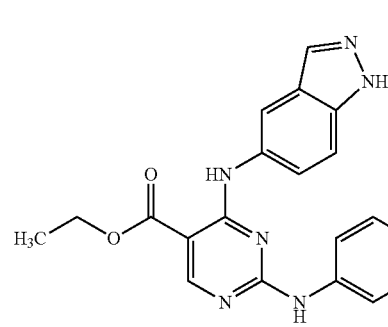

(74B)

Ethyl 4-((1H-indazol-5-yl)amino)-2-chloropyrimidine-5-carboxylate (100 mg, 0.315 mmol) was charged to a vial along with 5-amino-3,3-dimethylisobenzofuran-1(3H)-one (53.1 mg, 0.300 mmol), and a 4 M solution of HCl in dioxane (112 μL, 0.450 mmol). NMP (1.5 mL) was added and the mixture which was stirred at 80° C. under N$_2$ (g) for 16 h. The reaction mixture was then cooled to room temperature and stirred for 16 h after which it was concentrated under reduced pressure and purified by silica gel chromatography eluting with a gradient from 0 to 100% EtOAc in hexanes. Ethyl 4-((1H-indazol-5-yl)amino)-2-((3,3-dimethyl-1-oxo-1,3-dihydroisobenzofuran-5-yl)amino) pyrimidine-5-carboxylate (17.5 mg, 0.035 mmol, 11.8% yield) was afforded as a white solid. HPLC $t_R$: 1.51 min; LC/MS Condition 3. ES [MS] m/z: 459.1 [M+H]$^+$. $^1$H NMR (500 MHz, DMSO-d$_6$) δ 10.30-10.15 (m, 1H), 10.10-9.93 (m, 1H), 8.81-8.68 (m, 1H), 8.11-7.99 (m, 1H), 7.97-7.88 (m, 1H), 7.85-7.75 (m, 1H), 7.73-7.64 (m, 1H), 7.64-7.52 (m, 1H), 7.51-7.36 (m, 2H), 4.37 (q, J=7.0 Hz, 2H), 1.41-1.36 (m, 3H), 1.22-1.12 (m, 6H).

Example 74

To a solution of (Z)—N'-hydroxyacetimidamide (9.0 mg, 0.122 mmol) and ethyl 4-((1H-indazol-5-yl)amino)-2-((3,3-dimethyl-1-oxo-1,3-dihydroisobenzofuran-5-yl)amino) pyrimidine-5-carboxylate (14 mg, 0.031 mmol) in anhydrous ethanol (0.61 mL) were added a 21 wt % solution of sodium ethoxide in ethanol (68.4 μL, 0.183 mmol) and 4 Å molecular sieves (100 mg). The reaction vessel was capped and stirred at 90° C. under nitrogen (g) for 16 h. After cooling to room temperature, the reaction material was diluted in methanol, filtered, and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 19 minutes, then a 4-minute hold at 100% B; Flow: 20 mL/min. Fractions containing the product were combined and dried via centrifugal evaporation to afford 5-({4-[(1H-indazol-5-yl) amino]-5-(3-methyl-1,2,4-oxadiazol-5-yl)pyrimidin-2-yl}amino)-3,3-dimethyl-1,3-dihydro-2-benzofuran-1-one (3.2 mg, 3.2% yield). HPLC $t_R$: 1.66 min; LC/MS Condition 3. ES [MS] m/z: 469.1 [M+H]$^+$. $^1$H NMR (500 MHz, DMSO-d$_6$) δ 8.96-8.80 (m, 1H), 8.12-7.93 (m, 2H), 7.89-7.75 (m, 1H), 7.73-7.56 (m, 2H), 7.44 (s, 2H), 2.48-2.44 (m, 3H), 1.24-1.13 (m, 6H).

Example 75

5-{[5-(3-cyclopropyl-1,2,4-oxadiazol-5-yl)-4-[(1H-indazol-5-yl)amino]pyrimidin-2-yl]amino}-3,3-dimethyl-1,3-dihydro-2-benzofuran-1-one

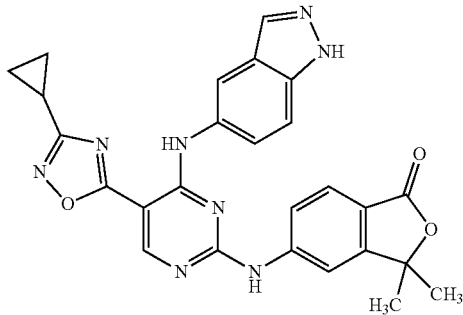

(75)

Example 75 was prepared according to the general preparation procedure 5-({4-[(1H-indazol-5-yl)amino]-5-(3-methyl-1,2,4-oxadiazol-5-yl)pyrimidin-2-yl}amino)-3,3-dimethyl-1,3-dihydro-2-benzofuran-1-one. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 38-78% B over 19 minutes, then a 4-minute hold at 100% B; Flow: 20 mL/min. Fractions containing the product were combined and dried via centrifugal evaporation to afford 5-{[5-(3-cyclopropyl-1,2,4-oxadiazol-5-yl)-4-[(1H-indazol-5-yl) amino]pyrimidin-2-yl]amino}-3,3-dimethyl-1,3-dihydro-2-benzofuran-1-one (2.8 mg, 18.5% yield). HPLC $t_R$: 1.85 min; LC/MS Condition 3. ES [MS] m/z: 495.2 [M+H]$^+$. $^1$H NMR (500 MHz, DMSO-d$_6$) δ 8.96-8.76 (m, 1H), 8.11 (br d, J=8.4 Hz, 1H), 8.01-7.93 (m, 1H), 7.87-7.74 (m, 1H), 7.74-7.57 (m, 2H), 7.54-7.38 (m, 2H), 2.31-2.15 (m, 1H), 1.26-1.17 (m, 6H), 1.16-1.09 (m, 2H), 1.09-1.04 (m, 2H).

Example 76

Ethyl 4-[(3-amino-3-methylbutyl)amino]-2-[(3,3-dimethyl-1-oxo-1,3-dihydro-2-benzofuran-5-yl) amino]pyrimidine-5-carboxylate

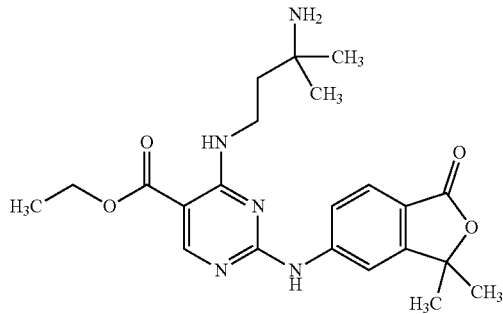

(76)

Preparation 76A: Ethyl 4-((3-((tert-butoxycarbonyl) amino)-3-methylbutyl)amino)-2-chloropyrimidine-5-carboxylate

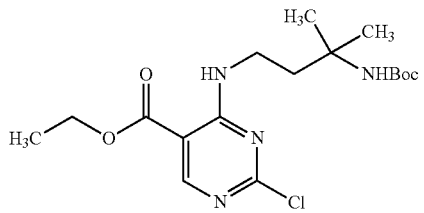

(76A)

To a flask charged with a solution of ethyl 2,4-dichloropyrimidine-5-carboxylate (200 mg, 0.905 mmol) and tert-butyl (4-amino-2-methylbutan-2-yl)carbamate, HCl (216 mg, 0.905 mmol) in acetonitrile (3.6 mL) was added Hünig's Base (474 μl, 2.71 mmol). The reaction mixture was stirred at ambient temperature under N$_2$ (g) for 1 h. The crude material was purified using silica gel chromatography eluting with a gradient from 0 to 25% ethyl acetate in hexanes to afford ethyl 4-((3-((tert-butoxycarbonyl)amino)-3-methylbutyl)amino)-2-chloropyrimidine-5-carboxylate (248 mg, 0.641 mmol, 71% yield) as a yellow oil. ES [MS] m/z: 387.05 [M+H]$^+$.

Example 76

A pressure vessel was charged with ethyl 4-((3-((tert-butoxycarbonyl)amino)-3-methylbutyl)amino)-2-chloropyrimidine-5-carboxylate (100 mg, 0.258 mmol) was charged to a pressure vessel followed by the addition of 5-amino-3,3-dimethylisobenzofuran-1(3H)-one, HCl (55.2 mg, 0.258 mmol), Pd₂(dba)₃ (23.7 mg, 0.026 mmol), Xantphos (29.9 mg, 0.052 mmol), and potassium phosphate tribasic (219 mg, 1.034 mmol). 1,4-Dioxane (646 µL) was added, and the mixture was degassed using nitrogen (g) for 3 min before it was sealed and heated to 90° C. for 16 h. The crude reaction material was diluted with water and DMF. The crude material was purified using silica gel chromatography eluting with a gradient from 0 to 100% ethyl acetate in hexanes. Ethyl 4-((3-((tert-butoxycarbonyl) amino)-3-methylbutyl) amino)-2-((3,3-dimethyl-1-oxo-1,3-dihydroisobenzofuran-5-yl) amino)pyrimidine-5-carboxylate (71.1 mg, 0.135 mmol, 52% yield) was isolated as a colorless oil. The free amine was obtained as a byproduct which was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 12-52% B over 20 minutes, then a 4-minute hold at 100% B; Flow: 20 mL/min. Fractions containing the product were combined and dried via centrifugal evaporation to afford ethyl 4-[(3-amino-3-methylbutyl)amino]-2-[(3,3-dimethyl-1-oxo-1,3-dihydro-2-benzofuran-5-yl)amino]pyrimidine-5-carboxylate (1.3 mg, 1.1% yield). HPLC $t_R$: 1.60 min; LC/MS Condition 2. ES [MS] m/z: 428.1 [M+H]⁺. ¹H NMR (400 MHz, methanol-d₄) δ 8.76-8.62 (m, 1H), 8.09-8.01 (m, 1H), 7.91-7.80 (m, 1H), 7.80-7.68 (m, 1H), 4.71-4.45 (m, 1H), 4.35 (q, J=7.1 Hz, 2H), 3.75 (t, J=7.5 Hz, 2H), 2.02 (br t, J=7.3 Hz, 2H), 1.92 (s, 5H), 1.71-1.66 (m, 6H), 1.47-1.34 (m, 9H).

Example 77

5-({4-[(3-amino-2,2-dimethylpropyl)amino]-5-[3-(oxan-4-yl)-1,2,4-oxadiazol-5-yl]pyrimidin-2-yl}amino)-3,3-dimethyl-1,3-dihydro-2-benzofuran-1-one

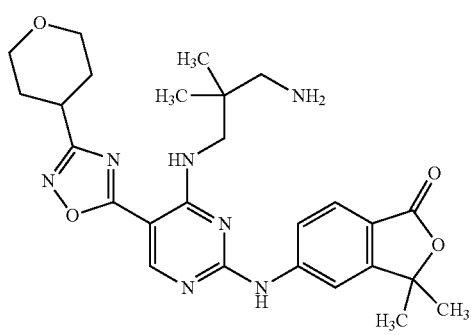

(77)

Preparation 77A: Ethyl 4-((3-((tert-butoxycarbonyl)amino)-2,2-dimethylpropyl)amino)-2-chloropyrimidine-5-carboxylate

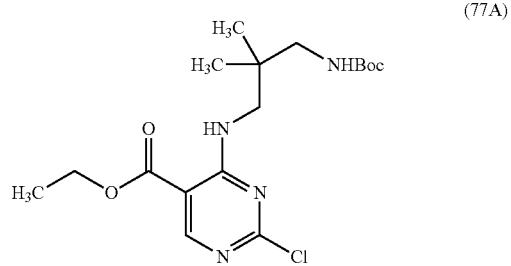 [SMILES: CCOC(=O)c1cnc(Cl)nc1NCC(C)(C)CNC(=O)OC(C)(C)C]

(77A)

To a solution of ethyl 2,4-dichloropyrimidine-5-carboxylate (750 mg, 3.39 mmol) and tert-butyl (3-amino-2,2-dimethylpropyl)carbamate (686 mg, 3.39 mmol) in acetonitrile (13 mL) was added Hünig's base (1778 µL, 10.18 mmol). The reaction mixture was stirred at ambient temperature under N₂ (g) for 1 h. The crude material was purified by silica gel chromatography eluting with a gradient from 0 to 25% ethyl acetate in hexanes to afford ethyl 4-((3-((tert-butoxycarbonyl)amino)-2,2-dimethylpropyl) amino)-2-chloropyrimidine-5-carboxylate (1.22 g, 3.17 mmol, 93% yield) as a yellow solid. ES [MS] m/z: 528.2 [M+H]⁺.

Preparation 77B: Ethyl 4-((3-((tert-butoxycarbonyl) amino)-2,2-dimethylpropyl)amino)-2-((3,3-dimethyl-1-oxo-1,3-dihydroisobenzofuran-5-yl)amino) pyrimidine-5-carboxylate

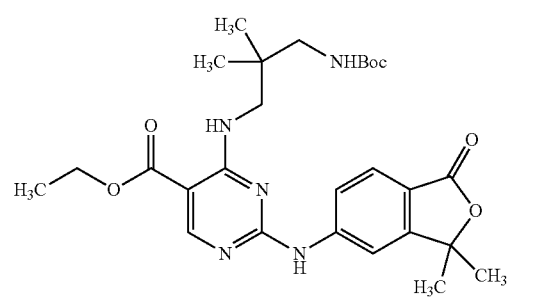

(77B)

A solution of ethyl 4-((3-((tert-butoxycarbonyl)amino)-2,2-dimethylpropyl) amino)-2-chloropyrimidine-5-carboxylate (400 mg, 1.034 mmol), 5-amino-3,3-dimethylisobenzofuran-1(3H)-one, HCl (221 mg, 1.034 mmol), Pd₂(dba)₃ (95 mg, 0.103 mmol), Xantphos (120 mg, 0.207 mmol), and potassium phosphate tribasic (878 mg, 4.14 mmol) in 1,4-dioxane (2.6 mL) in a pressure vessel was degassed using N₂ (g) for 3 min before it was heated to 90° C. for 16 h. The crude reaction material was diluted with water and DMF. The crude material was purified using silica gel chromatography eluting with a gradient from 0 to 100% ethyl acetate in hexanes to afford ethyl 4-((3-((tert-butoxycarbonyl) amino)-2,2-dimethylpropyl)amino)-2-((3,3-dimethyl-1-oxo-1,3-dihydroisobenzofuran-5-yl)amino)pyrimidine-5- carboxylate (276 mg, 0.523 mmol, 51% yield) as a colorless oil. ES [MS] m/z: 387.1 [M+H]+.

Example 77

(Z)—N'-hydroxytetrahydro-2H-pyran-4-carboximidamide (24.6 mg, 0.171 mmol), ethyl 4-((3-((tert-butoxycarbonyl)amino)-2,2-dimethylpropyl)amino)-2-((3,3-dimethyl-1-oxo-1,3-dihydroisobenzofuran-5-yl)amino)pyrimidine-5-carboxylate (30 mg, 0.057 mmol), sodium ethoxide (106 μL, 0.284 mmol), and 4 Å molecular sieves (100 mg) were stirred in anhydrous ethanol (1.2 mL) at 90° C. under nitrogen (g) for 5 h. The reaction mixture was heated for an additional 16 h at 90° C. All volatiles had evaporated and conversion to the free amine was complete. Methanol and DMF (1 mL each) was added, the reaction mixture was filtered, and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 10-90% B over 18 minutes, then a 5-minute hold at 100% B; Flow: 20 mL/min. Fractions containing the product were combined and dried via centrifugal evaporation to afford 5-({4-[(3-amino-2,2-dimethylpropyl)amino]-5-[3-(oxan-4-yl)-1,2,4-oxadiazol-5-yl]pyrimidin-2-yl}amino)-3,3-dimethyl-1,3-dihydro-2-benzofuran-1-one (9.2 mg, 30.6% yield). HPLC $t_R$: 1.67 min; LC/MS Condition 3. ES [MS] m/z: 508.3 [M+H]+. 1H NMR (500 MHz, DMSO-$d_6$) δ 8.88-8.68 (m, 1H), 8.54-8.41 (m, 1H), 7.82-7.57 (m, 2H), 4.01-3.85 (m, 2H), 3.60-3.42 (m, 2H), 3.25-3.08 (m, 1H), 1.99-1.87 (m, 5H), 1.85-1.73 (m, 2H), 1.71-1.56 (m, 7H), 1.03-0.93 (m, 6H).

Example 78

5-{[5-(3-cyclopropyl-1,2,4-oxadiazol-5-yl)-4-{[(1S)-2-hydroxy-1-phenylethyl]amino}pyridin-2-yl] amino}-3,3-dimethyl-1,3-dihydro-2-benzofuran-1-one

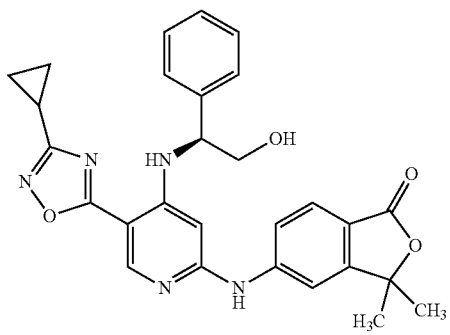

(78)

Preparation 78A: (S)-methyl 6-chloro-4-((2-hydroxy-1-phenylethyl)amino)nicotinate

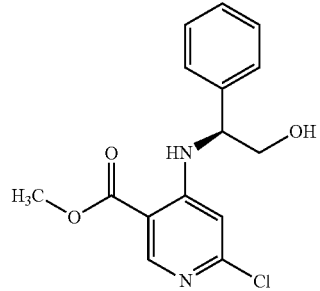

(78A)

A solution of methyl 4,6-dichloronicotinate (1.5 g, 7.3 mmol), (S)-2-amino-2-phenylethanol (1.0 g, 7.3 mmol), and Hünig's Base (1.65 mL, 9.46 mmol) in acetonitrile (8 mL) was stirred at 50° C. under $N_2$ (g) for 72 h. The crude reaction material was loaded directly onto a silica gel column and purified by eluting with a gradient from 0 to 80% ethyl acetate in hexanes to afford (S)-methyl 6-chloro-4-((2-hydroxy-1-phenylethyl) amino)nicotinate (1.85 g, 6.03 mmol, 83% yield) as a white solid. ES [MS] m/z: 306.95 [M+H]+. 1H NMR (400 MHz, CDCl3) δ 8.86-9.10 (1H, m), 8.58-8.75 (1H, m), 7.29-7.43 (5H, m), 6.32-6.39 (1H, m), 4.55-4.65 (1H, m), 3.96-4.06 (1H, m), 3.86-3.95 (4H, m), 1.99 (1H, br. s.).

Preparation 78B: (S)-methyl 6-((3,3-dimethyl-1-oxo-1,3-dihydroisobenzofuran-5-yl) amino)-4-((2-hydroxy-1-phenylethyl)amino)nicotinate

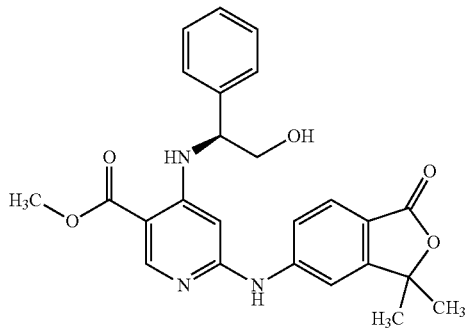

(78B)

A solution of (S)-methyl 6-chloro-4-((2-hydroxy-1-phenylethyl)amino)nicotinate (145 mg, 0.473 mmol), 5-amino-3,3-dimethylisobenzofuran-1(3H)-one (101 mg, 0.567 mmol), Pd2(dba)3 (43.3 mg, 0.047 mmol), Xantphos (54.7 mg, 0.095 mmol), and potassium phosphate tribasic (401 mg, 1.891 mmol) in 1,4-dioxane (1.2 mL) in a pressure vessel was degassed using $N_2$ (g) for 3 min before it was heated to 90° C. for 16 h. The reaction mixture was diluted with water and DMF, loaded onto a silica gel column, and purified by eluting with a gradient from 0 to 100% ethyl acetate in hexanes followed by a gradient of 0 to 40% of a 10:90 solution of ammonium hydroxide in methanol:ethyl acetate. (S)-methyl 6-((3,3-dimethyl-1-oxo-1,3-dihydroisobenzofuran-5-yl)amino)-4-((2-hydroxy-1-phenylethyl)amino)nicotinate (43.3 mg, 0.097 mmol, 20% yield) was afforded as a white solid. ES [MS] m/z: 448.05 [M+H]⁺.

Example 78

(Z)—N'-hydroxycyclopropanecarboximidamide (18.8 mg, 0.188 mmol), (S)-methyl 6-((3,3-dimethyl-1-oxo-1,3-dihydroisobenzofuran-5-yl)amino)-4-((2-hydroxy-1-phenylethyl)amino)nicotinate (21 mg, 0.047 mmol), sodium ethoxide (105 μL, 0.282 mmol), anhydrous ethanol (1.0 mL) and 4 Å molecular sieves (100 mg) were added to a pressure-relief vial. The vial was capped and the reaction mixture was stirred at 90° C. under nitrogen (g) for 3 h. The crude reaction mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 36-76% B over 23 minutes, then a 4-minute hold at 100% B; Flow: 20 mL/min. Fractions containing the product were combined and dried via centrifugal evaporation to afford 5-{[5-(3-cyclopropyl-1,2,4-oxadiazol-5-yl)-4-{[(1S)-2-hydroxy-1-phenylethyl]amino}pyridin-2-yl]amino}-3,3-dimethyl-1,3-dihydro-2-benzofuran-1-one (5.7 mg, 23.2% yield). HPLC $t_R$: 1.58 min; LC/MS Condition 3. ES [MS] m/z: 498.2 [M+H]⁺. $^1$H NMR (500 MHz, DMSO-d₆) δ 9.62-9.49 (m, 1H), 8.72-8.58 (m, 2H), 7.98-7.76 (m, 1H), 7.67-7.50 (m, 2H), 7.40-7.34 (m, 4H), 7.33-7.24 (m, 1H), 6.05-6.01 (m, 1H), 4.68-4.61 (m, 1H), 3.91-3.83 (m, 1H), 3.65 (s, 1H), 2.25-2.17 (m, 1H), 1.58 (d, J=5.1 Hz, 6H), 1.17-1.02 (m, 4H).

Example 79

5-{[5-(3-cyclopropyl-1,2,4-oxadiazol-5-yl)-4-{[(1S)-1-cyclopropyl-2-hydroxyethyl]amino}pyridin-2-yl]amino}-3,3-dimethyl-1,3-dihydro-2-benzofuran-1-one

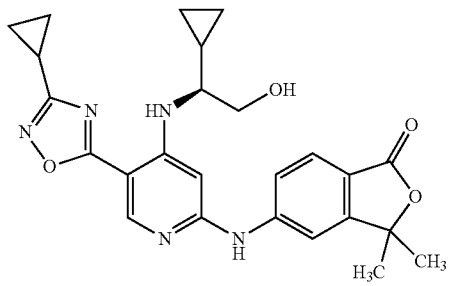

(79)

Example 79 was prepared according to the general sequence of transformations described for the preparation of 5-{[5-(3-cyclopropyl-1,2,4-oxadiazol-5-yl)-4-{[(1S)-1-cyclopropyl-2-hydroxyethyl]amino}pyridin-2-yl]amino}-3,3-dimethyl-1,3-dihydro-2-benzofuran-1-one using (S)-2-amino-2-cyclopropylethan-1-ol instead of (S)-phenylglycinol. The final compound was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the product were combined and dried via centrifugal evaporation to afford 5-{[5-(3-cyclopropyl-1,2,4-oxadiazol-5-yl)-4-{[(1S)-1-cyclopropyl-2-hydroxyethyl]amino}pyridin-2-yl]amino}-3,3-dimethyl-1,3-dihydro-2-benzofuran-1-one (8.3 mg, 24.2% yield). HPLC $t_R$: 1.64 min; LC/MS Condition 3. ES [MS] m/z: 462.2 [M+H]⁺. $^1$H NMR (500 MHz, DMSO-d₆) δ 9.78 (s, 1H), 8.63 (s, 1H), 8.02 (d, J=8.1 Hz, 1H), 7.97 (s, 1H), 7.67 (s, 2H), 6.27 (s, 1H), 5.02 (t, J=5.1 Hz, 1H), 3.65-3.56 (m, 2H), 3.20 (br s, 1H), 2.55-2.51 (m, 1H), 2.19 (br t, J=4.4 Hz, 1H), 1.59 (s, 6H), 1.12 (br d, J=8.4 Hz, 3H), 1.05 (br d, J=5.1 Hz, 1H), 0.98 (br d, J=4.0 Hz, 1H), 0.53-0.44 (m, 2H), 0.40 (br s, 1H), 0.25 (br d, J=5.1 Hz, 1H).

Example 80

5-{[5-(3-{1-azabicyclo[2.2.2]octan-4-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one

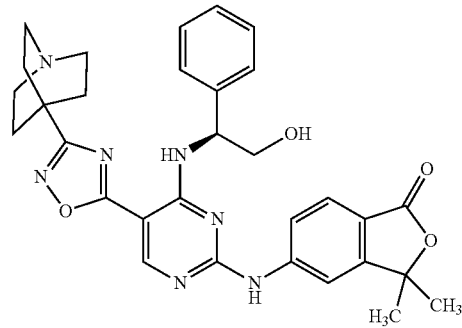

(80)

A 5 mL vial was charged with (S)-ethyl 2-((3,3-dimethyl-1-oxo-1,3-dihydroisobenzofuran-5-yl)amino)-4-((2-hydroxy-1-phenylethyl)amino)pyrimidine-5-carboxylate (40.0 mg, 0.086 mmol), N-hydroxyquinuclidine-4-carboximidamide (43.9 mg, 0.259 mmol), and EtOH (1.5 mL). The vial was flushed with nitrogen and treated with 40 mg molecular sieves (3 Å, freshly activated). After stirring 5 minutes, sodium ethanolate (0.126 mL, 0.346 mmol) was added to the reaction mixture. The vial was sealed under nitrogen and heated to 80° C. overnight with stirring. LCMS indicated completion of the reaction. The reaction mixture was cooled to room temperature, diluted with 5% EtOH/EtOAc and brine. The organic layer was dried over MgSO₄, and concentrated to obtain a crude sample. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 20 minutes, then a 4-minute hold at 100% B; Flow: 20 mL/min. Fractions containing the product were combined and dried via centrifugal evaporation to afford 5-{[5-(3-cyclopropyl-1,2,4-oxadiazol-5-yl)-4-{[(1S)-1-cyclopropyl-2-hydroxyethyl]amino}pyridin-2-yl]amino}-3,3-dimethyl-1,3-dihydro-2-benzofuran-1-one (19 mg, 36% yield). HPLC $t_R$: 1.73 min; LC/MS Condition 3. ES [MS] m/z: 568.2 [M+H]⁺. $^1$H NMR (DMSO-d₆, 500 MHz): δ (ppm) 10.44 (br s, 1H), 9.29 (br d, J=7.7 Hz, 1H), 8.81 (s, 1H), 8.01 (s, 1H), 7.64-7.73 (m, 2H), 7.37-7.45 (m, 4H), 7.27-7.33 (m, 1H), 5.34-5.39 (m, 1H), 3.84-3.96 (m, 2H), 3.18 (s, 1H), 3.08 (br t, J=7.7 Hz, 4H), 2.53-2.56 (m, 1H), 1.91-2.02 (m, 6H), 1.57-1.62 (m, 3H), 1.54 (s, 3H).

Example 81

2-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b]pyridin-5-one

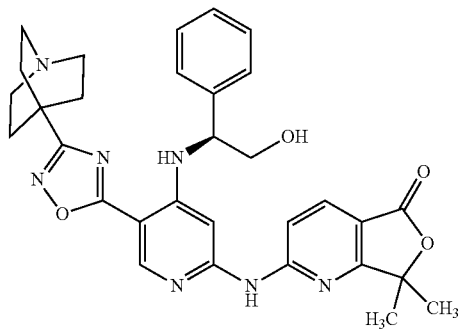

Preparation 81A: 6-amino-2-chloronicotinonitrile

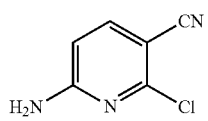

To a solution of 2,6-dichloronicotinonitrile (6.500 g, 37.6 mmol) at room temperature were added (4-methoxyphenyl)methanamine (5.15 g, 37.6 mmol) and diisopropylethylamine (13.09 mL, 75 mmol). The reaction mixture was heated at 90° C. for 6 hours. Intermediate 2-chloro-6-((4-methoxybenzyl)amino)nicotinonitrile was formed as observed by LC/MS analysis: ES [MS] m/z: 273.9 [M+H]⁺. The mixture was cooled, diluted with EtOAc, and washed with brine. The organic layer was dried over MgSO₄, and concentrated. The residue was suspended in DCM (10 mL) followed by the slow addition of TFA (28.8 mL, 376 mmol). The mixture was heated to 50° C. with stirring for 5 h. LCMS showed that the reaction was complete. A majority of the solvent was removed under reduced pressure and the remaining light brown solution was diluted with DCM, followed by a slow addition of an aqueous saturated solution of NaHCO₃ to adjust the pH to ~7. During the addition of the aqueous NaHCO₃, a precipitate was formed which was collected by filtration and rinsed with water. The material was air-dried overnight to afford 6-amino-2-chloronicotinonitrile (4.83 g, 31.5 mmol, 84% yield). ¹H NMR (400 MHz, CDCl₃) δ 7.65 (d, J=8.5 Hz, 1H), 6.45 (d, J=8.5 Hz, 1H), 5.19 (br. s., 2H).

Preparation 81B:
6-amino-2-(prop-1-en-2-yl)nicotinonitrile

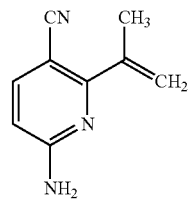

To a 40 mL pressure vial were added 6-amino-2-chloronicotinonitrile (1.000 g, 6.51 mmol), 4,4,5,5-tetramethyl-2-(prop-1-en-2-yl)-1,3,2-dioxaborolane (1.423 g, 8.47 mmol), K₂CO₃ (1.350 g, 9.77 mmol), followed by 1,2-dimethoxyethane (16 mL), water (8 mL) and then Pd(PPh₃)₄ (0.226 g, 0.195 mmol). Argon was bubbled through the mixture. The reaction mixture was heated at 80° C. overnight in a heating block. The reaction mixture was cooled to room temperature, diluted with EtOAc, and washed with brine. The organic layer was separated and concentrated. The material was purified using silica gel chromatography eluting with 0-80% B/DCM over 13 minutes. [B=10% 2 N NH₃ in MeOH/EtOAc]. The appropriate fractions were concentrated to afford 6-amino-2-(prop-1-en-2-yl)nicotinonitrile (0.878 g, 5.52 mmol, 85% yield), as an off-white solid. ¹H NMR (400 MHz, DMSO-d₆) δ 7.70 (d, J=8.8 Hz, 1H), 7.01 (br. s., 2H), 6.42 (d, J=8.8 Hz, 1H), 5.49-5.43 (m, 2H), 2.07 (t, J=1.1 Hz, 3H).

Preparation 81C:
6-amino-2-(2-hydroxypropan-2-yl)nicotinonitrile

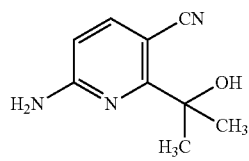

To a 200 mL round bottom flask were added 6-amino-2-(prop-1-en-2-yl) nicotinonitrile (875.00 mg, 5.50 mmol), DCM (2 mL), 2-propanol (40 mL), phenylsilane (1190 mg, 10.99 mmol), and tris(2,2,6,6-tetramethyl-3,5-heptanedionato)manganese(III) (332 mg, 0.550 mmol). The reaction mixture was cooled to 0° C. The air was removed from the flask. The reaction mixture was stirred under an atmosphere of oxygen (balloon) in an ice-water bath. After about 2 hours, LC/MS showed the reaction was complete, ES [MS] m/z: 178.1 [M+H]⁺. The reaction mixture was filtered through a pad of celite, and concentrated.

Preparation 81D: 2-amino-7,7-dimethylfuro[3,4-b]pyridin-5(7H)-one

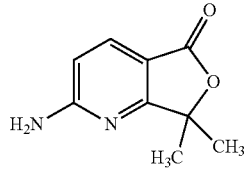

(81D)

To a 500 mL round bottom flask were added 6-amino-2-(2-hydroxypropan-2-yl) nicotinonitrile (6.76 g, 38.1 mmol), DMF (50 mL), water (50 mL) and NaHCO$_3$(12.82 g, 153 mmol). The reaction mixture was stirred and heated to 75° C. After 5 days, LC/MS showed a complete consumption of the starting material. The reaction mixture was cooled to room temperature, and diluted with 10% EtOH/EtOAc, and washed with brine. The organic layer was separated and washed with brine, dried over MgSO$_4$, filtered and concentrated. The material was purified using silica gel chromatography eluting with 0-20% B/DCM [B=1:1 solution of THF and acetonitrile] to afford 2-amino-7,7-dimethylfuro[3,4-b]pyridin-5(7H)-one (5.21 g, 29.2 mmol, 77% yield) as an off-white solid. ES [MS] m/z: 179.1 [M+H]$^+$. $^1$H NMR (DMSO-d$_6$, 400 MHz): δ (ppm) 7.69 (d, J=8.5 Hz, 1H), 7.33 (s, 2H), 6.50 (d, J=8.5 Hz, 1H), 1.50 (s, 6H).

Example 81

A vial charged with (S)-methyl 6-((7,7-dimethyl-5-oxo-5,7-dihydrofuro[3,4-b]pyridin-2-yl)amino)-4-((2-hydroxy-1-phenylethyl)amino)nicotinate (45.0 mg, 0.100 mmol), N-hydroxyquinuclidine-4-carboximidamide (50.9 mg, 0.301 mmol), and molecular sieves (3 Å, freshly activated, 40 mg) was flushed with nitrogen and treated with EtOH (3 mL). After stirring for 5 min, the mixture was treated with sodium ethanolate (0.146 mL, 0.401 mmol). The vial was sealed and placed in an 80° C. bath overnight. After cooling to room temperature, the reaction mixture was concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 8-48% B over 20 minutes, then a 5-minute hold at 100% B; Flow: 20 mL/min. Fractions containing the desired product were combined and dried via centrifugal evaporation to afford 2-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b]pyridin-5-one (10.6 mg, 18% yield). HPLC t$_R$: 1.23 min; LC/MS Condition 2. ES [MS] m/z: 568.1 [M+H]$^+$. $^1$H NMR (500 MHz, DMSO-d$_6$) δ 8.93 (d, J=7.1 Hz, 1H), 8.70 (s, 1H), 7.97 (d, J=8.8 Hz, 1H), 7.58 (br d, J=9.2 Hz, 1H), 7.45 (s, 1H), 7.40-7.35 (m, 4H), 7.28 (br d, J=6.2 Hz, 1H), 4.75 (br d, J=5.1 Hz, 1H), 3.95 (br dd, J=11.0, 4.4 Hz, 1H), 3.80 (br dd, J=10.3, 5.1 Hz, 1H), 3.01 (br t, J=7.5 Hz, 4H), 1.98-1.92 (m, 6H), 1.91 (s, 2H), 1.62 (s, 3H), 1.46 (s, 3H).

Example 82

2-{[5-(3-{1-azabicyclo[2.2.2]octan-4-yl}-1,2,4-oxadiazol-5-yl)-4-{1[(1S)-1-(4-fluorophenyl)-2-hydroxyethyl]amino}pyridin-2-yl]amino}-7,7-dimethyl-5H,7H-furo [3,4-b]pyridin-5-one

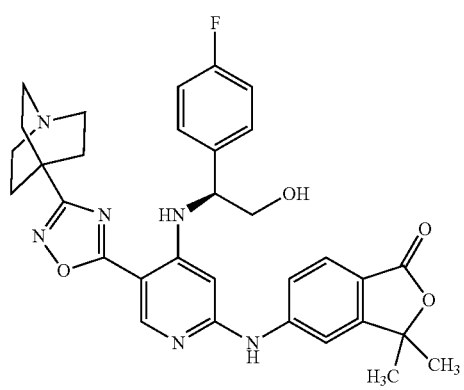

(82)

To a solution of (S)-methyl 6-((7,7-dimethyl-5-oxo-5,7-dihydrofuro[3,4-b]pyridin-2-yl)amino)-4-((1-(4-fluorophenyl)-2-hydroxyethyl)amino)nicotinate (17 mg, 0.036 mmol) in anhydrous ethanol (1 mL) at room temperature under a nitrogen atmosphere was added N-hydroxyquinuclidine-4-carboximidamide (24.67 mg, 0.146 mmol) and molecular sieves (3 Å, freshly activated, 50 mg), followed by the additional of sodium ethanolate (0.082 mL, 0.219 mmol). The reaction mixture was stirred at room temperature for 5 min, and then heated to 80° C. for 2 hours. After cooling to room temperature, the reaction mixture was filtered. The filtrate was concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 16-56% B over 20 minutes, then a 6-minute hold at 100% B; Flow: 20 mL/min. Fractions containing the product were combined and dried via centrifugal evaporation to afford (S)-2-((4-((1-(4-fluorophenyl)-2-hydroxyethyl)amino)-5-(3-(quinuclidin-4-yl)-1,2,4-oxadiazol-5-yl)pyridin-2-yl)amino)-7,7-dimethylfuro[3,4-b]pyridin-5(7H)-one (2.5 mg, 10.2% yield). HPLC t$_R$: 1.45 min; LC/MS Condition 2. ES [MS] m/z: 586.2 [M+H]$^+$. $^1$H NMR (500 MHz, DMSO-d$_6$) δ 10.48 (s, 1H), 8.91 (d, J=7.0 Hz, 1H), 8.71 (s, 1H), 7.99 (d, J=8.4 Hz, 1H), 7.65 (d, J=8.8 Hz, 1H), 7.42 (dd, J=8.6, 5.7 Hz, 2H), 7.37 (s, 1H), 7.19 (t, J=8.8 Hz, 2H), 4.80-4.70 (m, 1H), 4.01-3.91 (m, 1H), 3.80 (br d, J=8.4 Hz, 1H), 3.10 (br t, J=7.5 Hz, 2H), 2.54-2.47 (m, 4H), 2.00 (br dd, J=8.4, 6.2 Hz, 6H), 1.92 (s, 1H), 1.62 (s, 3H), 1.46 (s, 3H).

Example 83

2-{[5-(3-{4-fluoro-1-azabicyclo[2.2.2]octan-3-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b]pyridin-5-one

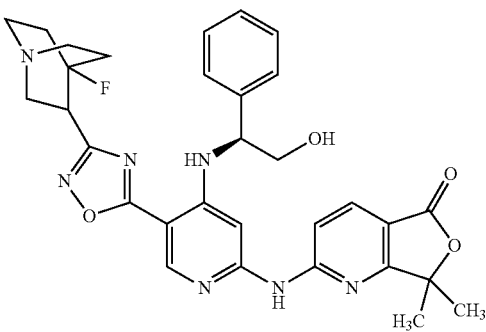
(83)

Preparation 83A:
Rac-(1r,4r)-4-fluoroquinuclidine-3-carbonitrile

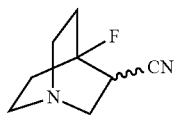
(83A)

1-((Isocyanomethyl)sulfonyl)-4-methylbenzene (235 mg, 1.21 mmol) in EtOH (107 μL) was added to a stirred solution of (1r,4r)-4-fluoroquinuclidin-3-one (138 mg, 0.964 mmol) in DME (3.75 mL) at ambient temperature. The reaction mixture was cooled to 0° C. before potassium tert-butoxide in THF (1 M, 3130 μL, 3.13 mmol) was added in two portions over 5 min. The reaction mixture was then removed from the cold bath and allowed to warm to ambient temperature. The reaction mixture was stirred for 16 h. The solids were filtered away, and the volatiles were removed under positive N$_2$ (g) pressure to afford (1r,4r)-4-fluoroquinuclidine-3-carbonitrile.

Preparation 83B: Rac-(1r,4r,Z)-4-fluoro-N'-hydroxyquinuclidine-3-carboximidamide

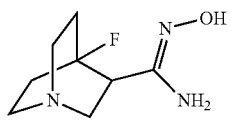
(83B)

A solution of rac-(1r,4r)-4-fluoroquinuclidine-3-carbonitrile (149 mg, 0.966 mmol) and hydroxylamine (592 μL, 9.66 mmol) were stirred in ethanol (1.61 mL) under N$_2$ (g) at 80° C. for 16 h. The reaction mixture was allowed to cool to ambient temperature, and the volatiles were removed under positive N$_2$ (g) pressure. The solids were dissolved in water (2 mL) and DCM (2 mL). The layers were separated, and the aqueous layer was washed with a second portion of DCM (2 mL). The aqueous layer was then extracted with a 1:1 mixture of isopropanol:chloroform (3×10 mL). The combined organics were dried over sodium sulfate, the solids were filtered away, and the volatiles were removed under reduced pressure. Rac-(r,4r,Z)-4-fluoro-N'-hydroxyquinuclidine-3-carboximidamide (106 mg, 0.564 mmol, 58.3% yield) was isolated as pale-yellow solid. $^1$H NMR (500 MHz, methanol-d$_4$) δ 3.59-3.52 (m, 1H), 3.20-2.91 (m, 5H), 2.82-2.73 (m, 1H), 2.18-2.06 (m, 1H), 1.95-1.83 (m, 2H), 1.71-1.60 (m, 1H).

Example 83

Example 83 was prepared according to the general procedure for 2-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b]pyridin-5-one using rac-(1r,4r,Z)-4-fluoro-N'-hydroxyquinuclidine-3-carboximidamide. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-60% B over 26 min, then a 4-min hold at 100% B; Flow: 20 mL/min. Fractions containing the desired product were combined and dried via centrifugal evaporation to afford 2-{[5-(3-{4-fluoro-1-azabicyclo[2.2.2]octan-3-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b]pyridin-5-one (3.6 mg, 6% yield). HPLC t$_R$: 0.840 min; LC/MS Condition 1. ES [MS] m/z: 586.10 [M+H]$^+$. $^1$H NMR (500 MHz, DMSO-d$_6$) δ 10.49 (s, 1H), 8.77-8.70 (m, 2H), 7.99 (d, J=8.8 Hz, 1H), 7.63 (d, J=8.8 Hz, 1H), 7.43 (s, 1H), 7.40-7.33 (m, 4H), 7.30-7.22 (m, 1H), 5.17 (t, J=5.1 Hz, 1H), 4.82-4.73 (m, 1H), 4.00-3.92 (m, 1H), 3.74 (dt, J=10.8, 5.6 Hz, 1H), 3.56-3.47 (m, 1H), 3.42-3.32 (m, 1H), 3.13-3.01 (m, 1H), 2.99-2.88 (m, 1H), 2.34-2.23 (m, 1H), 1.93-1.77 (m, 2H), 1.68-1.54 (m, 4H), 1.46 (s, 3H).

Example 84

2-{[5-(3-{1-azabicyclo[2.2.2]octan-4-yl}-1,2,4-oxadiazol-5-yl)-4-{[(1,3-thiazol-2-yl) methyl]amino}pyridin-2-yl]amino}-7,7-dimethyl-5H,7H-furo[3,4-b]pyridin-5-one

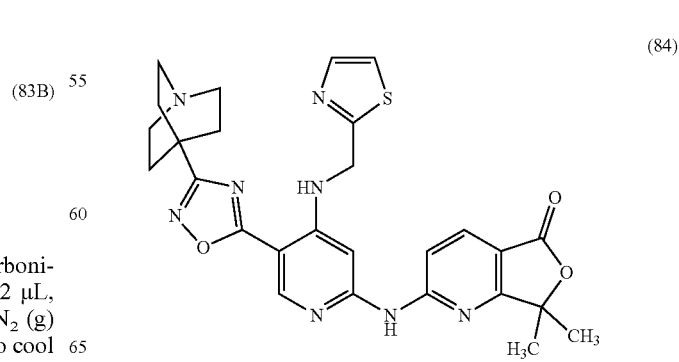
(84)

Preparation 84A: Methyl 6-chloro-4-((thiazol-2-ylmethyl)amino)nicotinate

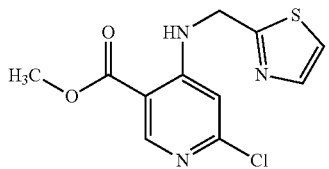

(84A)

Methyl 4,6-dichloronicotinate (632 mg, 3.07 mmol), thiazol-2-ylmethanamine (291 µL, 3.07 mmol), and Hünig's base (1610 µL, 9.20 mmol) were stirred at 50° C. under $N_2$ (g) for 16 h. Upon cooling to ambient temperature, a crystalline solid precipitated from solution. The solid was filtered from the reaction mixture and washed with water (20 mL) and a minimal amount of methanol (5 mL). Methyl 6-chloro-4-((thiazol-2-ylmethyl)amino)nicotinate (521 mg, 1.84 mmol, 60% yield) was isolated as a pale-yellow solid. HPLC $t_R$: 0.94 min; LC/MS Condition 1. ES [MS] m/z: 284.0 [M+H]$^+$. $^1$H NMR (500 MHz, DMSO-$d_6$) δ 8.88-8.79 (m, 1H), 8.61-8.56 (m, 1H), 7.82-7.80 (m, 1H), 7.70-7.68 (m, 1H), 6.90 (s, 1H), 4.96-4.92 (m, 2H), 3.89-3.85 (m, 3H), 3.33-3.30 (m, 3H).

Preparation 84B: Methyl 6-((7,7-dimethyl-5-oxo-5,7-dihydrofuro[3,4-b]pyridin-2-yl) amino)-4-((thiazol-2-ylmethyl)amino)nicotinate

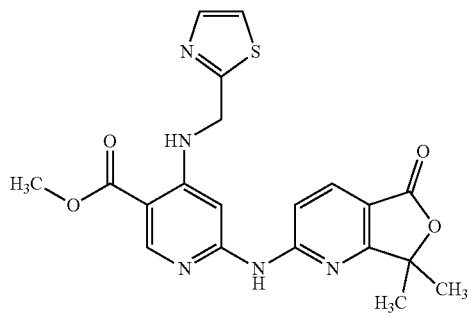

(84B)

A solution of methyl 6-chloro-4-((thiazol-2-ylmethyl)amino)nicotinate (250 mg, 0.881 mmol), 2-amino-7,7-dimethylfuro[3,4-b]pyridin-5(7H)-one (188 mg, 1.06 mmol), Pd$_2$(dba)$_3$ (81.0 mg, 0.088 mmol), Xantphos (102 mg, 0.176 mmol), and potassium phosphate tribasic (748 mg, 3.52 mmol) in 1,4-dioxane (2.20 mL) in a pressure vessel was degassed using $N_2$ for 3 min before it was heated to 90° C. for 16 h. The crude reaction material was loaded onto a silica gel column and purified using ethyl acetate in hexanes (0-100%) followed by methanol with 10% ammonium hydroxide in ethyl acetate (0-40%). Methyl 6-((7,7-dimethyl-5-oxo-5,7-dihydrofuro[3,4-b]pyridin-2-yl)amino)-4-((thiazol-2-ylmethyl)amino)nicotinate (356 mg, 0.836 mmol, 95% yield) was isolated as a white solid. HPLC $t_R$: 1.222 min; ESI [M+H] m/z: 426.25 (LC/MS condition 6). $^1$H NMR (500 MHz, DMSO-$d_6$) δ 10.46 (s, 1H), 8.70 (t, J=6.4 Hz, 1H), 8.64-8.62 (m, 1H), 7.96 (d, J=8.4 Hz, 1H), 7.77-7.75 (m, 1H), 7.75-7.73 (m, 1H), 7.58 (d, J=3.3 Hz, 1H), 7.42 (d, J=8.4 Hz, 1H), 4.90 (d, J=6.2 Hz, 2H), 3.86 (s, 3H), 1.52 (s, 6H).

Example 84

A solution of (Z)—N'-hydroxyquinuclidine-4-carboximidamide (23.9 mg, 0.141 mmol), methyl 6-((7,7-dimethyl-5-oxo-5,7-dihydrofuro[3,4-b]pyridin-2-yl)amino)-4-((thiazol-2-ylmethyl)amino)nicotinate (20.0 mg, 0.047 mmol), sodium ethoxide (88.0 µL, 0.235 mmol), and 4 Å molecular sieves (100 mg) was stirred at 90° C. under $N_2$ for 16 h. After cooling to room temperature, the reaction material was diluted in methanol, filtered, and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 13-53% B over 19 min, then a 4-min hold at 100% B; Flow: 20 mL/min. Fractions containing the product were combined and dried via centrifugal evaporation to afford 2-{[5-(3-{1-azabicyclo[2.2.2]octan-4-yl}-1,2,4-oxadiazol-5-yl)-4-{[(1,3-thiazol-2-yl)methyl]-amino}pyridin-2-yl]amino}-7,7-dimethyl-5H,7H-furo[3,4-b]pyridin-5-one (6.3 mg, 25% yield). HPLC $t_R$: 0.767 min; LC/MS Condition 1. ES [MS]m/z: 545.1 [M+H]$^+$. $^1$H NMR (500 MHz, DMSO-$d_6$) δ 8.78-8.72 (m, 2H), 8.00 (d, J=8.8 Hz, 1H), 7.89 (s, 1H), 7.81 (d, J=3.3 Hz, 1H), 7.64 (d, J=3.3 Hz, 1H), 7.50 (d, J=8.8 Hz, 1H), 5.02 (d, J=6.2 Hz, 2H), 3.10-3.01 (m, 4H), 2.02-1.93 (m, 6H), 1.92 (s, 2H), 1.55 (s, 6H).

Example 85

2-{[5-(3-{1-azabicyclo[2.2.2]octan-4-yl}-1,2,4-oxadiazol-5-yl)-4-{[(pyridin-3-yl)methyl]amino}pyridin-2-yl]amino}-7,7-dimethyl-5H,7H-furo[3,4-b]pyridin-5-one

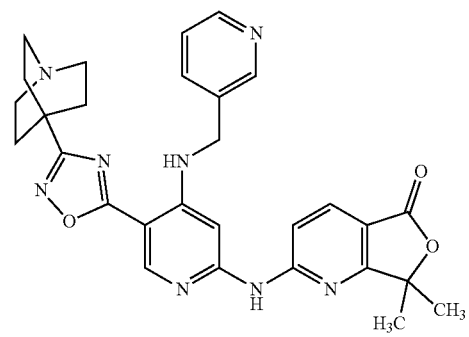

(85)

Example 85 was prepared according to the general procedure for 2-{[5-(3-{1-azabicyclo[2.2.2]octan-4-yl}-1,2,4-oxadiazol-5-yl)-4-{[(1,3-thiazol-2-yl)methyl]amino}pyridin-2-yl]amino}-7,7-dimethyl-5H,7H-furo[3,4-b]pyridin-5-one. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 min, then a 4-min hold at 100% B; Flow: 20 mL/min. Fractions containing the product were combined and dried via centrifugal evaporation to afford 2-{[5-(3-{1-azabicyclo[2.2.2]octan-4-yl}-1,2,4-oxadiazol-5-yl)-4-{[(1,3-thiazol-2-yl)methyl]amino}pyridin-2-yl]amino}-7,7-dimethyl-5H,7H-furo[3,4-b] pyridin-5-one (6.1 mg, 17% yield). HPLC $t_R$: 0.730 min; LC/MS Condition 1. ES [MS] m/z: 539.15 [M+H]$^+$. $^1$H NMR (500 MHz, DMSO-$d_6$) δ 10.59 (s, 1H), 8.73 (s, 1H), 8.65 (s, 1H), 8.52 (dd, J=4.6, 1.3 Hz, 1H), 8.45 (br t, J=5.9 Hz, 1H), 8.01 (d, J=8.4 Hz, 1H), 7.79 (br d, J=8.1 Hz, 1H), 7.68 (s, 1H), 7.64 (d, J=8.4 Hz, 1H), 7.42 (dd, J=7.7, 4.8 Hz, 1H), 4.73 (d, J=5.5 Hz, 2H), 3.01-2.90 (m, 4H), 1.90-1.83 (m, 6H), 1.46 (s, 7H), 1.26 (s, 2H).

Example 86

2-{[5-(5-cyclopropyl-1,3,4-oxadiazol-2-yl)-4-{[(1S)-2-hydroxy-1-phenylethyl]amino}pyridin-2-yl]amino}-7,7-dimethyl-5H,7H-furo[3,4-b]pyridin-5-one

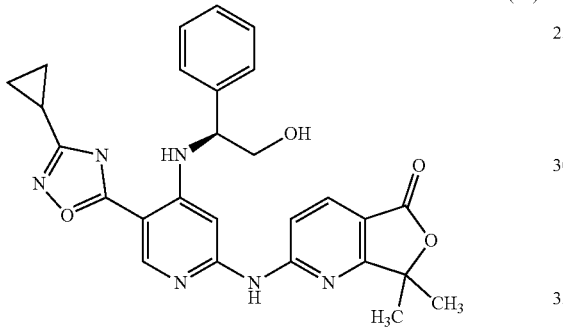

(86)

To a solution of (S)—N'-(cyclopropanecarbonyl)-6-((7,7-dimethyl-5-oxo-5,7-dihydrofuro[3,4-b]pyridin-2-yl)amino)-4-((2-hydroxy-1-phenylethyl)amino) nicotinohydrazide (50.0 mg, 0.097 mmol) in DCM (8 mL) at room temperature was added p-toluenesulfonyl chloride (36.9 mg, 0.194 mmol), followed by triethylamine (0.040 mL, 0.290 mmol). The resulting mixture was stirred at room temperature and was then concentrated to dryness, redissolved in 2 mL methanol, filtered, and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 8-48% B over 25 minutes, then a 5-minute hold at 100% B; Flow: 20 mL/min. Fractions containing the desired product were combined and dried via centrifugal evaporation to afford 2-{[5-(5-cyclopropyl-1,3,4-oxadiazol-2-yl)-4-{[(1S)-2-hydroxy-1-phenylethyl]amino}pyridin-2-yl]amino}-7,7-dimethyl-5H,7H-furo[3,4-b] pyridin-5-one (48.3 mg, 36%). HPLC $t_R$: 1.49 min; LC/MS Condition 3. ES [MS] m/z: 499.2 [M+H]$^+$. $^1$H NMR (500 MHz, DMSO-$d_6$) δ 8.75 (br d, J=6.2 Hz, 1H), 8.64 (s, 1H), 8.02 (d, J=8.8 Hz, 1H), 7.51 (d, J=8.8 Hz, 1H), 7.40-7.34 (m, 4H), 7.30-7.26 (m, 1H), 7.19 (s, 1H), 4.81-4.77 (m, 1H), 3.93 (dd, J=11.0, 4.4 Hz, 1H), 3.77 (dd, J=11.0, 5.9 Hz, 1H), 2.38-2.32 (m, 1H), 1.65 (s, 3H), 1.53 (s, 3H), 1.23 (dt, J=8.2, 2.9 Hz, 2H), 1.20-1.15 (m, 2H).

Example 87

(S)-2'-((5-(3-cyclopropyl-1,2,4-oxadiazol-5-yl)-4-((2-hydroxy-1-phenylethyl)amino) pyridin-2-yl)amino)-5'H-spiro[cyclopentane-1,7'-furo[3,4-b]pyridin]-5'-one

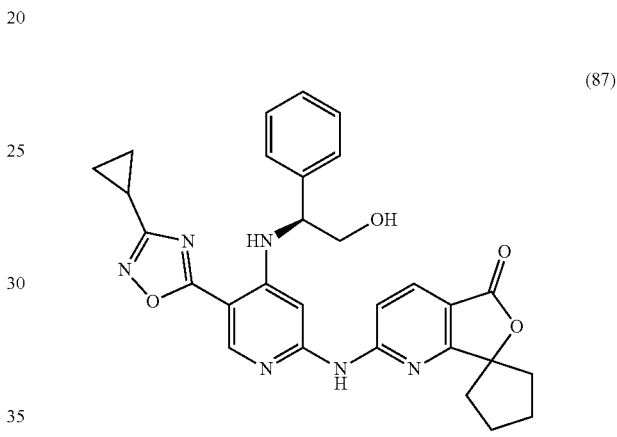

(87)

Preparation 87A:
6-amino-2-(cyclopent-1-en-1-yl)nicotinonitrile

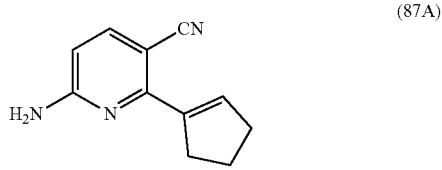 [SMILES: N#Cc1ccc(N)nc1C1=CCCC1]

(87A)

To a 40 mL pressure vial were added 6-amino-2-chloronicotinonitrile (0.20 g, 1.30 mmol), 2-(cyclopent-1-en-1-yl)-4,4,5,5-tetramethyl-1,3,2-dioxaborolane (0.329 g, 1.69 mmol), K$_2$CO$_3$ (0.270 g, 1.95 mmol), followed by 1,2-dimethoxyethane (4 mL), water (2 mL) and then Pd(PPh$_3$)$_4$ (0.030 g, 0.026 mmol). Argon was bubbled through the mixture. The reaction mixture was heated at 80° C. overnight in a heating block. The reaction mixture was cooled to room temperature, diluted with EtOAc, and washed with brine. The organic layer was separated and concentrated and the residue was purified by silica gel chromatography eluting with a gradient from 0 to 70% EtOAc in hexanes. The appropriate fractions were concentrated to afford 6-amino-2-(cyclopent-1-en-1-yl)nicotinonitrile (0.168 g, 0.91 mmol, 70% yield), as an off-white solid.

Preparation 87B: 6-amino-2-(1-hydroxycyclopentyl)nicotinonitrile

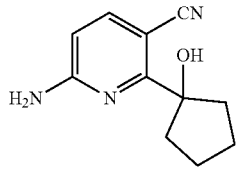
(87B)

To a round bottom flask were added 6-amino-2-(cyclopent-1-en-1-yl) nicotinonitrile (168 mg, 0.91 mmol), DCM (2 mL), 2-propanol (40 mL), phenylsilane (196 mg, 1.81 mmol), and tris(2,2,6,6-tetramethyl-3,5-heptanedionato) manganese(III) (41 mg, 0.068 mmol). The reaction mixture was cooled to 0° C. The air was removed from the flask. The reaction mixture was stirred under an atmosphere of oxygen (balloon pressure) while cooled in an ice-water bath. After 6 h, the reaction was complete and the reaction mixture was filtered through a pad of celite, and concentrated. The material was used without further purification and the yield was assumed to be theoretical.

Preparation 87C: 2'-amino-5'H-spiro[cyclopentane-1,7'-furo[3,4-b]pyridin]-5'-one

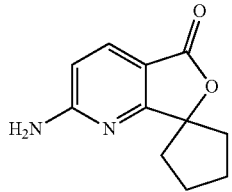
(87C)

To a round bottom flask were added 6-amino-2-(1-hydroxycyclopentyl) nicotinonitrile (0.184 g, 0.905 mmol), DMF (4 mL), water (4 mL) and NaHCO$_3$ (0.304 g, 3.62 mmol). The reaction mixture was stirred and heated to 75° C. overnight. The reaction mixture was cooled to room temperature, and diluted with 10% EtOH/EtOAc, and washed with brine. The organic layer was separated and washed with brine, dried over MgSO$_4$, filtered and concentrated. The material was purified using silica gel chromatography eluting with a gradient from 0 to 20% acetone in dichloromethane. The required fractions were combined and concentrated to afford 2'-amino-5'H-spiro[cyclopentane-1,7'-furo[3,4-b]pyridin]-5'-one (0.129 g, 0.632 mmol, 70% yield) as an off-white solid. ES [MS] m/z: 205.1 [M+H]$^+$.

Preparation 87D: Methyl (S)-4-((2-hydroxy-1-phenylethyl)amino)-6-((5'-oxo-5'H-spiro[cyclopentane-1,7'-furo[3,4-b]pyridin]-2'-yl)amino)nicotinate

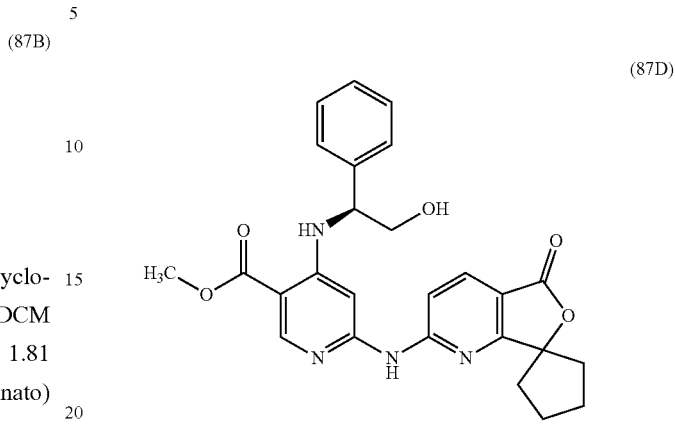
(87D)

A solution of (S)-methyl 6-chloro-4-((2-hydroxy-1-phenylethyl)amino)nicotinate (50 mg, 0.163 mmol), 2'-amino-5'H-spiro[cyclopentane-1,7'-furo[3,4-b]pyridin]-5'-one (33 mg, 0.163 mmol), Pd$_2$(dba)$_3$ (15 mg, 0.016 mmol), Xantphos (11 mg, 0.020 mmol), and potassium phosphate tribasic (104 mg, 0.489 mmol) in 1,4-dioxane (5 mL) in a pressure vessel was degassed using argon for 3 min before it was heated to 90° C. for 16 h. The reaction mixture was diluted with DCM, washed with water and brine. The organic layer was separated, dried over MgSO$_4$, filtered and concentrated. The resulting residue was purified by silica gel chromatography eluting with a gradient from 0 to 80% acetone in dichloromethane. The required fractions were concentrated to afford methyl (S)-4-((2-hydroxy-1-phenylethyl)amino)-6-((5'-oxo-5'H-spiro[cyclopentane-1,7'-furo[3,4-b]pyridin]-2'-yl) amino)nicotinate (49 mg, 0.103 mmol, 63% yield). ES [MS] m/z: 474 [M+H]$^+$. HPLC t$_R$: 1.77 min; LC/MS Condition 1.

Example 87

To a pressure-relief vial were added methyl (S)-4-((2-hydroxy-1-phenylethyl) amino)-6-((5'-oxo-5'H-spiro[cyclopentane-1,7'-furo[3,4-b]pyridin]-2'-yl)amino)nicotinate (49 mg, 0.103 mmol), (Z)—N'-hydroxycyclopropanecarboximidamide (52 mg, 0.516 mmol), sodium ethoxide (134 mg, 0.413 mmol), anhydrous ethanol (4.0 mL) and 4 Å molecular sieves (100 mg). The vial was capped and the reaction mixture was allowed to stir at 80° C. under nitrogen for 3 h. The crude reaction mixture was filtered and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the product were combined and dried via centrifugal evaporation to afford 1-{5-[6-({7,7-dimethyl-5-oxo-5H,7H-furo[3,4-b] pyridin-2-yl}amino)-4-{[(1S)-2-hydroxy-1-phenylethyl]amino}pyridin-3-yl]-1,3,4-oxadiazol-2-yl}cyclopropane-1-carbonitrile (27.7 mg, 50% yield). HPLC t$_R$: 1.78 min; LC/MS Condition 3. ES [MS] m/z: 525 [M+H]$^+$. $^1$H NMR (600 MHz, DMSO-d$_6$) δ 8.82 (br d, J=7.0 Hz, 1H), 8.67 (s, 1H), 7.97 (br d, J=8.4 Hz, 1H), 7.59 (br d, J=7.7 Hz, 1H), 7.39-7.25 (m, 6H), 5.27 (br d, J=4.4 Hz, 1H), 4.74-4.64 (m, 1H), 3.97-3.84 (m, 1H), 3.78-3.70 (m, 1H), 2.22 (br d, J=4.8 Hz, 2H), 1.98 (br s, 6H), 1.92-1.84 (m, 1H), 1.13 (br d, J=8.1 Hz, 3H).

Example 88

1-{5-[6-({7,7-dimethyl-5-oxo-5H,7H-furo[3,4-b]pyridin-2-yl}amino)-4-{[(1S)-2-hydroxy-1-phenylethyl]amino}pyridin-3-yl]-1,3,4-oxadiazol-2-yl}cyclopropane-1-carbonitrile

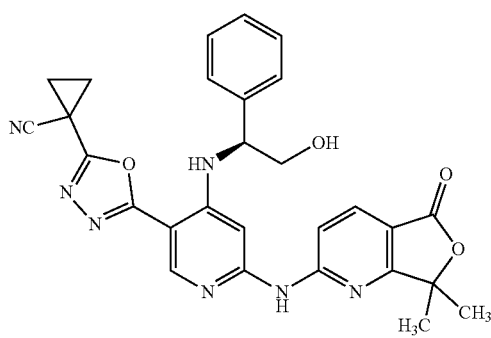

(88)

To a solution of (S)—N'-(1-cyanocyclopropanecarbonyl)-6-((7,7-dimethyl-5-oxo-5,7-dihydrofuro[3,4-b]pyridin-2-yl)amino)-4-((2-hydroxy-1-phenylethyl)amino) nicotinohydrazide (30.0 mg, 0.055 mmol) in THF (8 mL) in at room temperature was added p-tolenesulfonyl chloride (21.1 mg, 0.111 mmol), followed by triethylamine (0.023 mL, 0.166 mmol). The resulting mixture was stirred at room temperature and then heated to 55° C. for 48 h. After cooling to room temperature, the reaction mixture was concentrated to dryness, dissolved in 15 mL of a 10% solution of EtOH in EtOAc and washed with brine. The organic layer was separated and concentrated to dryness, and then redissolved in 2 mL methanol, filtered, and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 18-58% B over 23 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 8-48% B over 25 minutes, then a 5-minute hold at 100% B; Flow: 20 mL/min. Fractions containing the desired product were combined and dried via centrifugal evaporation to afford 1-{5-[6-({7,7-dimethyl-5-oxo-5H,7H-furo[3,4-b]pyridin-2-yl}amino)-4-{[(1S)-2-hydroxy-1-phenylethyl]amino}pyridin-3-yl]-1,3,4-oxadiazol-2-yl}cyclopropane-1-carbonitrile (7.2 mg, 25% yield). HPLC $t_R$: 1.46 min; LC/MS Condition 3. ES [MS] m/z: 524.2 [M+H]$^+$. $^1$H NMR (500 MHz, DMSO-d$_6$) δ 8.63 (s, 1H), 8.56 (br d, J=7.0 Hz, 1H), 8.00 (d, J=8.8 Hz, 1H), 7.54 (d, J=8.4 Hz, 1H), 7.40-7.34 (m, 4H), 7.30-7.25 (m, 2H), 7.21 (s, 1H), 7.11 (s, 1H), 7.01 (s, 1H), 4.79 (q, J=5.6 Hz, 1H), 3.93 (dd, J=11.0, 4.4 Hz, 1H), 3.77 (dd, J=10.8, 5.7 Hz, 1H), 2.12-2.07 (m, 2H), 2.05-1.99 (m, 2H), 1.64 (s, 3H), 1.50 (s, 3H).

Biological Assays

The pharmacological properties of the compounds of this invention may be confirmed by a number of biological assays. The exemplified biological assays, which follow, have been carried out with compounds of the invention.
HPK1 Inhibition Assay:

The HPK1 inhibitory potencies were determined in kinase reactions carried out in 20 mM Hepes pH 7.5, 10 mM MgCl$_2$, 0.015% Brij-15 and 2 mM DTT containing 0.625 nM HPK1 (SingalChem M23-11G), 3 µM fluorescently-labeled peptide substrate (NH$_2$-Fluorescein-RFARKGSLRQKNV-COOH, CPC Scientific), 22 µM ATP, and various concentrations of each compound. The reactions were incubated out for three hours and quenched with 1 mM EDTA solution. The reaction incubation time and enzyme concentration were optimized to obtain a maximum peptide substrate conversion of 20-30%. The reaction mixtures were analyzed by capillary electrophoresis on a Caliper LabChip EZ Reader to resolve phosphorylated and unphosphorylated peptide species and determine peptide substrate conversion. The percent inhibition was calculated from the substrate conversion generated by no enzyme control reactions for 100% inhibition and vehicle-only reactions for 0% inhibition. The compounds were dissolved in DMSO and evaluated at 11 concentrations to determine the IC$_{50}$ values.
IRAK4 Inhibition Assay:

IRAK4: 1 nM IRAK4 (160-460), 1.5 µM fluorescein labeled peptide substrate, 500 µM ATP, 6 hour incubation.

The IRAK4 inhibitory potencies were determined in kinase reactions carried out in 20 mM Hepes pH 7.5, 10 mM MgCl$_2$, 0.015% Brij-15 and 2 mM DTT containing 2 nM IRAK4 (SignalChem M24016), 1.5 µM fluorescently-labeled peptide substrate, 500 µM ATP, and various concentrations of each compound. The reactions were incubated out for three hours and quenched with 1 mM EDTA solution. The reaction incubation time and enzyme concentration were optimized to obtain a maximum peptide substrate conversion of 20-30%. The reaction mixtures were analyzed by capillary electrophoresis on a Caliper LabChip EZ Reader to resolve phosphorylated and unphosphorylated peptide species and determine peptide substrate conversion. The percent inhibition was calculated from the substrate conversion generated by no enzyme control reactions for 100% inhibition and vehicle-only reactions for 0% inhibition. The compounds were dissolved in DMSO and evaluated at 11 concentrations to determine IC$_{50}$ values.

Table A shows the HPK1 IC$_{50}$ values and the IRAK4 IC$_{50}$ values obtained from the evaluation of Examples 1-88 in the HPK1 Inhibitory assay and the IRAK4 Inhibitory assay, respectively. The ranges for the HPK1 and IRAK4 assays are: A=IC$_{50}$≤50 nM; B =IC$_{50}$>50 nM to 250 nM; C=IC$_{50}$>250 nM to 1 µM; and D=IC$_{50}$>1 µM. The ranges for the IRAK4/HPK1 Ratio are: A=<10; B=10 to 50; and C=>50.

TABLE A

| Ex. No. | HPK1 | IRAK4 | IRAK4/HPK1 Ratio |
|---|---|---|---|
| 1 | A | C | B |
| 2 | A | C | B |
| 3 | C | C | B |
| 4 | A | C | B |
| 5 | A | C | B |
| 6 | A | B | B |
| 7 | A | C | B |
| 8 | A | B | B |

TABLE A-continued

| Ex. No. | HPK1 | IRAK4 | IRAK4/HPK1 Ratio |
|---|---|---|---|
| 9 | A | C | B |
| 10 | A | C | C |
| 11 | A | C | B |
| 12 | A | C | B |
| 13 | A | C | B |
| 14 | A | B | B |
| 15 | B | C | B |
| 16 | B | C | B |
| 17 | B | C | B |
| 18 | A | B | B |
| 19 | A | C | B |
| 20 | A | C | B |
| 21 | A | C | B |
| 22 | A | C | C |
| 23 | A | C | B |
| 24 | A | C | B |
| 25 | A | C | B |
| 26 | A | C | C |
| 27 | A | B | B |
| 28 | A | C | C |
| 29 | A | C | C |
| 30 | A | C | C |
| 31 | A | B | C |
| 32 | A | C | C |
| 33 | A | B | C |
| 34 | A | C | C |
| 35 | A | C | C |
| 36 | A | C | C |
| 37 | A | C | C |
| 38 | A | B | C |
| 39 | A | C | C |
| 40 | A | C | C |
| 41 | A | B | C |
| 42 | A | C | C |
| 43 | A | C | C |
| 44 | A | C | C |
| 45 | B | C | B |
| 46 | A | B | C |
| 47 | A | C | C |
| 48 | A | C | C |
| 49 | A | C | C |
| 50 | A | C | C |
| 51 | A | C | C |
| 52 | A | C | C |
| 53 | A | C | C |
| 54 | A | B | B |
| 55 | A | A | B |
| 56 | A | C | B |
| 57 | A | C | C |
| 58 | A | C | B |
| 59 | A | C | B |
| 60 | B | C | B |
| 61 | A | B | C |
| 62 | A | C | C |
| 63 | A | B | B |
| 64 | B | C | B |
| 65 | A | C | B |
| 66 | B | C | B |
| 67 | A | B | B |
| 68 | A | C | B |
| 69 | A | B | B |
| 70 | B | C | B |
| 71 | A | C | B |
| 72 | B | C | B |
| 73 | B | C | B |
| 74 | B | C | B |
| 75 | B | C | B |
| 76 | B | C | B |
| 77 | A | C | C |
| 78 | B | C | B |
| 79 | B | C | B |
| 80 | A | B | C |
| 81 | A | B | C |
| 82 | A | B | C |
| 83 | A | B | C |
| 84 | A | C | C |
| 85 | A | C | C |
| 86 | A | B | B |
| 87 | A | B | B |
| 88 | A | C | C |

HPK1 target inhibition in T cells can assist in T cell stimulation, whereas off-target IRAK4 inhibition can result in T cell suppression. Thus, selectivity for HPK1 inhibition over IRAK4 inhibition is advantageous for achieving sufficient T cell activation.

In Table A, a larger value for the ratio of the IRAK4 $IC_{50}$ value to the HPK1 $IC_{50}$ value indicates greater selectivity for the inhibition of the HPK1 activity over the inhibition of the IRAK4 activity.

The compounds of the present invention, as exemplified by Examples 1 to 88, show the surprising advantage as inhibitors of HPK1 with selectivity over IRAK4 inhibition. The exemplified compounds of the invention reported in Table A had selectivity ratios for the inhibition of HPK1 over IRAK4 of at least 10 times or greater.

The compounds of the present invention possess activity as inhibitors of HPK1 and are selective over IRAK4, and thus may be used in treating, preventing, or curing conditions that benefit from by T cell stimulation, such as the treatment of viral infections and proliferative disorders, such as cancer.

Antitumor Immune Responses in HKP1 Kinase-Dead Mice

An HPK1 kinase-dead mouse (HPK1 KD) was generated and extensively characterized using syngeneic tumor models and ex vivo studies.

HPK1 KD mice with a K46M mutation were generated and characterized via immune cell phenotyping in peripheral blood and secondary lymphoid organs by fluorescence-activated cell sorting (FACS) analysis. T-cell proliferation (via $^3$H-thymidine incorporation) and cytokine secretion (interleukin-2 [IL-2] and interferon-gamma [IFN-γ]) were evaluated in splenocytes (total, CD8+, and CD4+) from mice stimulated in vitro with anti-CD3 and anti-CD28 monoclonal antibodies (mAbs). HPK1 wild-type (WT) and KD mice were further interrogated in syngeneic 1956 mouse sarcoma and MC38 colon adenocarcinoma models to determine if HPK1 deficiency enhances immune responses. Antitumor activity was monitored in both models; in the colon adenocarcinoma model, mice were treated with anti-PD-1 mAb or a control isotype-matched mAb. Immune phenotyping in draining lymph nodes, tumor tissues and ex vivo studies (re-stimulation and cytolytic activity) were performed in the sarcoma model.

The results indicated the following:
- The levels of white blood cells and proportions of different immune cell types were similar in HPKT WT and KD mice;
- T-cell proliferation and secretion of IL-2 and IFN-γ were increased in HPK1 KD compared with WT mice;
- Antitumor efficacy observed with anti-PD-1 treatment was enhanced in the HPK1 KD colon adenocarcinoma model (FIG. 1);
- Antitumor efficacy was greater in HPK1 KD vs WT mice in a sarcoma model;
- T-cell activation (CD8$^+$ and CD4$^+$) and cytolytic activity against syngeneic sarcoma tumor cells were augmented in HPK1 KD mice; and
- Antitumor immune cell phenotype signatures were enhanced in the tumor microenvironment and draining lymph nodes of HPK1 KD mice. In particular, in the tumor, the ratio of CD8+ T cells/CD4+FOXP3+ Treg cells was enhanced by about 2 fold. In the tumor draining lymph nodes, the percentage of CD45+FoxP3+ T cells (Treg cells) of CD45+ LIVE single cells was lower in the HPK1 KD mice relative to the WT mice; the percentage of CD8+Ki67+ cells of CD45+ LIVE single cells is at least 2 fold higher in the HPK1 KD mice relative to the WT mice; and the percentage of CD4+Ki67+ of CD45+ LIVE single cells is higher in the HPK1 KD mice relative to the WT mice.

The results indicated that HPK1 KD mice were grossly normal, and immune phenotyping revealed no difference in the proportion of peripheral immune cells compared with WT mice. HPK1 inactivation resulted in greater CD4+ and CD8+ T cell proliferation and secretion of IL-2 and IFN-γ. Cytolytic activities against syngeneic tumor cells were augmented in HPK1 KD CD8+ T cells. HPK1 KD mice demonstrated increased antitumor efficacy in a sarcoma model, along with improved immune cell phenotypic signatures in the tumor microenvironment and tumor-draining lymph nodes.

These data showed that genetic inactivation of HPK1 enhances immune responses and improves antitumor efficacy, indicating an important role of HPK1 in mediating antitumor immune responses. The data is consistent with the use of an HPK1 inhibitor in combination with a PD-1 inhibitor.

---

SEQUENCE LISTING

<160> NUMBER OF SEQ ID NOS: 1

<210> SEQ ID NO 1
<211> LENGTH: 19
<212> TYPE: PRT
<213> ORGANISM: Homo sapiens

<400> SEQUENCE: 1

Asn His Phe Leu Arg Phe Ala Arg Lys Gly Ser Leu Arg Gln Lys Asn
1               5                   10                  15

Val Cys His

--- zolyl, triazolyl, isoxazolyl, and dihydrooxazolyl, each substituted with zero to 2 $R_{1c}$;

$R_{1a}$ is $C_{1-4}$ alkyl, $C_{1-3}$ fluoroalkyl, $C_{1-2}$ cyanoalkyl, —$CH_2CH_2OCH_3$, —$CH_2C\equiv CH$, —$(CH_2)_{2-3}N(CH_3)_2$, —$CH(CH_3)$(phenyl), or —$(CH_2)_mR_a$;

$R_a$ is $C_{3-7}$ cycloalkyl, $C_{5-8}$ bicycloalkyl, 4- to 7-membered heterocyclyl, 5- to 8-membered bicyclic nitrogen containing heterocyclyl, phenyl, or 5- to 6-membered heteroaryl, each substituted with zero to 4 $R_x$;

each $R_x$ is independently selected from F, Cl, —CN, —OH, $C_{1-3}$ alkyl, —$CD_3$, —$CF_3$, —$OCH_3$, —$CH_2$(morpholinyl), phenyl, and benzyl;

m is zero, 1, 2, 3, 4, or 5;

$R_{1b}$ is —$C(CH_3)_2OH$, —$C(CF_3)(CH_3)OH$, cyclopropyl, pyridinyl, or pyrazinyl;

each $R_{1c}$ is independently F, $C_{1-4}$ alkyl, $C_2$-6 hydroxyalkyl, $C_{1-4}$ fluoroalkyl, $C_2$-4 hydroxy-fluoroalkyl, —$(CH_2)_nR_c$, =O, —$S(C_{1-2}$ alkyl), azetidinyl, morpholinyl, piperidinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, (methoxycarbonyl)aminobicyclo[1.1.1]pentanyl, or $C_3$-6 cycloalkyl substituted with zero to 2 substituents independently selected from F, —CN, —$CF_3$, —$CH_2OH$, and —OC(O)(difluorazetidinyl);

$R_c$ is 4- to 7-membered heterocyclyl or 5- to 8-membered bicyclic nitrogen containing heterocyclyl, each substituted with zero to 4 $R_x$;

n is zero, 1, 2, 3, 4, or 5;

$R_2$ is:

(i) $C_{1-6}$ alkyl substituted with zero to 6 substituents independently selected from F, Cl, —CN, —OH, $C_{1-3}$ alkoxy, $C_{1-3}$ fluoroalkoxy, $C_{3-6}$ cycloalkyl, and —$NR_yR_y$;

(ii) —$CHR_{2a}R_{2b}$, —$(CH_2)_{1-3}NR_y(CH_2)_{1-3}NR_yR_y$, —$(CR_yR_y)_{1-2}NR_yC(O)OCH_2$(phenyl), —$CHR_{2b}CH_2R_{2a}$, or —$CH_2CH_2C(O)R_{2a}$; or (iii) a cyclic group selected from cyclopropyl, indazolyl, phenyl, piperidinyl, pyrazolyl, oxetanyl, and tetrahydropyrido[3,4-d]pyrimidinyl, each substituted with zero to 1 substituent selected from —CN, —$CH_3$, —$SCH_3$, pyrimidinyl, and phenyl;

$R_{2a}$ is $C_{3-6}$ cycloalkyl, oxadiazolyl, oxazolyl, oxetanyl, phenyl, pyrazolyl, pyrazolo[1,5-a]pyridinyl, pyridazinyl, pyridinyl, pyrimidinyl, pyrrolidinyl, tetrahydropyrido[3,4-d]pyrimidinyl, or thiazolyl, each substituted with zero to 2 R2e;

---

The invention claimed is:

1. A compound of Formula (I):

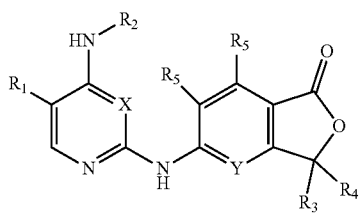

(I)

or a salt thereof, wherein:

X is CH or N;

Y is $CR_5$ or N;

$R_1$ is —C(O)OH, —C(O)O($C_{1-3}$ alkyl), —C(O)$NHR_{1a}$, —NHC(O)$R_{1a}$, —C(O)$NHNH_2$, —C(O)NHNHC(O)$R_{1b}$, —C(O)NHNHC(=N$CH_2CH_3$($NH(CH_2)_{2-4}N$($CH_3)_2$), 1,8-dioxa-3-azaspiro[4.5]decenyl, or a cyclic group selected from oxadiazolyl, thiazolyl, oxazolyl, pyridinyl, pyrimidinyl, thiadiazolyl, pyrazinyl, imida-

127

$R_{2b}$ is H, —OH, $C_{1-3}$ alkyl, $C_{1-2}$ fluoroalkyl, $C_{1-3}$ hydroxyalkyl, —CH$_2$OCH$_3$, —CH$_2$OCF$_3$, —CH$_2$NR$_y$R$_y$, —CH$_2$S(C$_{1-2}$ alkyl), or —CH$_2$N$_3$;

each $R_{2c}$ is independently F, Cl, —CN, —OH, $C_{1-2}$ alkyl, $C_{1-3}$ hydroxyalkyl, $C_{1-2}$ aminoalkyl, $C_{1-2}$ alkoxy, $C_{1-2}$ fluoroalkoxy, —CH$_2$O(C$_{1-2}$ alkyl), —NR$_y$C(O)(C$_{1-2}$ alkyl), —S(C$_{1-2}$ alkyl), —S(O)$_2$(C$_{1-4}$ alkyl), phenyl, methyloxiranyl, or pyrimidinyl;

each $R_y$ is independently H or —CH$_3$;

$R_3$ is H or —CH$_3$;

$R_4$ is H or —CH$_3$;

or $R_3$ and $R_4$ together with the carbon atom to which they are attached form a $C_{4-6}$ cycloalkyl ring; and each $R_5$ is independently H or halo.

2. The compound according to claim 1 or a salt thereof, wherein:

R2 is:
(i) $C_{1-6}$ alkyl substituted with zero to 6 substituents independently selected from F, —OH, $C_{1-3}$ alkoxy, $C_{1-3}$ fluoroalkoxy, $C_{3-6}$ cycloalkyl, and —NR$_y$R$_y$;
(ii) —CHR$_{2a}$R$_{2b}$; or
(iii) a cyclic group selected from cyclopropyl, indazolyl, phenyl, piperidinyl, and pyrazolyl, each substituted with zero to 1 substituent selected from —CN and —CH$_3$.

3. The compound according to claim 1 or a salt thereof, wherein:

$R_1$ is —C(O)OH, —C(O)O(C$_{1-3}$ alkyl), —C(O)NHR$_{1a}$, —C(O)NHNH$_2$, —C(O)NHNHC(O)R$_{1b}$, —C(O)NHNHC(=NCH$_2$CH$_3$(NH(CH$_2$)$_{2-4}$N(CH$_3$)$_2$), 1,8-dioxa-3-azaspiro[4.5]dec-2-enyl, or a cyclic group selected from oxadiazolyl and pyrimidinyl, each substituted with zero to 2 $R_{1c}$;

$R_{1a}$ is $C_{2-4}$ alkyl, —CH$_2$CH$_2$OCH$_3$, —CH$_2$C≡CH, —(CH$_2$)$_{2-3}$N(CH$_3$)$_2$, —CH(CH$_3$)(phenyl), pyrrolidinyl substituted with benzyl, —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with —CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —CH$_2$CH$_2$CH$_2$(imidazolyl), —NHC(O)(cyclopropyl), —NHC(O)(pyrazinyl), —NHC(O)(pyridinyl), or cyclopropyl substituted with phenyl;

each $R_{1c}$ is independently $C_{1-4}$ alkyl, —C(CH$_3$)$_2$H, —C(CH$_3$)$_2$CH$_2$CH$_2$CH$_2$OH, —C(CF$_3$)(CH$_3$)OH, =O, —CH$_2$(morpholinyl), cyclopropyl, trifluoromethylcyclopropyl, cyanocyclopropyl, hydroxymethylcyclopropyl, cyclopropyl substituted with —OC(O)(difluorazetidinyl), difluorocyclobutyl, azetidinyl, morpholinyl, piperidinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, or (methoxycarbonyl)aminobicyclo[1.1.1]pentanyl;

$R_2$ is —CH$_2$C(CH$_3$)$_2$CH$_2$NH$_2$, —CH$_2$CH$_2$C(CH$_3$)$_2$NH$_2$, —CH$_2$(thiazolyl), —CH$_2$(pyridinyl), —CH(cyclopropyl)CH$_2$OH, —CH(phenyl)CH$_2$OH, —CH(fluorophenyl)CH$_2$OH, —CH$_2$(hydroxypropylphenyl), or indazoly; and each $R_5$ is H.

4. The compound according to claim 1 or a salt thereof, wherein X is N; and Y is CH.

5. The compound according to claim 4 or a salt thereof, wherein:

128

$R_{1a}$ is $C_{2-4}$ alkyl, —CH$_2$CH$_2$OCH$_3$, —CH$_2$C≡CH, —(CH$_2$)$_{2-3}$N(CH$_3$)$_2$, —CH(CH$_3$)(phenyl), pyrrolidinyl substituted with benzyl, —CH$_2$(azabicyclo[2.2.2]octanyl), —CH$_2$(hydroxyazabicyclo[2.2.2]octanyl), —CH$_2$(difluorocyclobutyl), —CH$_2$(cyclopropyl substituted with —CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —CH$_2$CH$_2$CH$_2$(imidazolyl), —NHC(O)(cyclopropyl), —NHC(O)(pyrazinyl), —NHC(O)(pyridinyl), or cyclopropyl substituted with phenyl;

$R_{1c}$ is $C_{1-4}$ alkyl, —C(CH$_3$)$_2$OH, —C(CH$_3$)$_2$CH$_2$CH$_2$CH$_2$OH, —C(CF$_3$)(CH$_3$)OH, =O, —CH$_2$(morpholinyl), difluorocyclobutyl, morpholinyl, tetrahydropyranyl, dioxotetrahydrothiopyranyl, fluorophenyl, pyridinyl, pyridazinyl, azabicyclo[2.2.2]octanyl, aminobicyclo[1.1.1]pentanyl, dimethylaminobicyclo[1.1.1]pentanyl, acetamidobicyclo[1.1.1]pentanyl, (methoxycarbonyl)aminobicyclo[1.1.1]pentanyl, cyclopropyl, trifluoromethylcyclopropyl, hydroxymethylcyclopropyl, or cyclopropyl substituted with —OC(O)(difluorazetidinyl);

$R_2$ is —CH$_2$CH$_2$C(CH$_3$)$_2$NH$_2$, —CH$_2$C(CH$_3$)$_2$CH$_2$NH$_2$, —CH(phenyl)CH$_2$OH, —CH$_2$(hydroxypropylphenyl), or indazolyl;

$R_3$ is —CH$_3$;

$R_4$ is —CH$_3$; and each $R_5$ is H.

6. The compound according to claim 1 wherein X is CH.

7. The compound according to claim 6 or a salt thereof, wherein $R_1$ is oxadiazolyl substituted with $R_{1c}$;

$R_{1c}$ is cyclopropyl, cyanocyclopropyl, azabicyclo[2.2.2]octanyl, or fluoroazabicyclo[2.2.2]octanyl;

$R_2$ is —CH(cyclopropyl)CH$_2$OH, —CH(phenyl)CH$_2$OH, —CH(fluorophenyl)CH$_2$OH, —CH$_2$(thiazolyl), or —CH$_2$(pyridinyl);

$R_3$ is —CH$_3$;

$R_4$ is —CH$_3$;

or $R_3$ and $R_4$ together with the carbon atom to which they are attached form a cyclopentyl ring; and each $R_5$ is H.

8. The compound according to claim 1 or a salt thereof, wherein:

$R_1$ is —C(O)OH, —C(O)O(C$_{1-3}$ alkyl), —C(O)NHR$_{1a}$, —C(O)NHNH$_2$, —C(O)NHNHC(O)R$_{1b}$, —C(O)NHNHC(=NCH$_2$CH$_3$(NH(CH$_2$)$_{2-4}$N(CH$_3$)$_2$), 1,8-dioxa-3-azaspiro[4.5]dec-2-enyl, or a cyclic group selected from oxadiazolyl and pyrimidinyl, each substituted with zero to 2 $R_{1c}$;

$R_{1a}$ is cyclopropyl substituted with phenyl, pyrrolidinyl substituted with —CH$_2$(phenyl), —CH(CH$_3$)(phenyl), —CH$_2$(azabicyclo[2.2.2]octanyl), —CH$_2$(difluorocyclobutyl), —CH$_2$(hydroxyazabicyclo[2.2.2]octanyl), —CH$_2$(cyclopropyl substituted with CH$_2$(morpholinyl)), —CH$_2$(methyloxetanyl), —CH$_2$(phenyl), —CH$_2$(methylphenyl), —CH$_2$(methylpyrazinyl), —CH$_2$(pyridinyl), —CH$_2$CH$_2$CH$_2$(morpholinyl), —NHC(O)(cyclopropyl), —NHC(O)(pyrazinyl), or —NHC(O)(pyridinyl);

$R_{1b}$ is —C(CH$_3$)$_2$OH, —C(CF$_3$)(CH$_3$)OH, cyclopropyl, pyridinyl, or pyrazinyl;

each $R_{1c}$ is independently $C_{1-4}$ alkyl, —C(CH$_3$)$_2$OH, —C(CH$_3$)$_2$CH$_2$CH$_2$CH$_2$OH, —C(CF$_3$)(CH$_3$)OH, =O, —CH$_2$(morpholinyl), cyclopropyl, trifluoromethylcyclopropyl, cyanocyclopropyl, hydroxymethylcyclopropyl, cyclopropyl substituted with —OC(O)(difluorazetidinyl), difluorocyclobutyl, morpholinyl, tetrahydropyranyl, dioxotetrahydrothiopyranyl, fluorophenyl, pyridinyl, pyridazinyl, azabicyclo[2.2.2]octanyl, fluoroazabicyclo[2.2.2]octanyl, aminobicyclo[1.1.1]pentanyl, dimethylaminobicyclo[1.1.1]pentanyl, acetamidobicyclo[1.1.1]pentanyl, or (methoxycarbonyl)aminobicyclo[1.1.1]pentanyl; and $R_2$ is —CH$_2$C(CH$_3$)$_2$CH$_2$NH$_2$, —CH$_2$CH$_2$C(CH$_3$)$_2$NH$_2$, —CH$_2$(thiazolyl), —CH$_2$(pyridinyl), —CH(cyclopropyl)CH$_2$OH, —CH(phenyl)CH$_2$OH, —CH(fluorophenyl)CH$_2$OH, —CH$_2$(hydroxypropylphenyl), or indazolyl; and each $R_5$ is H.

9. A pharmaceutical composition comprising a compound according to claim 1 or a pharmaceutically-acceptable salt thereof; and a pharmaceutically acceptable carrier.

10. A method of treating a disease or disorder, comprising administering to a mammalian patient a compound of claim 1 or a pharmaceutically acceptable salt thereof, wherein said disease or disorder is cancer or viral infection and wherein treating a disease or disorder is inhibiting and/or relieving the disease or disorder.

11. A method of claim 10, wherein said cancer is selected from cancer of the colon, pancreatic cancer, breast cancer, prostate cancer, lung cancer, ovarian cancer, cervical cancer, renal cancer, cancer of the head and neck, lymphoma, leukemia, and melanoma.

12. The method according to claim 10 further comprising administering to the patient a therapeutically effective amount of an anti-viral agent, a chemotherapeutic agent, radiation, an anti-tumor vaccine, an antiviral vaccine, cytokine therapy and/or a tyrosine kinase inhibitor prior to, simultaneously with or after administration of said compound.

13. A method of inhibiting activity of hematopoietic progenitor kinase 1 (HPK1) comprising contacting said hematopoietic progenitor kinase 1 with a compound according to claim 1, or a pharmaceutically acceptable salt thereof.

14. The compound according to claim 1 or a salt thereof, wherein said compound is:

5-[(4'-{[(1S)-2-hydroxy-1-phenylethyl]amino}-[2,5'-bipyrimidine]-2'-yl)amino]-1,3-dihydro-2-benzofuran-1-one (1);

ethyl 2-[(3,3-dimethyl-1-oxo-1,3-dihydro-2-benzofuran-5-yl)amino]-4-{[(1S)-2-hydroxy-1-phenylethyl] amino}pyrimidine-5-carboxylate (2);

2-[(3,3-dimethyl-1-oxo-1,3-dihydro-2-benzofuran-5-yl) amino]-4-{[(1S)-2-hydroxy-1-phenylethyl] amino}pyrimidine-5-carboxylic acid (3);

N-[(3,3-difluorocyclobutyl) methyl]-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide (4);

2-[(3,3-dimethyl-1-oxo-1,3-dihydro-2-benzofuran-5-yl) amino]-N-[3-(dimethylamino) propyl]-4-{[(1S)-2-hydroxy-1-phenylethyl]amino}pyrimidine-5-carboxamide (5);

2-[(3,3-dimethyl-1-oxo-1,3-dihydro-2-benzofuran-5-yl) amino]-4-{[(1S)-2-hydroxy-1-phenylethyl]amino}-N-[(pyridin-2-yl)methyl]pyrimidine-5-carboxamide (6);

2-[(3,3-dimethyl-1-oxo-1,3-dihydro-2-benzofuran-5-yl) amino]-4-{[(1S)-2-hydroxy-1-phenylethyl]amino}-N-[3-(morpholin-4-yl)propyl]pyrimidine-5-carboxamide (7);

2-[(3,3-dimethyl-1-oxo-1,3-dihydro-2-benzofuran-5-yl) amino]-4-{[(1S)-2-hydroxy-1-phenylethyl]amino}-N-(2-methoxyethyl)pyrimidine-5-carboxamide (8);

2-[(3,3-dimethyl-1-oxo-1,3-dihydro-2-benzofuran-5-yl) amino]-N-[2-(dimethylamino)ethyl]-4-{[(1S)-2-hydroxy-1-phenylethyl] amino}pyrimidine-5-carboxamide (9);

N-benzyl-2-[(3,3-dimethyl-1-oxo-1,3-dihydro-2-benzofuran-5-yl)amino]-4-{[(1S)-2-hydroxy-1-phenylethyl] amino}pyrimidine-5-carboxamide (10);

N-tert-butyl-2-[(3,3-dimethyl-1-oxo-1,3-dihydro-2-benzofuran-5-yl) amino]-4-{[(1S)-2-hydroxy-1-phenylethyl]amino}pyrimidine-5-carboxamide (11);

2-[(3,3-dimethyl-1-oxo-1,3-dihydro-2-benzofuran-5-yl) amino]-4-{[(1S)-2-hydroxy-1-phenylethyl]amino}-N-(2-methylpropyl)pyrimidine-5-carboxamide (12);

2-[(3,3-dimethyl-1-oxo-1,3-dihydro-2-benzofuran-5-yl) amino]-4-{[(1S)-2-hydroxy-1-phenylethyl]amino}-N-(propan-2-yl)pyrimidine-5-carboxamide (13);

2-[(3,3-dimethyl-1-oxo-1,3-dihydro-2-benzofuran-5-yl) amino]-4-{[(1S)-2-hydroxy-1-phenylethyl]amino}-N-propylpyrimidine-5-carboxamide (14);

2-[(3,3-dimethyl-1-oxo-1,3-dihydro-2-benzofuran-5-yl) amino]-4-{[(1S)-2-hydroxy-1-phenylethyl]amino}-N-(1-phenylethyl) pyrimidine-5-carboxamide (15);

2-[(3,3-dimethyl-1-oxo-1,3-dihydro-2-benzofuran-5-yl) amino]-4-{[(1S)-2-hydroxy-1-phenylethyl]amino}-N-[(2-methylphenyl)methyl] pyrimidine-5-carboxamide (16);

2-[(3,3-dimethyl-1-oxo-1,3-dihydro-2-benzofuran-5-yl) amino]-4-{[(1S)-2-hydroxy-1-phenylethyl]amino}-N-[(1S,2R)-2-phenylcyclopropyl] pyrimidine-5-carboxamide (17);

2-[(3,3-dimethyl-1-oxo-1,3-dihydro-2-benzofuran-5-yl) amino]-N-ethyl-4-{[(1S)-2-hydroxy-1-phenylethyl] amino}pyrimidine-5-carboxamide (18);

2-[(3,3-dimethyl-1-oxo-1,3-dihydro-2-benzofuran-5-yl) amino]-4-{[(1S)-2-hydroxy-1-phenylethyl]amino}-N-[3-(1H-imidazol-1-yl)propyl]pyrimidine-5-carboxamide (19);

2-[(3,3-dimethyl-1-oxo-1,3-dihydro-2-benzofuran-5-yl) amino]-4-{[(1S)-2-hydroxy-1-phenylethyl]amino}-N-[(5-methylpyrazin-2-yl)methyl]pyrimidine-5-carboxamide (20);

2-[(3,3-dimethyl-1-oxo-1,3-dihydro-2-benzofuran-5-yl) amino]-4-{[(1S)-2-hydroxy-1-phenylethyl]amino}-N-(prop-2-yn-1-yl)pyrimidine-5-carboxamide (21);

N-(1-benzylpyrrolidin-3-yl)-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (22);

2-[(3,3-dimethyl-1-oxo-1,3-dihydro-2-benzofuran-5-yl) amino]-4-{[(1S)-2-hydroxy-1-phenylethyl]amino}-N-[(3-methyloxetan-3-yl)methyl]pyrimidine-5-carboxamide (23);

2-[(3,3-dimethyl-1-oxo-1,3-dihydro-2-benzofuran-5-yl) amino]-N-{[(3R)-3-hydroxy-1-azabicyclo[2.2.2]octan-3-yl]methyl}-4-{[(1S)-2-hydroxy-1-phenylethyl] amino} pyrimidine-5-carboxamide (24);

N-({1-azabicyclo[2.2.2]octan-3-yl}methyl)-2-[(3,3-dimethyl-1-oxo-1,3-dihydro-2-benzofuran-5-yl)amino]-4-{[(1S)-2-hydroxy-1-phenylethyl]amino}pyrimidine-5-carboxamide (25);

2-[(3,3-dimethyl-1-oxo-1,3-dihydro-2-benzofuran-5-yl) amino]-4-{[(1S)-2-hydroxy-1-phenylethyl]amino}-N-({1-[(morpholin-4-yl)methyl]cyclopropyl}methyl)pyrimidine-5-carboxamide (26);

5-[(5-{1,8-dioxa-3-azaspiro[4.5]dec-2-en-2-yl}-4-{[(1S)-2-hydroxy-1-phenylethyl]amino}pyrimidin-2-yl)amino]-3,3-dimethyl-1,3-dihydro-2-benzofuran-1-one (27);

5-[(4-{[(1S)-2-hydroxy-1-phenylethyl]amino}-5-(3-methyl-1,2,4-oxadiazol-5-yl)pyrimidin-2-yl)amino]-3,3-dimethyl-1,3-dihydro-2-benzofuran-1-one (28);

5-{[5-(3-ethyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (29);

5-{[5-(3-cyclopropyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (30);

5-[(4-{[(1S)-2-hydroxy-1-phenylethyl]amino}-5-[3-(morpholin-4-yl)-1,2,4-oxadiazol-5-yl]pyrimidin-2-yl)amino]-3,3-dimethyl-1,3-dihydro-2-benzofuran-1-one (31);

5-[(4-{[(1S)-2-hydroxy-1-phenylethyl]amino}-5-{3-[(morpholin-4-yl)methyl]-1,2,4-oxadiazol-5-yl}pyrimidin-2-yl)amino]-3,3-dimethyl-1,3-dihydro-2-benzofuran-1-one (32);

5-[(4-{[(1S)-2-hydroxy-1-phenylethyl]amino}-5-[3-(oxan-4-yl)-1,2,4-oxadiazol-5-yl]pyrimidin-2-yl)amino]-3,3-dimethyl-1,3-dihydro-2-benzofuran-1-one (33);

5-[(4-{[(1S)-2-hydroxy-1-phenylethyl]amino}-5-[3-(propan-2-yl)-1,2,4-oxadiazol-5-yl]pyrimidin-2-yl)amino]-3,3-dimethyl-1,3-dihydro-2-benzofuran-1-one (34);

5-[(4-{[(1S)-2-hydroxy-1-phenylethyl]amino}-5-(3-propyl-1,2,4-oxadiazol-5-yl)pyrimidin-2-yl)amino]-3,3-dimethyl-1,3-dihydro-2-benzofuran-1-one (35);

5-{[5-(3-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (36);

5-[(4-{[(1S)-2-hydroxy-1-phenylethyl]amino}-5-[3-(6-hydroxy-2-methylhexan-2-yl)-1,2,4-oxadiazol-5-yl]pyrimidin-2-yl)amino]-3,3-dimethyl-1,3-dihydro-2-benzofuran-1-one (37);

5-[(4-{[(1S)-2-hydroxy-1-phenylethyl]amino}-5-{3-[1-(hydroxymethyl)cyclopropyl]-1,2,4-oxadiazol-5-yl}pyrimidin-2-yl)amino]-3,3-dimethyl-1,3-dihydro-2-benzofuran-1-one (38);

5-{[5-(3-tert-butyl-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (39);

5-({5-[3-(3,3-difluorocyclobutyl)-1,2,4-oxadiazol-5-yl]-4-{[(1S)-2-hydroxy-1-phenylethyl]amino} pyrimidin-2-yl}amino)-3,3-dimethyl-1,3-dihydro-2-benzofuran-1-one (40);

(S)-5-((4-((2-hydroxy-1-phenylethyl)amino)-5-(3-(1-hydroxy-2-methylpropan-2-yl)-1,2,4-oxadiazol-5-yl)pyrimidin-2-yl)amino)-3,3-dimethylisobenzofuran-1(3H)-one (41);

5-[(4-{[(1S)-2-hydroxy-1-phenylethyl]amino}-5-[3-(pyridin-2-yl)-1,2,4-oxadiazol-5-yl]pyrimidin-2-yl)amino]-3,3-dimethyl-1,3-dihydro-2-benzofuran-1-one (42);

5-[(4-{[(1S)-2-hydroxy-1-phenylethyl]amino}-5-[3-(pyridin-3-yl)-1,2,4-oxadiazol-5-yl]pyrimidin-2-yl)amino]-3,3-dimethyl-1,3-dihydro-2-benzofuran-1-one (43);

5-({5-[3-(4-fluorophenyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one (44);

5-({5-[3-(3-fluorophenyl)-1,2,4-oxadiazol-5-yl]-4-{[(1S)-2-hydroxy-1-phenylethyl]amino}pyrimidin-2-yl}amino)-3,3-dimethyl-1,3-dihydro-2-benzofuran-1-one (45);

5-{[5-(3-{3-aminobicyclo[1.1.1]pentan-1-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (47);

5-[(5-{3-[3-(dimethylamino) bicyclo[1.1.1]pentan-1-yl]-1,2,4-oxadiazol-5-yl}-4-{[(1S)-2-hydroxy-1-phenylethyl]amino}pyrimidin-2-yl)amino]-3,3-dimethyl-1,3-dihydro-2-benzofuran-1-one (48);

N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl)bicyclo[1.1.1]pentan-1-yl]acetamide (49);

methyl N-[3-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,2,4-oxadiazol-3-yl)bicyclo[1.1.1]pentan-1-yl]carbamate (50);

2-[(3,3-dimethyl-1-oxo-1,3-dihydro-2-benzofuran-5-yl)amino]-4-{[(1S)-2-hydroxy-1-phenylethyl]amino}pyrimidine-5-carbohydrazide (51);

5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-2,3-dihydro-1,3,4-oxadiazol-2-one (52);

5-{2-[(3,3-dimethyl-1-oxo-1,3-dihydro-2-benzofuran-5-yl) amino]-4-{[(1S)-2-hydroxy-1-phenylethyl]amino}pyrimidin-5-yl}-3-ethyl-2,3-dihydro-1,3,4-oxadiazol-2-one (53);

5-[(4-{[(1S)-2-hydroxy-1-phenylethyl]amino}-5-(1,3,4-oxadiazol-2-yl) pyrimidin-2-yl) amino]-3,3-dimethyl-1,3-dihydro-2-benzofuran-1-one (54);

5-[(4-{[(1S)-2-hydroxy-1-phenylethyl]amino}-5-(5-methyl-1,3,4-oxadiazol-2-yl) pyrimidin-2-yl) amino]-3,3-dimethyl-1,3-dihydro-2-benzofuran-1-one (55);

N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyridine-3-carbohydrazide (56);

5-[(4-{[(1S)-2-hydroxy-1-phenylethyl]amino}-5-[5-(pyridin-3-yl)-1,3,4-oxadiazol-2-yl]pyrimidin-2-yl)amino]-3,3-dimethyl-1,3-dihydro-2-benzofuran-1-one (57);

N'-{2-[(3,3-dimethyl-1-oxo-1,3-dihydro-2-benzofuran-5-yl)amino]-4-{[(1S)-2-hydroxy-1-phenylethyl]amino}pyrimidine-5-carbonyl}pyrazine-2-carbohydrazide (58);

1-({2-[(3,3-dimethyl-1-oxo-1,3-dihydro-2-benzofuran-5-yl)amino]-4-{[(1S)-2-hydroxy-1-phenylethyl]amino}pyrimidin-5-yl} formohydrazido)-N-[3-(dimethylamino)propyl]-N'-ethylmethanimidamide (59);

2-[(3,3-dimethyl-1-oxo-1,3-dihydro-2-benzofuran-5-yl)amino]-4-{[(1S)-2-hydroxy-1-phenylethyl]amino}-N'-(2-hydroxy-2-methylpropanoyl)pyrimidine-5-carbohydrazide (60);

5-[(4-{[(1S)-2-hydroxy-1-phenylethyl]amino}-5-[5-(2-hydroxypropan-2-yl)-1,3,4-oxadiazol-2-yl]pyrimidin-2-yl)amino]-3,3-dimethyl-1,3-dihydro-2-benzofuran-1-one (61);

(S)—N'-(cyclopropanecarbonyl)-2-((3,3-dimethyl-1-oxo-1,3-dihydroisobenzofuran-5-yl) amino)-4-((2-hydroxy-1-phenylethyl)amino)pyrimidine-5-carbohydrazide (62);

5-{[5-(5-cyclopropyl-1,3,4-oxadiazol-2-yl)-4-{[(1S)-2-hydroxy-1-phenylethyl]amino}pyrimidin-2-yl]amino}-3,3-dimethyl-1,3-dihydro-2-benzofuran-1-one (63);

2-[(3,3-dimethyl-1-oxo-1,3-dihydro-2-benzofuran-5-yl)amino]-4-{[(1S)-2-hydroxy-1-phenylethyl]amino}-N'-(3,3,3-trifluoro-2-hydroxy-2-methylpropanoyl)pyrimidine-5-carbohydrazide (64);

5-[(4-{[(1S)-2-hydroxy-1-phenylethyl]amino}-5-[5-(1,1,1-trifluoro-2-hydroxypropan-2-yl)-1,3,4-oxadiazol-2-yl]pyrimidin-2-yl)amino]-3,3-dimethyl-1,3-dihydro-2-benzofuran-1-one (65);

5-[(4-{[(1S)-2-hydroxy-1-phenylethyl]amino}-5-[5-(pyridin-2-yl)-1,3,4-oxadiazol-2-yl]pyrimidin-2-yl)amino]-3,3-dimethyl-1,3-dihydro-2-benzofuran-1-one (66);

5-[(4-{[(1S)-2-hydroxy-1-phenylethyl]amino}-5-[5-(pyridazin-3-yl)-1,3,4-oxadiazol-2-yl]pyrimidin-2-yl)amino]-3,3-dimethyl-1,3-dihydro-2-benzofuran-1-one (67);

5-[(4-{[(1S)-2-hydroxy-1-phenylethyl]amino}-5-{5-[1-(trifluoromethyl)cyclopropyl]-1,3,4-oxadiazol-2-yl}pyrimidin-2-yl)amino]-3,3-dimethyl-1,3-dihydro-2-benzofuran-1-one (68);

(S)-5-((5-(5-(1,1-dioxidotetrahydro-2H-thiopyran-4-yl)-1,3,4-oxadiazol-2-yl)-4-((2-hydroxy-1-phenylethyl)amino)pyrimidin-2-yl)amino)-3,3-dimethylisobenzofuran-1(3H)-one (69);

1-(5-{2-[(3,3-dimethyl-1-oxo-1,3-dihydro-2-benzofuran-5-yl)amino]-4-{[(1S)-2-hydroxy-1-phenylethyl]amino}pyrimidin-5-yl}-1,3,4-oxadiazol-2-yl)cyclopropyl 3,3-difluoroazetidine-1-carboxylate (70);

ethyl 2-[(3,3-dimethyl-1-oxo-1,3-dihydro-2-benzofuran-5-yl)amino]-4-({[2-(2-hydroxypropan-2-yl)phenyl]methyl}amino)pyrimidine-5-carboxylate (71);

5-{[4-({[2-(2-hydroxypropan-2-yl)phenyl]methyl}amino)-5-(3-methyl-1,2,4-oxadiazol-5-yl)pyrimidin-2-yl]amino}-3,3-dimethyl-1,3-dihydro-2-benzofuran-1-one (72);

5-{[5-(3-cyclopropyl-1,2,4-oxadiazol-5-yl)-4-({[2-(2-hydroxypropan-2-yl)phenyl]methyl}amino)pyrimidin-2-yl]amino}-3,3-dimethyl-1,3-dihydro-2-benzofuran-1-one (73);

5-({4-[(1H-indazol-5-yl)amino]-5-(3-methyl-1,2,4-oxadiazol-5-yl)pyrimidin-2-yl}amino)-3,3-dimethyl-1,3-dihydro-2-benzofuran-1-one (74);

5-{[5-(3-cyclopropyl-1,2,4-oxadiazol-5-yl)-4-[(1H-indazol-5-yl) amino]pyrimidin-2-yl]amino}-3,3-dimethyl-1,3-dihydro-2-benzofuran-1-one (75);

ethyl 4-[(3-amino-3-methylbutyl)amino]-2-[(3,3-dimethyl-1-oxo-1,3-dihydro-2-benzofuran-5-yl)amino]pyrimidine-5-carboxylate (76);

5-({4-[(3-amino-2,2-dimethylpropyl)amino]-5-[3-(oxan-4-yl)-1,2,4-oxadiazol-5-yl]pyrimidin-2-yl}amino)-3,3-dimethyl-1,3-dihydro-2-benzofuran-1-one (77); or 5-{[5-(3-{1-azabicyclo[2.2.2]octan-4-yl}-1,2,4-oxadiazol-5-yl)-4-{[(1S)-2-hydroxy-1-phenylethyl]amino}pyrimidin-2-yl]amino}-3,3-dimethyl-1,3-dihydro-2-benzofuran-1-one (80).

15. The compound according to claim 1 or a salt thereof, wherein said compound is:

5-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-3,3-dimethyl-1,3-dihydro-2-benzofuran-1-one (46);

5-{[5-(3-cyclopropyl-1,2,4-oxadiazol-5-yl)-4-{[(1S)-2-hydroxy-1-phenylethyl]amino}pyridin-2-yl]amino}-3,3-dimethyl-1,3-dihydro-2-benzofuran-1-one (78);

5-{[5-(3-cyclopropyl-1,2,4-oxadiazol-5-yl)-4-{[(1S)-1-cyclopropyl-2-hydroxyethyl]amino}pyridin-2-yl]amino}-3,3-dimethyl-1,3-dihydro-2-benzofuran-1-one (79);

2-{[5-(3-{1-azabicyclo[2.2.2]octan-4-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b]pyridin-5-one (81);

2-{[5-(3-{1-azabicyclo[2.2.2]octan-4-yl}-1,2,4-oxadiazol-5-yl)-4-{[(1S)-1-(4-fluorophenyl)-2-hydroxyethyl]amino}pyridin-2-yl]amino}-7,7-dimethyl-5H,7H-furo[3,4-b]pyridin-5-one (82);

2-{[5-(3-{4-fluoro-1-azabicyclo[2.2.2]octan-3-yl}-1,2,4-oxadiazol-5-yl)-4-{[(1S)-2-hydroxy-1-phenylethyl]amino}pyridin-2-yl]amino}-7,7-dimethyl-5H,7H-furo[3,4-b] pyridin-5-one (83);

2-{[5-(3-{1-azabicyclo[2.2.2]octan-4-yl}-1,2,4-oxadiazol-5-yl)-4-{[(1,3-thiazol-2-yl)methyl]amino}pyridin-2-yl]amino}-7,7-dimethyl-5H,7H-furo[3,4-b] pyridin-5-one (84);

2-{[5-(3-{1-azabicyclo[2.2.2]octan-4-yl}-1,2,4-oxadiazol-5-yl)-4-{[(pyridin-3-yl)methyl]amino}pyridin-2-yl]amino}-7,7-dimethyl-5H,7H-furo[3,4-b] pyridin-5-one (85);

2-{[5-(5-cyclopropyl-1,3,4-oxadiazol-2-yl)-4-{[(1S)-2-hydroxy-1-phenylethyl]amino}pyridin-2-yl]amino}-7,7-dimethyl-5H,7H-furo[3,4-b]pyridin-5-one (86);

2'-{[5-(3-cyclopropyl-1,2,4-oxadiazol-5-yl)-4-{[(1S)-2-hydroxy-1-phenylethyl]amino}pyridin-2-yl]amino}-5'H-spiro[cyclopentane-1,7'-furo[3,4-b]pyridine]-5'-one (87); or 1-{5-[6-({7,7-dimethyl-5-oxo-5H,7H-furo[3,4-b]pyridin-2-yl}amino)-4-{[(1S)-2-hydroxy-1-phenylethyl]amino}pyridin-3-yl]-1,3,4-oxadiazol-2-yl}cyclopropane-1-carbonitrile (88).

\* \* \* \* \*

UNITED STATES PATENT AND TRADEMARK OFFICE
CERTIFICATE OF CORRECTION

| | | |
|---|---|---|
| PATENT NO. | : 11,166,959 B2 | Page 1 of 1 |
| APPLICATION NO. | : 16/761449 | |
| DATED | : November 9, 2021 | |
| INVENTOR(S) | : Erika Araujo et al. | |

It is certified that error appears in the above-identified patent and that said Letters Patent is hereby corrected as shown below:

In the Claims

Claim 1, Column 125, Line 64, delete "(=NCH$_2$CH$_3$" and replace with -- (=NCH$_2$CH$_3$) --, therefor.

Claim 1, Column 126, Line 16, delete "C$_2$-6" and insert -- C$_{2-6}$ --, therefor.

Claim 1, Column 126, Line 17, delete "C$_2$-4" and insert -- C$_{2-4}$ --, therefor.

Claim 1, Column 126, Line 67, delete "R2e;" and insert -- R$_{2c}$; --, therefor.

Claim 2, Column 127, Line 18, delete "R2" and insert -- R$_2$ --, therefor.

Claim 3, Column 127, Line 31, delete "(=NCH$_2$CH$_3$" and replace with -- (=NCH$_2$CH$_3$) --, therefor.

Claim 3, Column 127, Line 46, delete "—C(CH$_3$)$_2$H," and insert -- —C(CH$_3$)$_2$OH, --, therefor.

Claim 3, Column 127, Lines 61-62, delete "indazoly;" and insert -- indazolyl; --, therefor.

Claim 8, Column 128, Line 47, delete "(=NCH$_2$CH$_3$" and replace with -- (=NCH$_2$CH$_3$) --, therefor.

Signed and Sealed this
Sixteenth Day of September, 2025

Coke Morgan Stewart
*Acting Director of the United States Patent and Trademark Office*